(12) United States Patent
Escaf

(10) Patent No.: US 8,016,843 B2
(45) Date of Patent: Sep. 13, 2011

(54) ULTRASONIC KNIFE

(75) Inventor: Luis J. Escaf, Barranquilla (CO)

(73) Assignee: Alcon Research Ltd, Ft. Worth, TX (US)

( * ) Notice: Subject to any disclaimer, the term of this patent is extended or adjusted under 35 U.S.C. 154(b) by 460 days.

(21) Appl. No.: 11/499,871

(22) Filed: Aug. 7, 2006

(65) Prior Publication Data

US 2007/0060926 A1      Mar. 15, 2007

Related U.S. Application Data

(60) Provisional application No. 60/715,800, filed on Sep. 9, 2005.

(51) Int. Cl.
*A61F 9/007* (2006.01)
(52) U.S. Cl. ........................................................ 606/166
(58) Field of Classification Search ................. 606/32, 606/39, 45, 107, 166–167, 169; 604/22
See application file for complete search history.

(56) References Cited

U.S. PATENT DOCUMENTS

| | | | |
|---|---|---|---|
| 3,086,288 A * | 4/1963 | Balamuth et al. | 30/277.4 |
| 3,589,363 A | 6/1971 | Banko et al. | 137/81.5 |
| 3,888,004 A * | 6/1975 | Coleman | 30/277.4 |
| 4,223,676 A | 9/1980 | Wuchinich et al. | 128/276 |
| 4,246,902 A | 1/1981 | Martinez | |
| 4,428,748 A | 1/1984 | Peyman et al. | 604/22 |
| 4,504,264 A | 3/1985 | Kelman | 604/22 |
| 4,773,415 A | 9/1988 | Tan | 600/209 |
| 4,832,683 A * | 5/1989 | Idemoto et al. | 604/22 |
| 4,897,079 A | 1/1990 | Zaleski et al. | 604/22 |
| 5,047,008 A | 9/1991 | Du Juan, Jr. et al. | 604/22 |
| 5,135,481 A | 8/1992 | Nemeh | 604/22 |
| 5,154,694 A | 10/1992 | Kelman | 604/22 |
| 5,154,696 A | 10/1992 | Shearing | 604/22 |
| 5,156,607 A | 10/1992 | Kansas | 606/107 |
| 5,188,102 A * | 2/1993 | Idemoto et al. | 604/22 |

(Continued)

OTHER PUBLICATIONS

Russian Office Action mailed Oct. 11, 2010, in counterpart RU application 2009107001.

*Primary Examiner* — Todd E Manahan
*Assistant Examiner* — Ashley Cronin
(74) *Attorney, Agent, or Firm* — Smith, Gambrell & Russell, LLP

(57) ABSTRACT

An ophthalmologic cutting device having a base support section for attachment with a movement generating device and a tip with a blade section. The blade section preferably has upper and lower edges, and a forward aspiration free edge extending between them, with the upper edge having a shorter longitudinal length compared with the lower edge and where the forward edge slopes down from a distal end of the upper edge to a distal end of the lower edge, and the lower edge presenting a material contact surface that is thinner in thickness than the upper edge. A slope back in the proximal direction of the forward edge of, for example, 10 to 45 degrees with a straight and/or curving forward edge or a combination of a straight and forward edge sections is preferred. Embodiments of the blade include a blade converging in thickness from top to bottom and one having a curved upper forward edge region and one with a lower edge that has a distal straight section and a recessed section positioned proximal of said distal straight section. The forward edge is also preferably defined by longitudinally diverging, opposing side walls.

25 Claims, 50 Drawing Sheets

U.S. PATENT DOCUMENTS

| | | | |
|---|---|---|---|
| 5,217,465 A | 6/1993 | Steppe | |
| 5,217,477 A | 6/1993 | Lager | |
| 5,222,960 A | 6/1993 | Poley | 128/898 |
| 5,257,988 A | 11/1993 | L'Esperance, Jr. | 604/12 |
| 5,261,883 A | 11/1993 | Hood et al. | 604/153 |
| 5,312,413 A | 5/1994 | Eaton et al. | |
| 5,378,150 A | 1/1995 | Harrel et al. | 433/91 |
| 5,464,389 A | 11/1995 | Stahl | 604/22 |
| 5,554,155 A | 9/1996 | Awh et al. | 606/16 |
| 5,562,612 A | 10/1996 | Fox | 604/27 |
| 5,591,184 A | 1/1997 | McDonnell et al. | 606/167 |
| 5,616,120 A | 4/1997 | Andrew | 604/28 |
| 5,645,530 A * | 7/1997 | Boukhny et al. | 604/22 |
| 5,674,235 A | 10/1997 | Parisi | 606/169 |
| 5,784,787 A * | 7/1998 | Jensen | 30/168 |
| 5,810,765 A | 9/1998 | Oda | 604/31 |
| 5,836,897 A | 11/1998 | Sakurai et al. | 601/2 |
| 5,836,959 A | 11/1998 | Seibel et al. | 606/169 |
| 5,921,999 A | 7/1999 | Dileo | 606/166 |
| 5,957,914 A | 9/1999 | Cook et al. | 606/6 |
| 5,957,921 A | 9/1999 | Mirhashemi et al. | 606/34 |
| 6,039,565 A | 3/2000 | Chou et al. | 433/29 |
| 6,050,971 A | 4/2000 | Garnier et al. | 604/43 |
| 6,074,358 A | 6/2000 | Andrew et al. | 604/28 |
| 6,159,175 A | 12/2000 | Strukel et al. | 604/22 |
| 6,165,190 A | 12/2000 | Nguyen | 606/166 |
| 6,254,622 B1 * | 7/2001 | Hood | 606/169 |
| 6,258,053 B1 | 7/2001 | MacKool | |
| 6,443,969 B1 * | 9/2002 | Novak et al. | 606/169 |
| 6,478,766 B1 | 11/2002 | Chon | 604/22 |
| 6,592,541 B1 | 7/2003 | Kurwa | |
| 6,592,564 B2 | 7/2003 | Finch et al. | 604/22 |
| 6,676,628 B2 | 1/2004 | Ssman | 604/27 |
| 6,979,328 B2 | 12/2005 | Baerveldt et al. | |
| 2002/0103497 A1 * | 8/2002 | Satou | 606/169 |
| 2003/0088260 A1 | 5/2003 | Smedley et al. | |
| 2004/0116950 A1 | 6/2004 | Eibschitz-Tsimhoni | 606/167 |
| 2004/0199171 A1 | 10/2004 | Akahoshi | |
| 2004/0199192 A1 | 10/2004 | Akahoshi | |
| 2004/0232669 A1 * | 11/2004 | Leland et al. | 280/732 |
| 2005/0015104 A1 | 1/2005 | Morawski et al. | |
| 2005/0228419 A1 | 10/2005 | El-Mansoury | 606/166 |
| 2006/0047254 A1 | 3/2006 | Akahoshi | |
| 2006/0052758 A1 | 3/2006 | Dewey | |

* cited by examiner

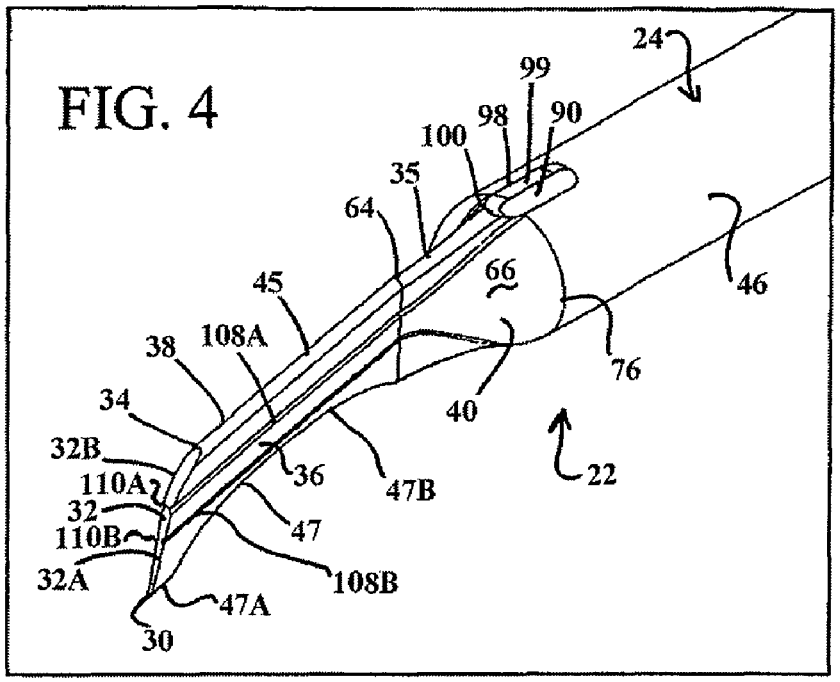
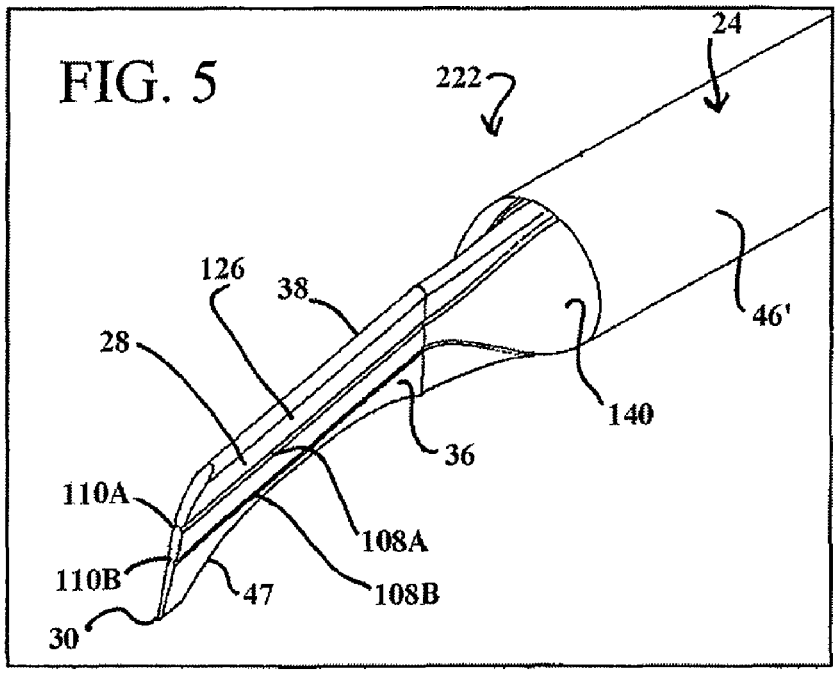

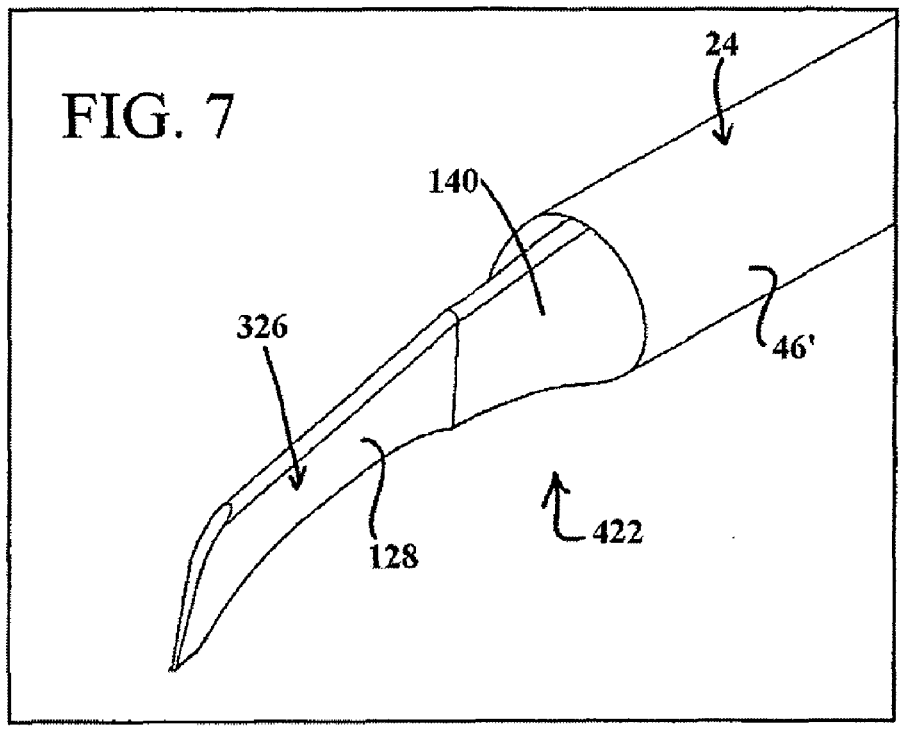

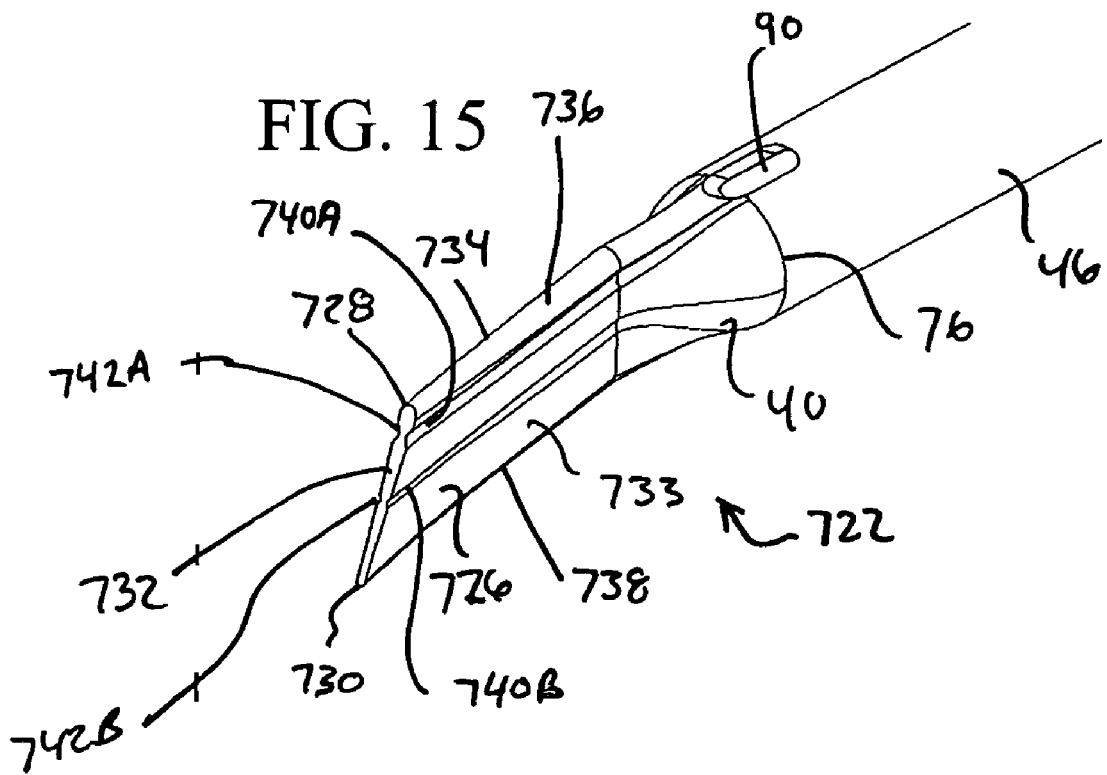
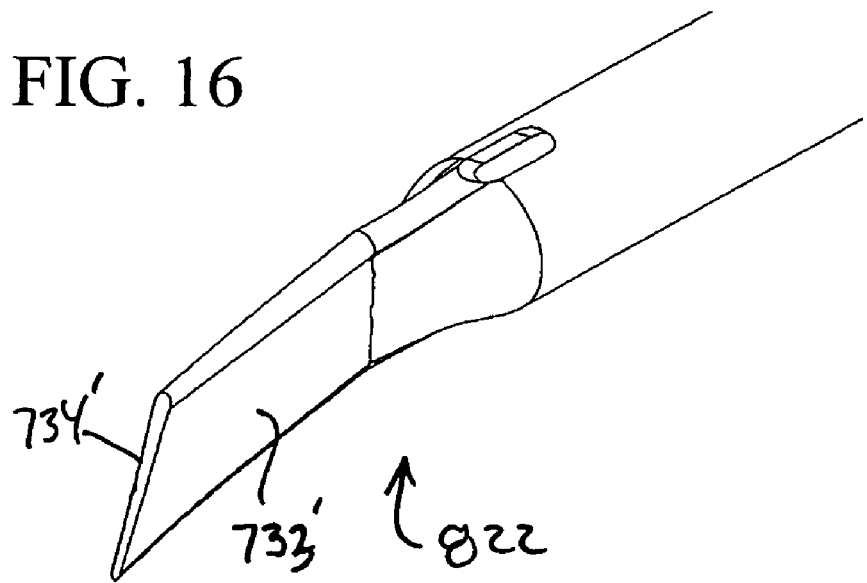

ULTRASONIC KNIFE

CROSS REFERENCE TO RELATED APPLICATIONS

The present application claims priority under 35 USC §119(e) to U.S. Provisional Patent Application 60/715,800, filed Sep. 9, 2005, which is incorporated herein by reference in its entirety.

FIELD OF THE INVENTION

The invention relates to an ultrasonic cutting device that, in a preferred embodiment, is used as a cutting device in ophthalmologic surgery. The invention also pertains to surgical instruments and techniques comprising the ultrasonic cutting device. In a preferred embodiment the surgical instrument is a phacoemulsification ophthalmologic surgical instrument and the cutting device is a phaco tip for use in that instrument which provides a cutting device that is highly efficient in cutting cataracts into more manageable fragments.

BACKGROUND OF THE INVENTION

Phacoemulsification is currently the preferred technique used by eye surgeons for cataract extraction involving the removal of the cloudy eye crystalline lens. Through a small incision in the cornea or the sclera (typically 1.5 to 3.2 mm) the cataractous crystalline lens is extracted using a device called a phacoemulsifier and then an artificial intraocular lens is implanted. This lens has the function of replacing the crystalline lens, so that the vision can be restored to the level it was before the cataract appeared.

An early phacoemulsifier can be seen in U.S. Pat. No. 3,589,363 (1971) to Kelman, which is incorporated herein by reference, that comprises a hand piece connected to a cylindrical hollow needle, which has a central bore 1.0 to 1.5 mm in diameter that is introduced inside the eye through the incision previously made. The needle vibrates as a consequence of the ultrasonic energy generated by a source inside the hand piece (usually piezoelectric crystals), which converts electricity, into ultrasonic vibration. The needle emulsifies the cataract converting its substance into very small particles that are aspirated through its central lumen in a controlled manner. The needle, however, is not designed for cutting the nucleus of the cataract or dividing it in several sizable fragments. Also, as the needle produces heat while vibrating, it is covered with a sleeve through which balanced saline solution is flowing. This fluid cools the needle and replaces the fluid being withdrawn from inside the eye, thus avoiding the collapse of the anterior chamber.

The needle involved in many prior art techniques has a cylindrical shape with a diameter between 1.0 to 1.5 mm, and thus is not well suited for cutting or separating the cataract in sizable fragments, which is the preferred approach taken in modern phacoemulsification techniques. In an effort to do so, a technique has been developed which includes sculpting channels or grooves in the surface of the cataract using the cylindrical needle. The grooves must be wider than the needle's diameter so that the cataract may be cracked into four segments (the so called divide and conquer nucleofractis). In order to sculpt grooves in cataracts of a certain hardness level, there is utilized a high power of ultrasonic energy. This has been shown to be able to produce damage to the eye, if applied for a long enough period of time. Moreover, even with the application of high ultrasonic energy levels, the dividing of a very advanced cataract still may not be possible using the method of sculpting grooves, as these cylindrical hollow needles are not really adequate to divide the cataract in sizable fragments by themselves. In an effort to avoid the necessity of sculpting grooves, other surgical instruments have been designed that use mechanical energy to divide the cataract while attempting to save ultrasonic energy. These mechanical devices include choppers and pre-choppers. Many models are available (for instance: Nagahara's chopper available from Rumex Ophthalmic Surgical Instruments, St. Petersburg, Fla., USA—Reference: 7-063 TH) and Akahoshi's pre-chopper (Asico, Westmont, Ill., USA—Reference Universal AE-4282)). These devices use mechanical energy to divide the nucleus. However, phaco chop techniques can be more technically difficult, leading to a greater likelihood of complications, and, moreover, dividing hard nucleus (brunescent and black) cataracts with pre-chopping techniques may be very difficult to master by surgeons.

Currently there are several phacoemulsification devices available (Infiniti Vision System, Alcon Inc., Fort Worth, Tex., USA; Sovereign, Advanced Medical Optics, Santa Ana, Calif., USA; Millennium, Bausch & Lomb, Rochester, N.Y., USA) that use different pumps and different needles. An example of a phacoemulsification device is found in U.S. Pat. No. 6,478,766 assigned to Alcon, Sic. (Hunenberg, CH), which patent is incorporated herein by reference. The Infiniti System phacoemulsification device of Alcon Inc., Fort Worth, Tex., USA has the option of using, in addition to the ultrasound sonic energy, fluid liquefaction of the cataract to help break down the cataract (e.g., see U.S. Pat. Nos. 5,616,120 and 6,676,628 also to Alcon which are incorporated herein by reference). The newer phacoemulsification devices also have the capability of modulating the power of ultrasound applied. In general the manufacturers have designed them to extract the cataract after dividing it into sizable fragments (e.g., four or more) which are then emulsified using cylindrical needles.

U.S. Pat. No. 4,504,264 to Kelman, which is incorporated herein by reference, describes an ophthalmological instrument that features an aspiration needle that is longitudinally vibrated as well as laterally oscillated. The lateral oscillation is described as working in association with the longitudinal vibration movement to promote more rapid fragmentation.

U.S. Pat. No. 6,592,541 to Kurwa, which is incorporated herein by reference, describes and ophthalmological device for cutting a nucleus of a cataract with a phaco tip having a body with a solid blade with a face edge. The device is used alternately with a standard phaco tip (needle with open end) to remove cataracts. As will become more apparent below (e.g., see the Summary of Invention discussion below) the cutting phaco tip, has a design that is not efficient in many respects in the cutting and fragmentizing of the wide range of cataract types faced.

Due to the limitations as to current phacoemulsification surgical instruments available, ophthalmologists around the world rely on basically the same phacoemulsification surgical technique, with some minor variations. The phacoemulsification surgical technique currently relied upon includes the following basic steps:

1. The providing of an access incision which is typically corneal or scleral with a size often varying between 1 and 3.2 mm. The incision may be located superiorly (12 or 11 o'clock positions), or completely temporal. Incision architecture may vary. There may be utilized single plane, two plane or three plane incisions, depending on the surgeon's preference. All of these incisions are intended to be watertight and do not require sutures to close.

2. Capsulorhexis is the surgical step where a central circular portion of the anterior capsule is removed and it leaves the anterior cortex of the cataract exposed. In other words capsulotomy involves creating a continuous tear of the anterior wall to produce a smooth-edged round opening. The continuous tear capsulotomy is known as "capsulorhexis". Such a capsulotomy facilitates removal of the old lens and also facilitates in-the-bag implantation of an intraocular lens. There are several modes of capsulorhexis forceps and as some examples reference is made to U.S. Publication 2004/0116950 A1 to Elibschitz—Tsimhoni and U.S. Publication 2005/0228419 to El-Mansoury for a discussion of capsulotomy techniques and instruments.

3. Hydrodisection is a maneuver by which, using balanced saline solution injection, the cortex of the cataract is separated from the capsules, so that the cataract can rotate inside the bag.

4. Hydrodelineation is a maneuver by which, using balanced saline solution, the nucleus of the cataract is separated from the most peripheral portion of the cataract that is epinucleus and cortex, so that the nucleus can rotate freely.

5. Nuclear pre-fracture is a more recent cataract surgical technique wherein, before trying to emulsify a cataract, the nucleus is divided into sizable fragments by one of several methods, such as those described above, in order to facilitate its extraction. As noted above, since the phacoemulsification cylindrical needles can emulsify and aspirate just one small portion of the cataract at a time, and not big portions of the cataract, the pre-fracture technique facilitates the complete removal of the cataract material as with a subsequently applied cylindrical phacoemulsification needle. One pre-fracture method involves sculpting deep grooves inside the cataract with the phaco needle to provide for the fragmentation using the needle, and a second instrument to push the fragments apart. The downside of this technique is that it requires more ultrasonic energy, especially in hard and black cataracts, and this high energy level requirement can cause damage to the cornea. Moreover, using this method sometimes it can be impossible to divide certain very hard cataracts (like black cataracts), and it may be necessary to widen the surgical incision to extract it in one piece and then suture it, which is undesirable from a post treatment healing standpoint.

6. Other alternative techniques to divide the cataract before emulsifying it, is using the choppers and the prechoppers (like the above described Nagahara's chopper and Akahoshi's prechopper), which use mechanical energy. They have the drawback of being difficult to learn, taking a long time for the surgeon to master these techniques. Moreover they have the risk of rupture of the anterior capsule edge (in the case of choppers) or zonular stress (in the case of prechoppers). In very hard nucleus (brunescent and black cataracts), these techniques are not easy to perform, even for the experienced surgeon, since the fragments do not separate completely, but their fibers are stretched without breaking.

SUMMARY OF THE INVENTION

The subject matter of the present invention includes a cutting device as in an ultrasonic cutting device designed to cut a cataract in sizable and manipulatable fragments with little difficulty, unlike the standard phacoemulsification cylindrical needles which are not well suited to easily divide the cataract in that manner. A preferred embodiment features an ultrasonic cutting device comprising a shaft, which may be hollow or solid, and an opposing side walled "flattened" tip disposed at a distal end of the shaft. This tip vibrates at ultrasonic frequency, and is suitable for replacing the mechanical energy used by choppers and pre-choppers thus providing for efficient usage of ultrasonic energy. The ultrasonic knife of the subject matter of the present invention makes it possible to easily and efficiently divide the cataract in as many fragments as the surgeon deems desirable (e.g., 4 to 12). The cutting device of the present invention provides a tip design that easily and efficiently cuts through a wide assortment of cataract types (e.g., lower energy usage and associated lowering of heat generation with less trauma potential). For example, the cutting device of the present invention works in softer cataracts like "a hot knife cutting through butter", and in harder cataracts (including brunescent and black cataracts) like "a hot knife cutting through a chocolate bar".

The new ophthalmologic cutting device of the present invention provides a tool which permits a surgeon to improve on the phacoemulsification technique, making it easier to divide the cataract into several manipulatable fragments which can then be, for example, more easily emulsified with a standard phacoemulsification needle, diminishing the amount of ultrasonic energy applied during cataract extraction, and thus reducing the risk of damage to the cornea. In addition, the produced fragments can also be more easily liquefied with technologies that employ fluid pulses, making the present cutting device even more applicable to harder cataracts.

The cutting device of the present invention thus provides an "ultrachopper" that makes for easier performance of a phacoemulsification technique; as in a phacoemulsification technique that includes a breaking apart of the cataractous crystalline lens into more manageable pieces via the ultrachopper to facilitate completion of the phacoemulsification process as by applying a vibrating aspirating needle on the more manageable pieces created with the ultrachopper. Another alternative to finish the cataract extraction following the fracture with the ultrachopper is using a liquid application tool (e.g., a heated and pulsing liquefaction based further breakdown tool) to liquefy and aspirate the fragments. This procedure provides a hybrid, phacoemulsification/liquefaction procedure (which is categorized under the present invention as a phacoemulsification procedure and phacoemulsification tooling in general). Thus, with the ultrachopper, surgeons who are not highly experienced may learn these techniques in less time and with fewer complications, and experienced surgeons may improve even more their outcomes.

The above-described present invention's ultrachopper and its efficient breakdown or fragmentation of a cataract into several more manageable or manipulatable pieces is also readily incorporated into a variety of cataract removal surgical techniques and thus also improves on the cataract removal process in general under those techniques. For example, some of the cataract removal surgical techniques involving ultrasonic or combined sonic-ultrasonic phacoemulsification and/or liquefaction techniques can utilize the subject matter of the present invention and can be categorized into the following "A to C" surgical techniques, which removal techniques and associated equipment are considered to fall under the subject matter of the present invention:

A) ULTRAPHACO
B) ULTRAQUAL
C) ULTRAMICS

As an example of the new "ultraphaco" cataract removal technique under the subject matter of the present invention, following or during the course of dividing the cataract with the ultrasonic knife or ultrachopper of the present invention (either with longitudinal phaco tip oscillation alone or a combination of longitudinal and lateral oscillation), the fragments are emulsified using a standard cataract emulsification needle with ultrasound. The entire cataract removal technique can be rapidly completed as the ultrachopper not only rapidly cuts through even hard cataracts but also separates them, especially when using oscillatory sonic or ultrasonic motion and presents broken up cataract pieces to the needle so that they can be more readily broken down further and aspirated out through the needle.

As an example of the "ultraqual" cataract removal technique under the subject matter of the present invention, following or during the course of dividing the cataract with the ultrachopper, the fragments are liquefied using fluid fragmentation means as in a liquefaction fragmentation means using heated liquid pulses propelled from a tip as in the liquid pulse fragmentation "Aqualase" or as in the liquid pulse fragmentation "Infiniti System" of Alcon noted above. The "ultraqual" cataract removal technique thus provides for rapid cataract removal completion as the ultrachopper not only rapidly completes its fragmentation function, but presents fragmented cataract pieces that can be readily further broken down with fluid fragmentation means as in the noted "Aqualase" system (or even a combination of the further fragmentation techniques described above and below, although use of just one further break up of fragmentation (when needed in light of the ultrachopper's effectiveness in and of itself) is preferred over multiple supplemental fragmentation from the standpoint of rapid completion of the surgical procedure).

As an example of the new "ultramics" cataract removal technique under the subject matter of the present invention, following use of the ultrachopper, the emulsifier means (e.g., needle) of the ultrasonic handpiece or the probe of the Aqualase handpiece is introduced, without sleeve, through an incision having a length below 1.5 mm.

Thus, an example of a phacoemulsification technique under the present invention includes two main steps: prefracture and emulsification of the fragments with ultrasonic energy with the ultrachopper representing a phacoemulsification instrument. Also, while liquefaction is not generally classified as phacoemulsification, since it uses liquid pulses instead of ultrasound, the ultraqual technique is considered a phacoemulsification technique by providing a hybrid technique that uses the phacoemulsification ultrachopper instrument initially for pre-fracture and then, for instance, the Aqualase probe for removing the fragments by liquefaction. Various other arrangements involving pre-fracture means to readily break up cataracts into more manageable pieces and removal means for removing the results of the pre-fracture means (e.g., further breaking down the manageable pieces to facilitate exiting of the material to be removed).

The ultrasonic knife or cutting devices of a preferred embodiment of the invention includes a tip having many functions and intrinsic features, having a design directed at providing benefits to the surgeon and patient alike. The benefits at which the present invention is directed toward include, for example: a lessening of surgical time, applied ultrasound energy, and the time required for learning the technique of using the device. Additional potential benefits include, for example, faster recovery times for the patient, better control ability in the surgeon during phacoemulsification, the making available of new techniques of phacoemulsification, and the possibility of implanting intraocular lenses through smaller incisions. Also, in a preferred embodiment, the cutting device is subjected to the lateral oscillation in addition to the longitudinal vibration to promote more rapid fragmentation and separation of the pieces of nuclear material with the ultrachopper.

A preferred embodiment of the present invention includes a cutting device with a tip that is distally flattened and made of an efficient ultrasonic energy transforming material such as a metal as in titanium or steel that has an ultrasonic energy transfer section such as a solid or hollow shaft (e.g. completely hollow along axial length of the hollow shaft or hollow over an axial portion of the overall length of the shaft). When utilizing a hollow shaft that has a larger peripheral area than the distal blade portion of the tip, there is featured a transition section where the flattened portion joins with the preferably cylindrical shaft portion and in that transition section there is preferably provided an aspiration hole or holes that are preferably formed entirely in the transition section and/or partly in the transition section and partly in the hollow shaft section. The holes include, for example, either a superior and/or one or two lateral (preferably oval) shaped aspiration holes, which provide aspiration port(s) that are in fluid (and typically fluid is inclusive of aspirated solids) communication with an inner lumen. The lumen formed in the shaft forms part of an overall aspiration passageway, which preferably traverses the shaft (e.g., a cylindrical lumen extending in the full length of a cylindrical hollow shaft) and travels within the handpiece sleeve in typical flow through fashion.

An alternate embodiment features a solid shaft and a solid transition region in the area where the flattened portion joins with the cylindrical portion and thus this embodiment preferably does not contain any hole. This alternate embodiment of the invention has each one of the flattened portion's "pinched" lateral faces provided with a groove or grooves (e.g. two grooves on each flattened face or side wall) in order to diminish friction when contacting the cataract material. There is also, however, featured under the subject matter of the present invention, an embodiment of the tip free of cut facilitating grooves. A preferred embodiment of the invention also features an angulation of the tip, which preferably includes an upper edge having a slope down of about 15° in relation with the horizontal and then a forward edge assuming an angle, relative to the vertical axis as it extends proximally back from the distal most end of the lower blade edge that is preferably about 15 degrees (e.g. 15°±5°). In addition, for its preferred usage in breaking up cataracts, the area of surface of the tip is preferably about 4 mm$^2$ as in from 4.16 mm$^2$ to 4.18 mm$^2$.

In a preferred embodiment there is an irrigation sleeve, which covers the shaft of the device, and preferably covers the shaft up to the area where the flattened portion begins (e.g., preferably up to the distal side of the hole in the boundary with the transition section, leaving the length of a flattened tip—e.g., 2.5 to 2.6 mm—exposed). This facilitates the sleeve covering (i.e., axially extension covering) the superior oval hole, and/or the lateral holes in the above-noted aspiration port embodiments. This sleeve-to-port arrangement helps to assure that when moving the cutting device backward to place the tip in contact with the proximal area of a cataract, the irrigation port or ports located laterally in the distal portion of the sleeve do not travel outside the anterior chamber which can disrupt the surgical procedure. The length of the distal tip of material contact edge is also preferably not more than 3.0 mm (e.g., 2.5 mm to 2.8 mm) from the suction orifice which also helps in avoiding the irrigation port's suction orifice traveling outside the anterior chamber.

The opposing side walled or flattened portion of the cutting device's tip is preferably arranged not only to work as a knife splitting the cataract, but also as a dissecting spatula, moving apart the divided portions of the cataract. Also, in embodiments which have one or more aspiration holes, the larger diameter of the (preferably oval) hole or holes is preferably arranged parallel to the longitudinal axis of the device. Also the flattened portions of the cutting device tip are preferably made thinner in the inferior area, than in the superior one. Also the ultrasonic energy applied to the tip is preferably applied in two different manners. The first manner includes movement of the tip axially in an antero-posterior motion (i.e., a longitudinal to and fro movement) the second manner places the tip in or with an oscillatory motion, with a excursion of, for example, up to 10° as in a 2 to 10° range, with a 2.5 to 5.0° oscillation range being preferable (this added lateral ultrasonic movement feature is made possible with some new phacoemulsifiers instruments such as the aforementioned Infiniti System of Alcon and which have the possibility of using sonic or ultrasonic oscillatory movement with specific handpieces). The oscillatory sonic motion may be performed together with the ultrasonic movement or in sequence (either one preceding the other) or one without the other depending on the circumstances (e.g. groove formation first to a sufficient degree to take advantage of lateral oscillation within the groove thus formed, followed by any variety of longitudinal or lateral oscillation applications as the operator deems best under the current circumstances). In other words, a means for tip position manipulation preferably provides for both antero-posterior motion and oscillatory motion (preferably the antero-posterior is utilized first to form an initial cut or groove, and then there is initiated the lateral oscillatory movement to help break up the object in the process of being cut—although a variety of timing arrangements for the two motions as in simultaneous or alternating sequences can be utilized depending on the circumstances faced by the surgeon). This arrangement helps in promoting the capability of having the tip simultaneously cut and move apart the fragments during the fragmentation process.

A preferred embodiment of the present invention includes a cutting device that has a tip with a blade that is thinner at the bottom (initial material contact) edge and a thicker at the top edge (a more upper positioned edge relative to the lower edge and which upper edge is generally opposite to the lower edge as in one that is parallel or generally parallel to the lower edge such as one that is within 10 degrees of being parallel). Having the upper edge thicker than the lower edge provides an advantageously oriented wedge shape in the tip. This arrangement is unlike, for example, the above described Kurwa reference, which does not show a narrowing of cross section in the side walls' spacing. Accordingly, Kurwa lacks the beneficial wedge shape that is provided in a preferred tip embodiment of the present invention which wedge shape allows the device to cut through the nuclear material without causing excessive stress on the capsular bag and zonular apparatus.

Moreover, a preferred embodiment of the present invention includes the feature of having the edge on top of the blade, which preferably extends in straight line fashion, shorter than the lower one, which is also a design feature unlike the Kurwa's device. A shorter upper edge is an additional advantageous feature that promotes safety, since when the blade goes forward during the cutting of the cataract, the blade portion that first penetrates the nuclear material is the longest part of the bottom, and when moving farther forward this bottom edge can be displaced under the opposite anterior capsule edge, but since the superior edge is shorter there will be some extra space, making the possibility of injuring this edge, or the iris, very low.

Another advantageous feature found in a preferred embodiment of the present invention, which Kurwa again fails to appreciate, is the angulation of the tip as in having a forward edge of the tip slope (curved and/or straight) proximally such as from the distal most end as in a tip that is angulated 15 degrees with respect to the horizontal. This angulation feature allows the tip to be more easily used. For example, to reach the nuclear material the surgeon does not need to tilt the device too much. Moreover this angulation feature can increase the cutting device's safety, because the possibility of injuring the anterior capsule edge in the area located opposite to the incision is significantly reduced.

BRIEF DESCRIPTION OF THE DRAWINGS

Other features and technical advantages of the present invention will become more apparent from a study of the following description and the accompanying drawings, in which:

FIG. 4 shows a partial perspective view of the distal end of the cutting device shown in FIG. 3.

FIG. 5 shows a partial perspective view of the cutting device shown in FIG. 2.

FIG. 7 shows a modified embodiment of the cutting device shown in FIG. 5, with the FIG. 7 embodiment being free of grooved side walls.

FIG. 15 shows another perspective view of the cutting device shown in FIG. 12.

FIG. 16 shows a modified embodiment of the cutting device shown in FIG. 15, but with the FIG. 16 embodiment being free of grooved side walls.

DETAILED DESCRIPTION OF PREFERRED EMBODIMENTS OF THE INVENTION

The aforementioned Figures are illustrative of a plurality of preferred embodiments, although the present invention is not intended to be limited to those embodiments. The illustrated embodiments are inclusive of embodiments having planar side walled configured distal tip blades providing a "flattened" (in appearance—as the distal blade can be formed or manufactured in a variety of ways such as molding, machining or material manipulation forming, etc) tipped cutting device. The illustrated embodiments also depict two different types of (preferably cylindrical) shafts, one hollow and the other solid amongst the various embodiments depicted. When attached to a hollow shaft or barrel, the flattened tips preferably have apertures as in one or more aspiration holes (e.g., one or more (preferably one) upper edge holes and/or one or more (preferably two opposite) side aspiration holes), with the illustrated embodiments depicting one and two holes, respectively, in communication with the bore of a hollow shaft.

Embodiments of the essentially planar, opposing side walled or "flattened" phaco tips of the present invention feature embodiments with grooves in their lateral surfaces as well as embodiments free of such grooves. The embodiments shown in the Figures also show different tip designs with a phaco tip such as that shown in FIGS. 4 to 11 being well suited for cutting through hard or very hard (brunescent and black) cataracts (although this tip design is also efficient in use with other characteristic cataracts including soft and medium density or hardness cataracts). The embodiment depicted in FIGS. 15 to 19 and the embodiment illustrated in FIGS. 23 to 26 are well suited for use with the soft to medium hardness cataracts, although the FIG. 15 embodiment and FIG. 23 embodiment are also suited for use with harder cataracts, although deemed less efficient relative to the FIG. 4 embodiment. The opposite can also be said in that an embodiment such as that in FIG. 4, while being designed for use with harder cataracts, is also suited for use with softer cataracts, albeit in a manner considered less efficient than the FIG. 15 and FIG. 23 embodiment relative to softer cataract material.

Figure 1:
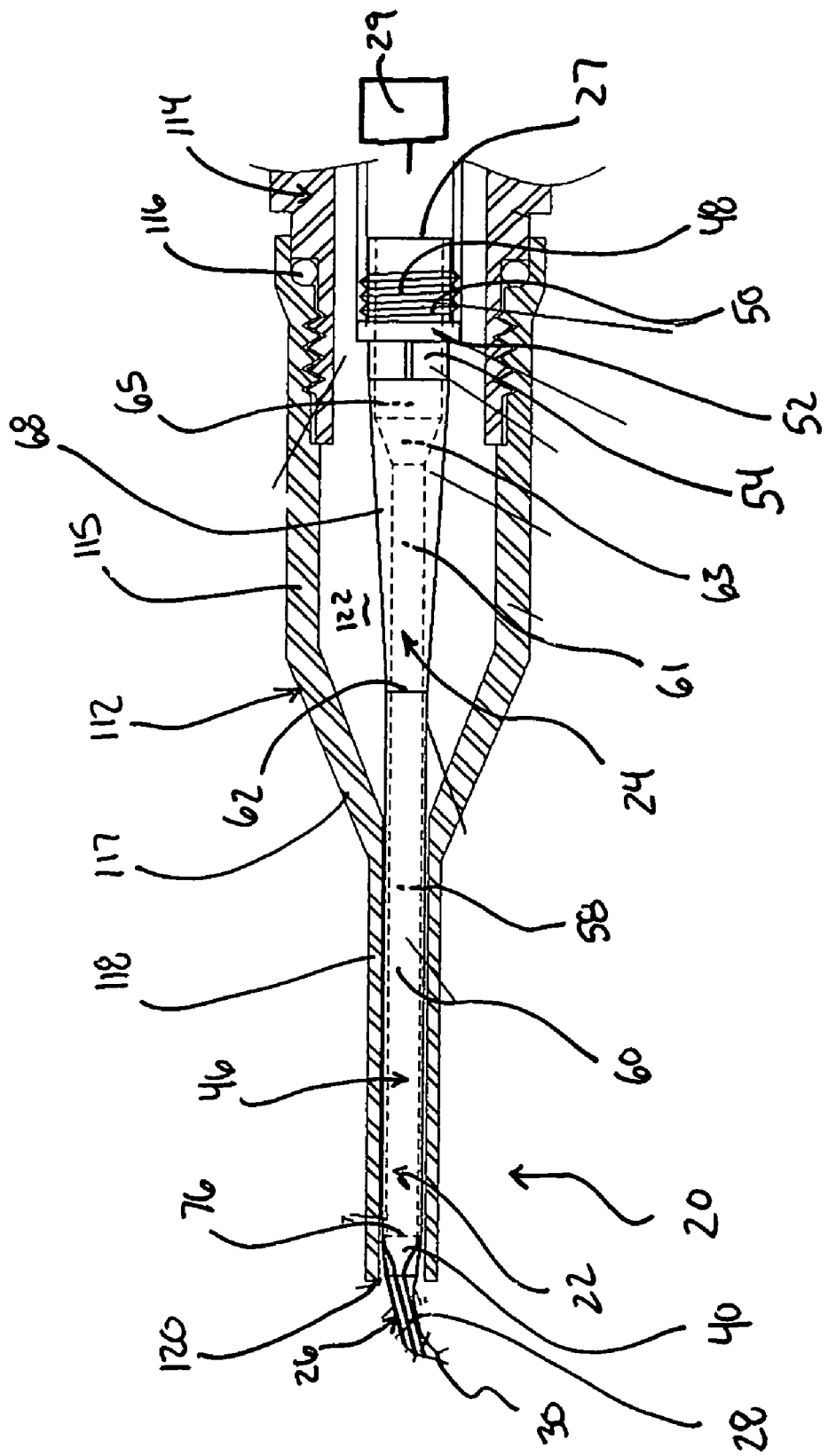
FIG. 1 shows a partially cut away view of an ophthalmologic surgical instrument with cutting device having an aspiration passage in the cutting device's shaft.

With reference to FIG. 1, there is shown a partially cut away view of a surgical instrument in the form of a phacoemulsification ophthalmologic surgical instrument 20. Instrument 20 includes a cutting device 22 (also referenced below as a knife, chopper and "ultrachopper"). In the embodiment shown in FIG. 1 and corresponding FIGS. 3, 3A, 3B, and 4, cutting device 22 comprises ultrasonic energy transmission section 24 and tip 26. Transmission section 24 preferably extends between the proximal end 76 of tip 26 and the proximal end 27 of cutting device 22. Tip 26 is shown as comprising transition section 40 and blade 28 with the blade having distally positioned, opposing (generally) planar side walls 36 and 38 that together provide a "flattened," "material contact" portion in the cutting device 22. Transition section 40 extends from the distal most end 76 of energy transmission section 24 to the proximal most end 64 of blade 28.

In a preferred embodiment, energy transmission section 24 includes shaft 46 (FIG. 1 featuring a hollow or internalized aspirating passageway embodiment, and FIG. 2 featuring a solid shaft or non-aspirating embodiment 46') as well as connector 48 (or means for attachment) to a movement generator (schematically shown at 29 which is preferably in the form of an ultrasonic vibrating device such as one utilizing a piezoelectric transducer, although alternate movement generating devices are also featured under the present invention including, for example, alone or in conjunction with one or the other, fluid, acoustic, motor (e.g., offset cam), reciprocating piston or other movement generating means.

Figure 2:
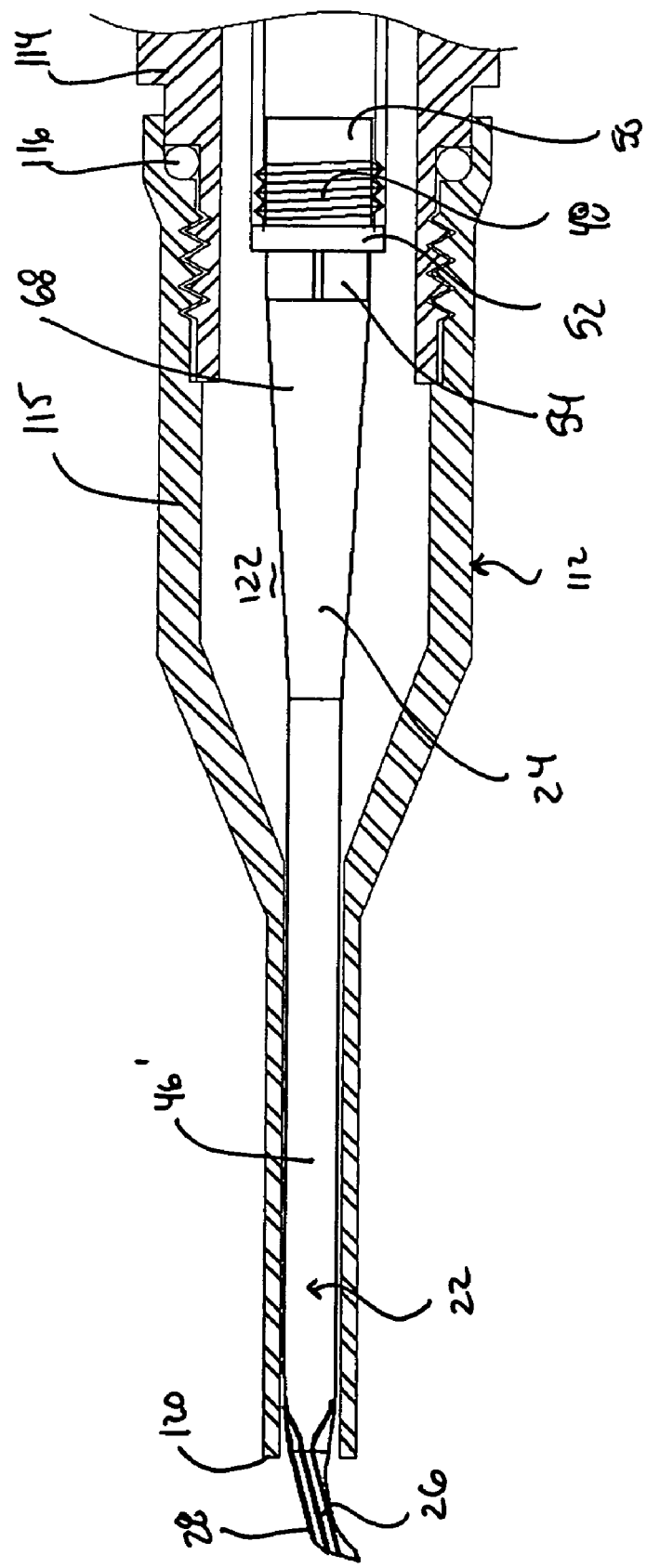
FIG. 2 shows an alternate embodiment of the surgical instrument in FIG. 1 with a solid or non-axial aspirating cutting device shaft.

In a preferred embodiment shaft 46 includes a cylindrical shaft segment 60 that is preferably approximately 14 mm in length and 1 mm in diameter, although a variety of alternate cross-sectioned shaped, preferably straight shaft segments and lengths are featured under the subject matter of the present invention. Shaft segment 60 can be hollow or solid, according to the model of the device, with FIG. 1 showing an embodiment that is hollow having axially extending lumen 58 forming part of an aspiration passageway 61 and with lumen 58 preferably having an internal surface diameter between 0.8 to 0.9 mm. FIG. 2, on the other hand, shows a solid shaft segment 60 and thus is free, at least internally, of an aspiration passageway. Between the proximal end 62 of shaft segment 60 and proximal end 27 of cutting device 22 there is provided transition (preferably cone shaped) segment 68, which is preferably about 8 mm in length (e.g., 8.02 mm length) with an inclination in relation to the horizontal axis of about 3 to 5 degrees (e.g., approximately 3.6 degrees) and preferably has a narrow distal diameter end (e.g., 1 mm) and a wider proximal end (e.g., 2 mm). Also, between those two end points is also found flange disk 52 (e.g., one that is about 2.5 mm (e.g., 2.62 mm) in diameter and with a width of approximate 0.5 mm) sandwiched between threaded cylindrical male projection tube 50 and square head 54 (e.g., a square of approximate 2×2 mm and 1 mm in thickness). It should be noted that all dimensions provided above and below throughout this application are not intended to be limiting, but of assistance in illustrating some of the possible characteristics of some of the embodiments of the invention including dimensions that, for example, are well suited for a surgeon positioning and utilizing the surgical instrument of the present invention within the limited space eye environment involved as well as providing a cutting device that is readily attachable to preexisting movement generators and irrigation systems. For instance, the threaded male connection tube 50 and step down conical shaft 68 features described above are also present in standard models of phacoemulsification devices and thus the cutting device 22 of the present invention is well-suited for ready replacement of prior art cutting devices designed for securement to standard phacoemulsification handpieces such as that represented by housing 114. In other words, the illustrated male connection tube 50 with standard threaded proximal three thread rings on a supporting cylinder of approximately 2 mm in diameter and 4.65 mm in length is adapted for attachment to any one of a variety of phacoemulsification handpieces, many of which utilize a piezoelectric vibration source such as vibration source 29. In addition, when irrigation fluid circulation is desired to help cool the vibrating cutting device and/or provide fluid circulation within the surgical area of the eye, there is preferably provided sleeve 112, which is typically formed of a medical grade silicone and has a proximal sleeve segment 115 with threaded connection with housing 114 and fluid seal 116. Sleeve 112 also preferably has a step down conical transition zone 117 between the larger cylindrical proximal segment 115 and shaft sleeve segment 118. Sleeve segment 118 has distal end 120 (a distal irrigation flow end when fluid is flowing in sleeve 112) with an interior surface just slightly larger in diameter (e.g., 0.2 to 0.5 mm larger) in order to maintain an open irrigation radial space along shaft segment 60 relative to the axially corresponding exterior portion of shaft 46 for irrigation flow control out of the space between the distal end 120 of sleeve segment 118 and the underlying preferably tapering tip transition section 40 of tip 26.

Sleeve segment 115 has a larger interior diameter than the interior positioned cutting device and thus there is formed annular space 122 between the sleeve end portion 115 and shaft 46. Fluid inflow is provided within space 122 in the illustrated embodiment such that irrigation fluid circulates within and through annular space 122 as well as at the annular space formed between the sleeve's distal end 120 of sleeve segment 118 and the axially corresponding exterior portion of transition section 40 preferably at least partly covered over by sleeve segment 118.

With reference to FIG. 4 there is illustrated aspiration port 90 which is used with the hollow version of shaft 46 shown in FIG. 1. Aspiration port 90 is in fluid communication with lumen 58 of aspiration passageway 61 with the straight lumen section 58 shown extending within cylindrical shaft segment 60 as well as within the conical transition section 68 of shaft 46 Lumen 58 of aspiration passageway 61 also feeds into diverging passage section 63 of aspiration passageway 61 and then into enlarged diameter proximal passage section 65 of aspiration passageway extending within the handpiece or housing 114 of the phacoemulsification instrument. As seen from FIG. 1, aspiration port 90 is positioned so as to have its distal end 100 axially proximal relative to distal sleeve end 120 (e.g. preferably a distance D of less than 1 mm with 0.15 to 0.3 mm there between being preferable with FIG. 3A not drawn to scale in this respect). As also seen from FIG. 4, aspiration port 90 extends axially (longitudinally) to opposite axial sides of border line 76 representing a boundary line between the sloped transition section 40 and the shaft 46. In this way, there is a scoop effect (a radial inward sloping deviation in a percentage of the aspiration port outer boundary wall forward of the boundary line 76 (e.g. 20 to 25% of the whole axial length of port 90 is forward of boundary line 76)) due to the aspiration port's outer boundary wall and interior boundary wall conforming to the slope of convergence in exterior surface 66 of transition section 40 (e.g., a slope of 65 to 70 degrees from the horizontal).

Aspiration hole or port 90 is shown positioned at a superior or upper edge in use position relative to shaft 46 and is preferably more elongated in the axial direction of extension along the major axis 92 of the instrument than in a lateral direction transverse thereto along minor axis 94 with an oval or elliptical shape being preferred. A ratio difference of 1.5/1 to 4/1 (e.g. 2/1) relative to axial length/lateral width is preferred, with a preferred embodiment having a 0.4 to 1.0 mm length (e.g. a length of 0.6 mm length and 0.3 mm width), with rounded ends which have a radius of curvature of about 0.15 mm. Also, as shown in FIGS. 4 and 6A port 90 is preferably comprised of exterior aspiration port boundary edge 98 and a sloped wall 99 extending radially inward to an interior boundary edge 100. The slope of wall 99 is preferably in a common direction both at the proximal and distal end of the aperture port 90. An example of this can be seen in the cross-sectional view of FIG. 6A showing parallel line segments 99A and 99B for wall 99 which provides for enhanced emulsification outflow as the distal to proximal sloping wall arrangement that opens directly into lumen 58 of shaft segment 60. A slope of 30° to 60° is preferred with 45° slope being suitable for many uses. Aspiration port 90 thus provides for fluid recirculation access from the surgical region of the eye with that eye region being fed with fluid via the irrigation outlet at the distal end 120 of sleeve 112. Thus the superior positioned aspiration port 90 is in fluid communication with the lumen 58 of the hollow cylindrical shaft 46, and port 90 thus provides for the aspiration of fluids and also some debris originated when cutting and emulsifying a cataract. A preferred axial location for the distal end of aspiration hole from the distal most point 30 of tip 26 is about 2.2 to 2.8 mm with about 2.65 mm±0.5 mm being preferred. The distal end of sleeve 120 when present is thus about 2.7 to 2.9 mm from the distal most end of tip 26 with 2.8 mm±0.25 mm being preferred.

Figure 3:
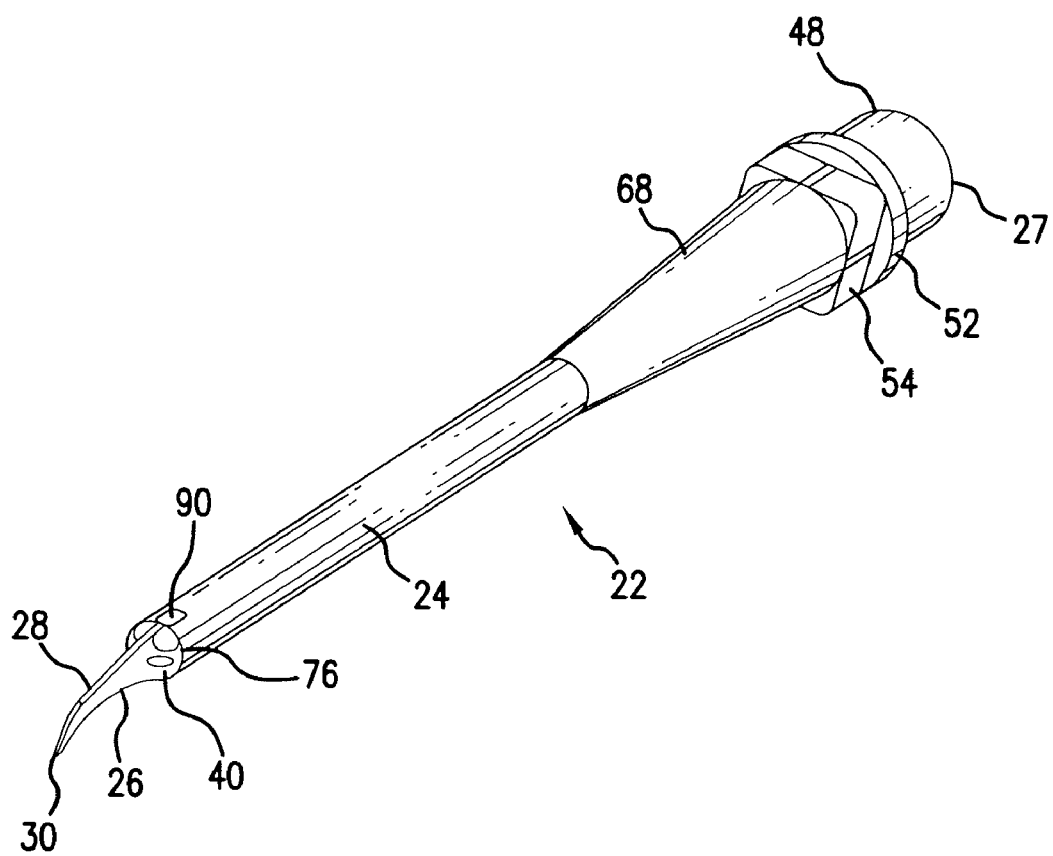
FIG. 3 shows a perspective view of the cutting device shown installed in the surgical instrument of FIG. 1.
Figure 3A:
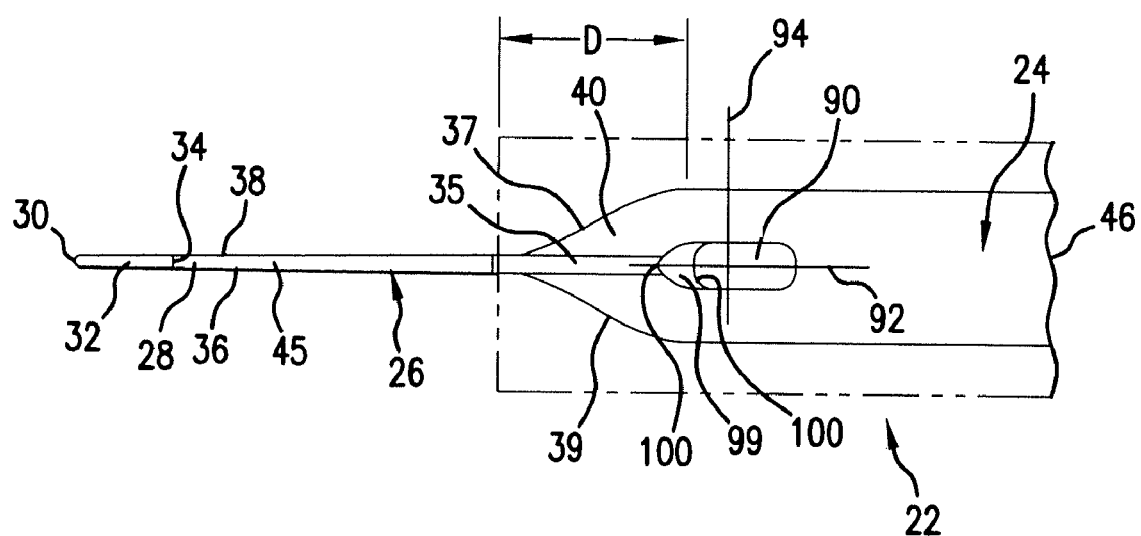
FIG. 3A shows a partial top (or superior) plan view of the cutting device shown in FIG. 3.

FIG. 3 shows cutting device 22 in perspective including its tip 26 with blade section 28 and transition section 40. In FIGS. 3, 3A, 3B, 4 transition section 40 is shown as having pinched, axially converging (curved in elevation) side transition walls 37, 39 (FIG. 6) leading distally to the blade 28 and having superior upper transition edge or ridge 35 and a similar configured inferior transition ridge 41, with the superior transition ridge 35 having a rounded off cross section to correspond with the rounded off cross-section in upper edge 45 of blade 28. FIG. 3 also depicts in perspective ultrasonic energy transition section 24 having threaded projection tube 50, flange disk 52, square head 54 and shaft 46 comprising cone-shaped segment 68 and cylindrical shaft segment 60.

Figure 3B:
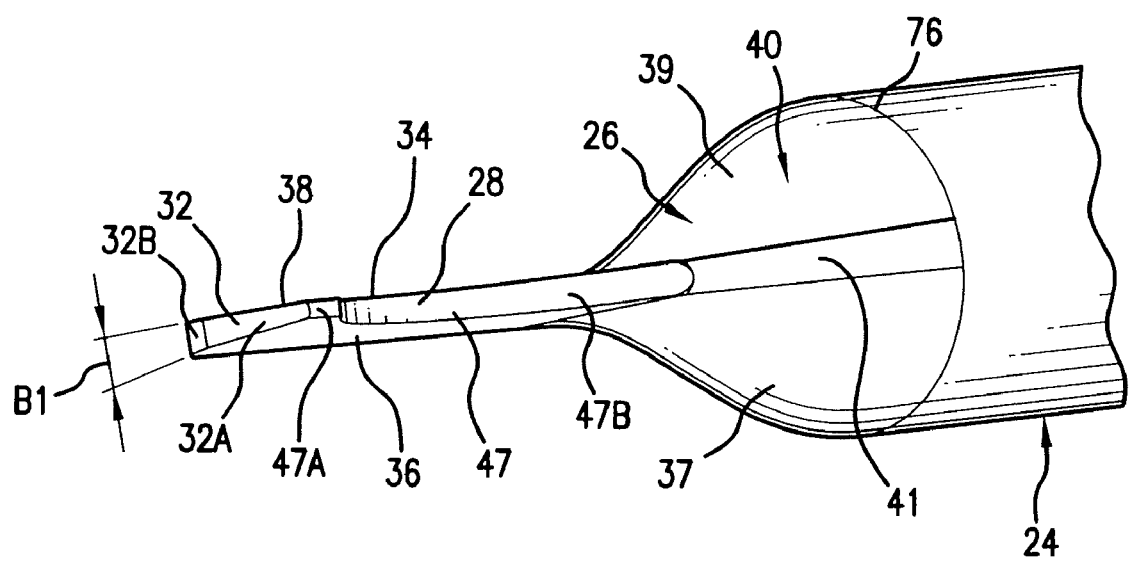
FIG. 3B shows a partial bottom (or inferior) perspective view of the cutting device shown in FIG. 3

FIGS. 3A, 3B, 4, 5, 8 and 8A illustrate in greater detail an embodiment of tip 26 which provides a phaco tip for cutting through a cataract which is particularly well suited for cutting through harder cataracts such as black and brunescent cataracts. As seen, blade section 28 has opposing, generally planar side walls 36 and 38 extend from a thicker upper edge 45 to a lower thinner width edge 47 (with edge 47 being "sharper" but is as shown in FIG. 3B still preferably rounded off in cross section in, for example, the straight, material contact lower edging portions in edge section 47A to help avoid iris damage. This inferior edge can also represent a non-rounded edge as in a vertex line edge or a flat bottom edge with sharp angle side wall extensions, but the advantage of being rounded lies in less potential for damaging the iris or the anterior capsule during the instrument insertion into the eye, although during the cutting action itself the edging is not of concern for causing eye damage. Thus, for the additional benefit of damage avoidance during the insertion and removal from an incision, a preferred embodiment features a concave profile (e.g., that shown in 47B, FIG. 5), although the alternate edge configuration also form part of the subject matter of the present invention.

Figure 8:
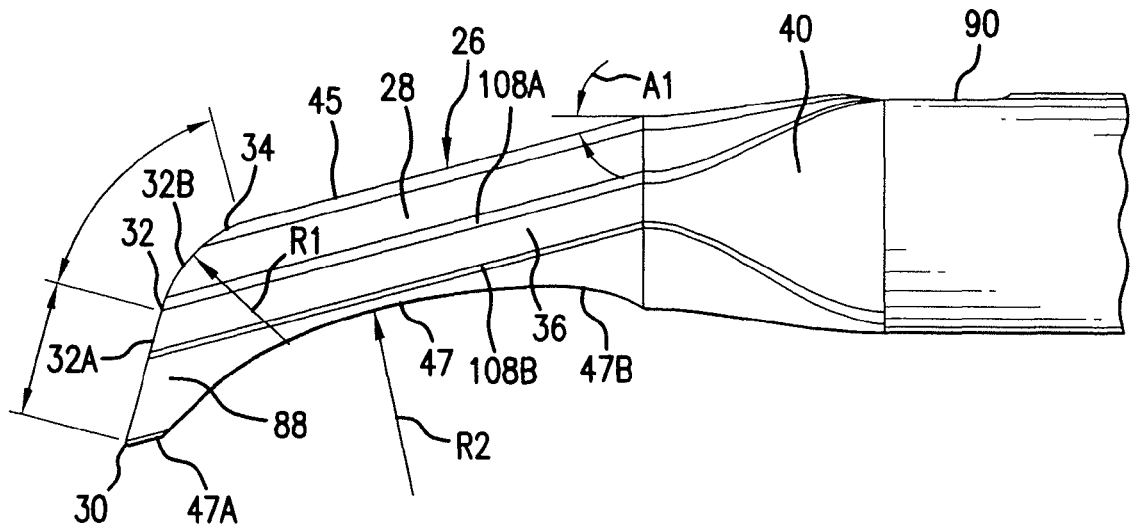
FIG. 8 shows a side elevational view of that which is shown in FIG. 4.

Upper edge 45 preferably has a thickness of about 1.5 to 5 times that of the lower sharper edge 47 with a range of 0.4 mm to 0.9 mm being preferable for upper edge 45 and 0.2 to 0.5 mm (e.g. 0.3 or 0.4 mm) for lower edge 47. Thus blade 28 has a ship's keel configuration (at least at the distal end relative to the hook-shaped blade in the FIG. 1 embodiment blade and fully for the FIG. 2 embodiment which is described in greater detail below). Blade 28 includes an inferior, material contact point 30 representing the distal most point on the blade, and hence also that of the cutter 22. Extending upward and sloping in a distal to proximal direction from point 30 is superior forward edge 32 of blade 28 which forward edge goes from a thicker upper end to a thinner bottom end as it conforms with the converging side walls 36 and 38. Forward edge 32 is shown in the Figures as extending from inferior material contact point 30 and then proximally back toward the shaft until it reaches superior upper end point 34. Forward edge 32 is also shown as a curving edge with a preferred arrangement being one where there is a straight line slope forward edge section 32A transitioning into a curved upper forward edge section 32B. Proximal end point 34 for forward edge 32 also coincides with the distal end for upper edge 45, while the opposite end of edge 45 is represented by boundary line 64 (FIG. 8) at the distal end of transition section 40. FIG. 8 also shows downwardly sloping upper edge 45 sloping downward from the horizontal by angle A1 which is preferably from 5° to 30° and more preferably about 15° (e.g., 15°±5°).

Figure 8A:
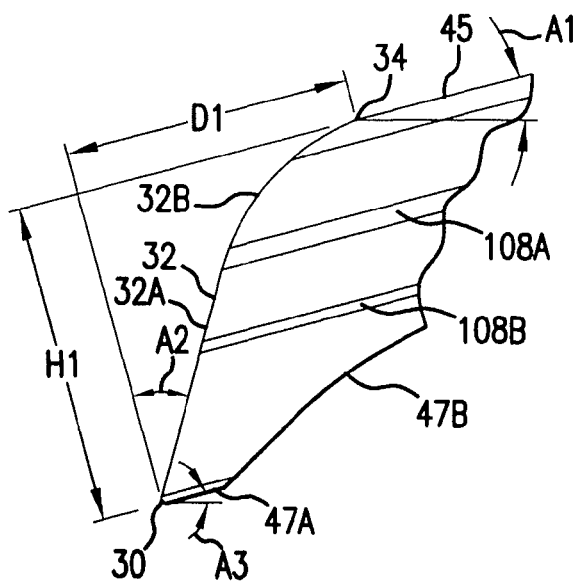
FIG. 8A shows an enlarged, cut-away view of the distalmost region of the tip shown in FIG. 8.

FIGS. 8, 8A and 3B also provide a view of the blade's lower edge 47 featuring straight section 47A and a recessed (preferably curved as in a concave curve) section 47B. End point 30 represents the vertex for angles A2 and A3 shown in FIGS. 8 and 8A. Angle A2 represents the angle that the inferior segment 32A of forward edge 32 slopes proximally from the vertical. An angle of 15 to 45° is preferred with an angle of about 15 to 30°±5° being well suited for use under the invention, with 15°±5° being preferred. Angle A3 represents the slope upward off the horizontal that lower edge segment 47A assumes which is preferably about 5° to 30° with an angle of about 15°±5° being well suited for the purposes of this invention. In a preferred embodiment the upper edge 45 and the lower edge extend in parallel fashion or in generally parallel fashion as in within 10° of being parallel (e.g. a 5° or less offset form a parallel orientation).

Forward edge 32 is shown to have convex curving segment 32B extending proximally away from inferior segment 32A. Segment 32B provides a rounded transition upper corner between segment 32A and edge 45. This curved segment 32B preferably has a radius of curvature of between 1.0 and 2.0 mm with 1.25±0.2 mm being preferred. The overall length of forward edge 32 is about 2.0 mm±0.5 mm with the overall vertical height between points 30 and 32 preferably being about 0.75 to 2.0 mm with 1.0 mm±0.2 mm being preferred. Also, the relative % of segments 32A and 32B relative to the overall length of forward edge 32 is preferably about 60%±10% in edge 32A and 40%±10% in curved edge 32B.

The convergence of side walls 36 and 38, in going down from upper edge 45 to lower edge 47 has angle B1 (shown in FIG. 3B for this embodiment and in FIG. 22 for an alternate embodiment) but which angle is preferably about 5 to 10° wide with 7°+1° being preferred. Each of upper edge 45 and lower edge 47 can maintain a constant thickness value in going proximally away from the distal end along the longitudinal or axial direction of the instrument. However, in a preferred embodiment in addition to the above described vertical convergence in walls 36 and 38 there is preferably provided in those side walls 36 and 38 a minor degree of divergence in extending longitudinally away from the distal end of the cutting device (with the width of the upper and lower edges 45 and 47 also diverging along the longitudinal with the side walls in similar fashion to the convergence of the forward edge 32 relative to the convergence of the side walls in the vertical). The degree of divergence in the upper and lower edges 45 and 47 is preferably a relatively minor divergence angle in the axial direction (with a distal to proximal divergence of, for example, 3 to 4° and more preferably about 3.5°) which helps the blade provide a separation effect to promote fragmentation breakaway. For example, starting with the above maintained forward edge 32 defined upper and lower edge thickness levels, a slight expansion in going in the proximal direction is provided. For instance, the lower edge section preferably diverges in the distal to proximal direction from a thinnest point 30 located at the distal end of lower edge 47. Preferably the lower non-curved section 47A has a minimum thickness of about 0.3 mm at the distal end point 30 and then slightly diverges outward over its length and then a continued divergence is provided in the more proximal section 47B. Also, the boundary edge between sections 47A and 47B of lower edge 47 is preferably represented by a rounded off corner (to avoid iris and anterior capsule damage) although a non-rounded off corner at this location is also featured under the present invention. The divergence of lower edge 47 is preferably such that it goes from the minimum distal thickness of 0.3 mm to a thicker proximal end thickness which is preferably of a lateral thickness greater than 0.4 mm as in 0.5 to 0.7 mm in lateral thickness. An alternate embodiment includes having edge segment 47A of a constant thin thickness in the axial direction and then lower edge 47 expanding out as described above starting with the segment 47B. Also, the recessed portion of section 47B preferably extends over the entire distance between the proximal end of section 47A to the distal end of transition section 40.

As shown in FIG. 4, the upper edge 45 (and continuing on with ridge 35) also preferably diverges outward in going from the distal to proximal direction, with the expansion preferably originating at the upper end point 32B and continuing on to the transition section border 76 (e.g., a distal thickness of 0.4 mm at end 32B to a proximal thickness of 0.9 mm at the aspiration port 90 region).

By providing a thinner, "sharp" (e.g. relatively sharp but preferably having rounded edging in the width direction or in going between the sidewalls) edge distal blade segment there is an initial reduction in cataract cutting resistance while the tip design also provides for highly effective transmission of ultrasonic energy to the tip. Bottom edge section 47A continues directly from the end of recessed bottom blade section 47B up to distal most point 30 and is preferably straight and ends at a sharp point at 30 with the assistance of the straight edge portion 32A of forward edge 32. Its longitudinal (proximal to distal) length is preferably between 0.1 mm and 0.4 mm with a 0.15 mm±0.04 mm being preferred. Its thickness preferably is from 0.03 to 0.3 mm to give a sharp edge feature.

Concave lower edge segment 47B preferably has a radius greater than that of radius R1 of forward edge segment 32B with FIG. 8 showing a curative radius R2 which is preferably 1.75 to 2.5 mm with 2.0 mm±0.2 mm being preferred. This recessed region 47B in the lower blade edge segment 47B facilitates the avoidance of non-desirable iris or other eye segment inadvertent contact when the cutting device 22 is displaced backward.

Also as seen from FIGS. 8 and 8A, the point 30 is distally further positioned along the axial length of cutting device 22 than point 34 representing the border line between the more sloping forward edge 32 and the less sloping upper edge 45. Thus the overall top edge is shorter than the overall bottom edge of the cutting devices blade 28 along a straight line. This provides for a cutting process wherein, when the blade goes forward, the blade part what must penetrate the cataract (e.g. a cataract nucleus) first is the longest bottom part while the shorter upper part is shaped to avoid harming the iris on the top edge of the capsule during the cutter movement along the cataract. FIGS. 8A illustrates this difference via reference "D1" which extends axially between the farthest distal lower edge point 30 and the farthest distal upper edge point 34 between which forward edge 32 extends (in view of the uninterrupted edging of both the forward edge 32 and the upper edge 45, the upper edge point 34 is preferably that portion of the total superior edging (extending proximally off from point 30 and distally from the distal end of the transition section) that represents a boundary point between a more vertical or about equal vertical rise section as compared to the longitudinal rise of that total superior edging (as represented by forward edge 32) and the less vertically rising section of that total superior edging (as represented by upper edge 45). Alternatively, point 32B can be considered the demarcation point wherein there is an initiation of an increase in the degree of downward slope as compared to a region constituting either a less sloping or non-sloping upper edge region of the blade (if both less sloping and non-sloping upper edge regions are proximal to the demarcation point than whichever is the more distal is the comparison frame of reference). In a preferred embodiment this difference D1 is about 0.35 to 0.5 with 0.45 mm±0.05 mm being preferred.

FIG. 1 also represents an embodiment of blade 28 that is inclusive of side wall grooving which facilitates the dividing of the cataract nucleus with less ultrasonic energy output and a reduction in resistance to cut formation, particularly with respect to harder cataracts that are more likely to have hard enough material to span the thin-grooves rather than be compressed into the grooves. As seen from FIGS. 4 and 8, the blade 28 embodiment of the present invention includes a plurality of grooves or serrations formed in the side walls of the blade with there preferably being a plurality of vertically space apart grooves on each side wall (e.g., two on each side wall spaced vertically apart form each other and from their respective closest upper and lower edges of the blade). FIGS. 4, 5, and 8 illustrate a pair of grooves 108A and 108B on side wall 36 and a pair of grooves 110A and 110B on the opposite side wall 38. The grooves within a pair preferably extend parallel to one another along the flattened blade portion and then follow the curved exterior surface at the same height level in traveling back to boundary edge 76 at shaft 46. The upper and lower positioned grooves on side wall 36 also preferably are at a common height level with the respective upper and lower grooves on opposite wall 38. Both the depth and vertical width of the grooves 108A, 108B, 110A, 110B is preferably less than 0.1 mm with examples being 0.05 mm±0.025 mm for the depth and 0.06 mm±0.025 for the vertical width. Upper grooves 108A and 110A are preferably positioned within the upper ½ of the maximum vertical height of blade 28 with a preferred embodiment placing the upper groove around the ⅓ mark as in 0.3 mm down from upper edge 45 for a 1.0 mm maximum vertical height blade 28. The grooves preferably have a consistent depth and height along their full axial length. Also, the lower set of grooves 108B and 110B on each side wall preferably have the same dimensions as the upper groove while being positioned within the lower half of the vertical height of blade 28 with about a ⅔ down position point from the upper edge being preferred as in a 0.6 mm down from the upper edge 45 positioning for a 1.0 mm height blade. Also the axial length preference for transition section 40 comprising an aspiration port or multiple aspiration ports is preferably about the same as the vertical height of blade 28 as in a 1.0 mm axial length in transition section 40.

FIG. 5 shows cutting device 222 which has a tip 126 similar in all respects to tip 26 including a common blade 28 design as shown in FIG. 4, but tip 126 comprises a modified transition section 140 and a modified shaft section 46' with both being a solid mass free of any internal aspiration passageways. Thus there is no internal aspiration carried out with cutting device 222 in FIG. 5.

Figure 6:
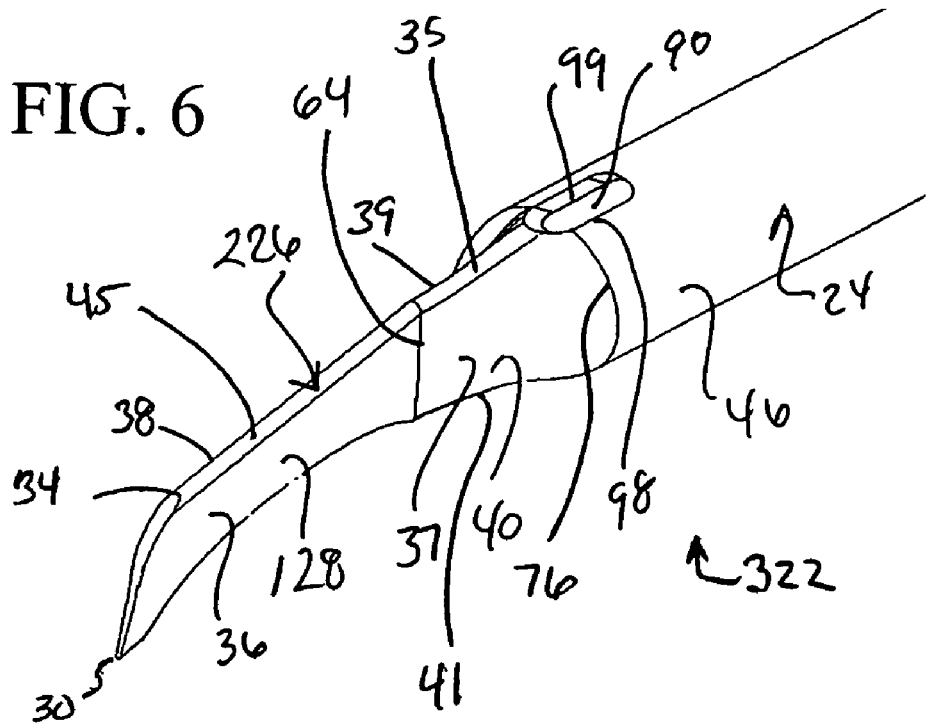
FIG. 6 shows a modified embodiment of the cutting device with aspiration port shown in FIG. 4, with the FIG. 6 embodiment being free of grooved side walls.
Figure 6A:
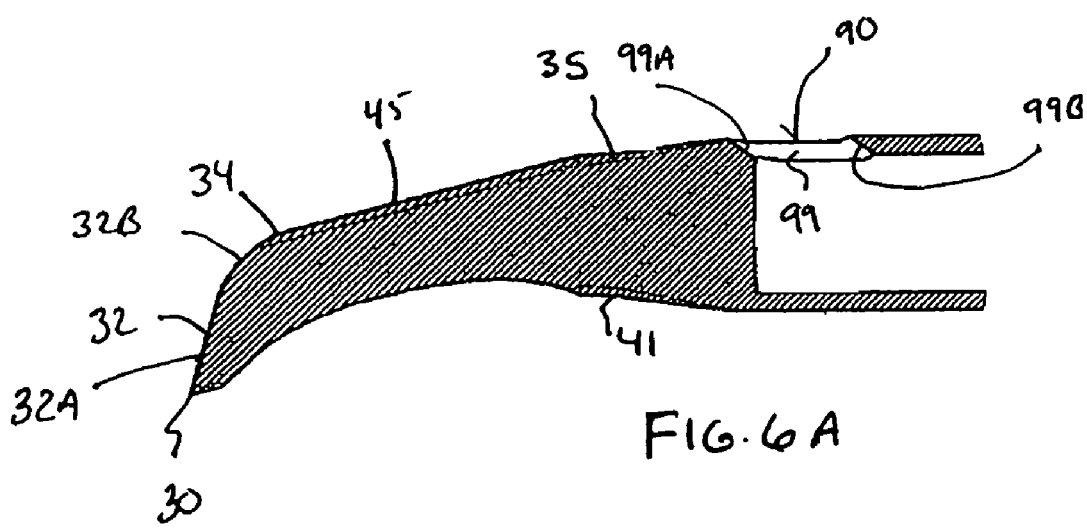
FIG. 6A shows a vertical bi-sect of the tip shown in FIG. 6.

FIG. 6 shows an alternate embodiment cutting device 322 with its tip 226 including a generally similar design as to tip 26 in FIG. 4, but for its blade 128 being different than blade 28. That is, blade 128 has the same configuration as blade 28 in FIG. 4, but the opposing walls 36 and 38 are free of any grooving along their surface so as to present uninterrupted smooth surfacing on each of side walls 36 and 38, as well as preferably their corresponding transition walls 37 and 39 as border line 64 preferably represents a smooth (large radiuses) fillet type transition.

FIG. 7 shows an alternate embodiment of cutting device referenced as 422 and having tip 326 with a similar blade 128 as in FIG. 6, but cutting device 422 features a solid shaft 46' and transition region 140 and free of any aspiration ports (e.g., the small amount of debris of material originated during the fragmentation can flow out of the eye with the fluid outflow through the incisions).

Figure 9:
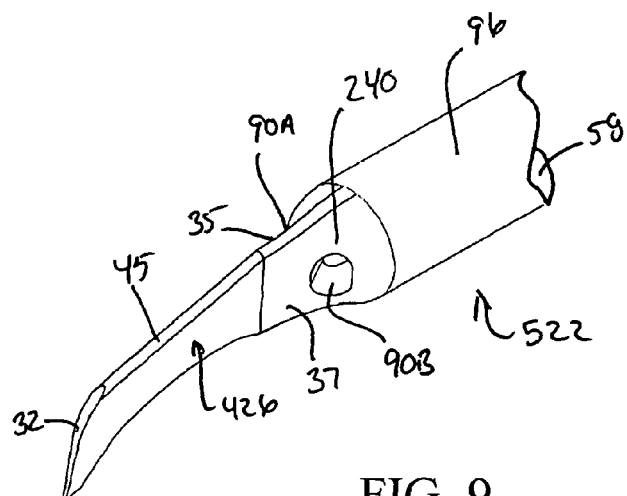
FIG. 9 shows an alternate embodiment of the cutting device which is free of side wall grooves and has side aspiration ports in place of the superior or upper edge aspiration port shown in FIG. 6.

FIG. 9 shows an alternate embodiment cutting device 522 having tip 426 which is similar in all respects to cutting device 322, but for a modification in the aspiration hole arrangement distal of the shaft 46. In FIG. 9, rather than having a superior edge positioned aspiration port, there is provided aspiration porting in transition walls 37 and/or 39. Each aspiration hole 90A and 90B provided in the transition section 40 (e.g. within the intermediate region 25% to 75% of the overall axial length of transition section 40) communicates with lumen 58 provided within hollow shaft 46.

Figure 10:
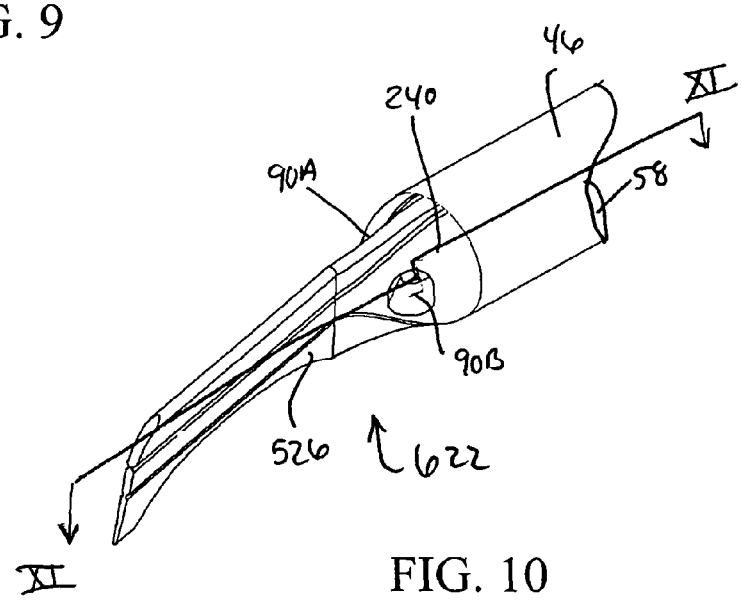
FIG. 10 shows a view similar to FIG. 9 but for an embodiment inclusive of side wall grooves

FIG. 10 shows an alternate embodiment cutting device 622 with tip 526 with the latter having a blade section similar to blade 28 in FIG. 1, but a transition section 240 similar to that in FIG. 9 in that it includes ports 90A and 90B.

Figure 11:
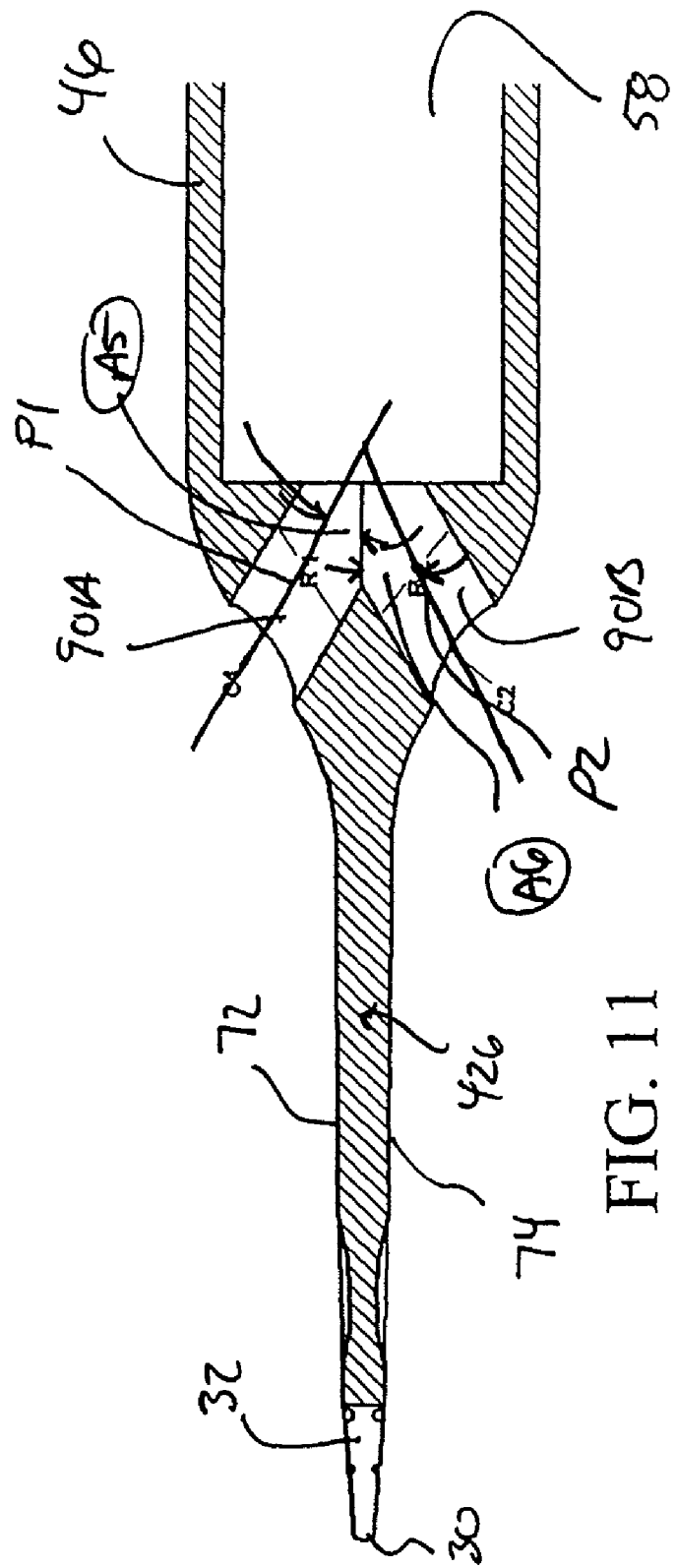
FIG. 11 shows a cut-away view of the cutting device in FIG. 10 taken along cross section line XI-XI in FIG. 10.

FIG. 11 provides a cross-sectioned new taken along cross-section line XI-XI in FIG. 10 showing aspiration opening 90A and 90B former in the sloping exterior surfaces of transition walls 72 and 74 and communication with aspiration conduits P1 and P2 extending through the thickened region of transition section 240 until opening out at the distal end of lumen 58 formed in shaft 46. A preferred distance for passageways P1 and P2 is about 1.5 mm±0.5 mm (e.g., a 1 mm axial length in a transition of 2 mm and a 1.5 mm passageway length with angles A5 and A6 preferably being from 25° to 35° with an equal value such as 30° being preferred for each).

The area for each of the aforementioned tip embodiments such as tip 26 preferably has an area less than or equal to 5 mm² as in one between 4 to 5 mm² such as 4.16 to 4.18 mm² being well suited (with the area being inclusive of blade section 28 and transition section 40 in vertical bi-section).

Reference now is made to the alternate embodiments of the cutting device depicted in FIGS. 12 to 21. As seen from a comparison of FIGS. 1 to 11 and FIGS. 12 to 21, the difference between the various embodiments largely is found in the tip design. The tip design shown in FIGS. 12 to 21 is particularly well-suited for use with softer type cataracts when compared with harder type cataracts such as black and brunescent harder cataracts.

Figure 12:
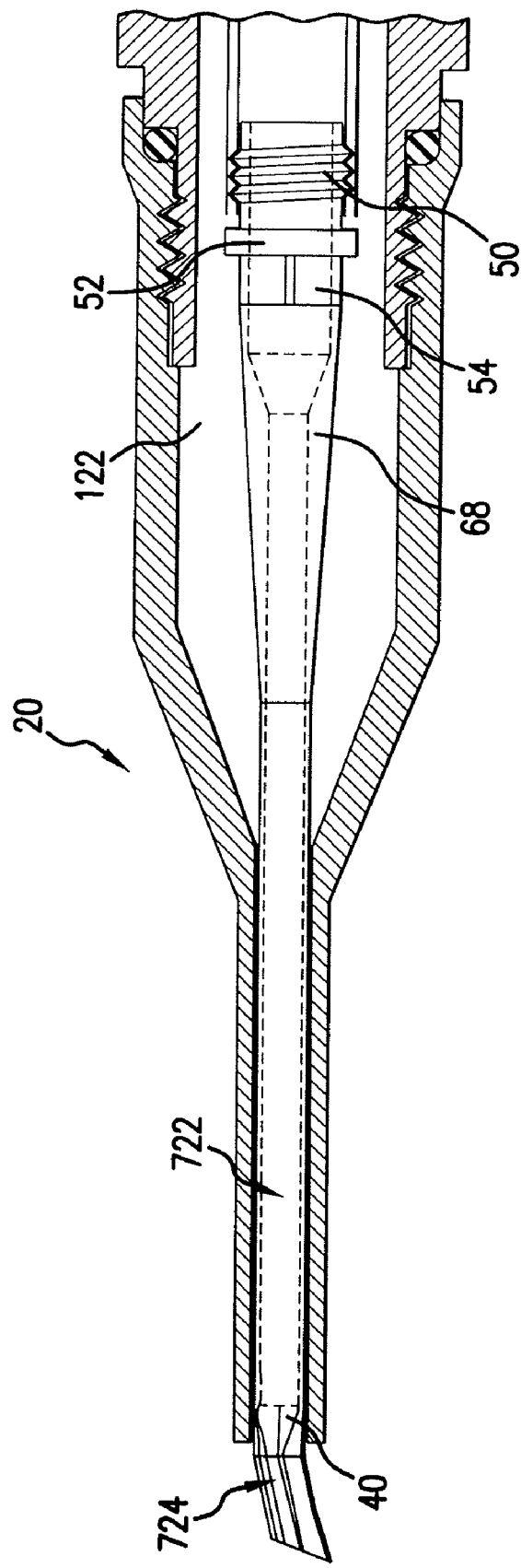
FIG. 12 shows a partially cut away view of the ophthalmologic surgical instrument similar to that shown in FIG. 1 but having mounted therein an alternate embodiment of the present invention's cutting device which is an embodiment having an extended flat bottom edge free of a recess as in the bottom edge of FIG. 1 which is inclusive of a curved recess in its bottom, material contact edge.
Figure 13:
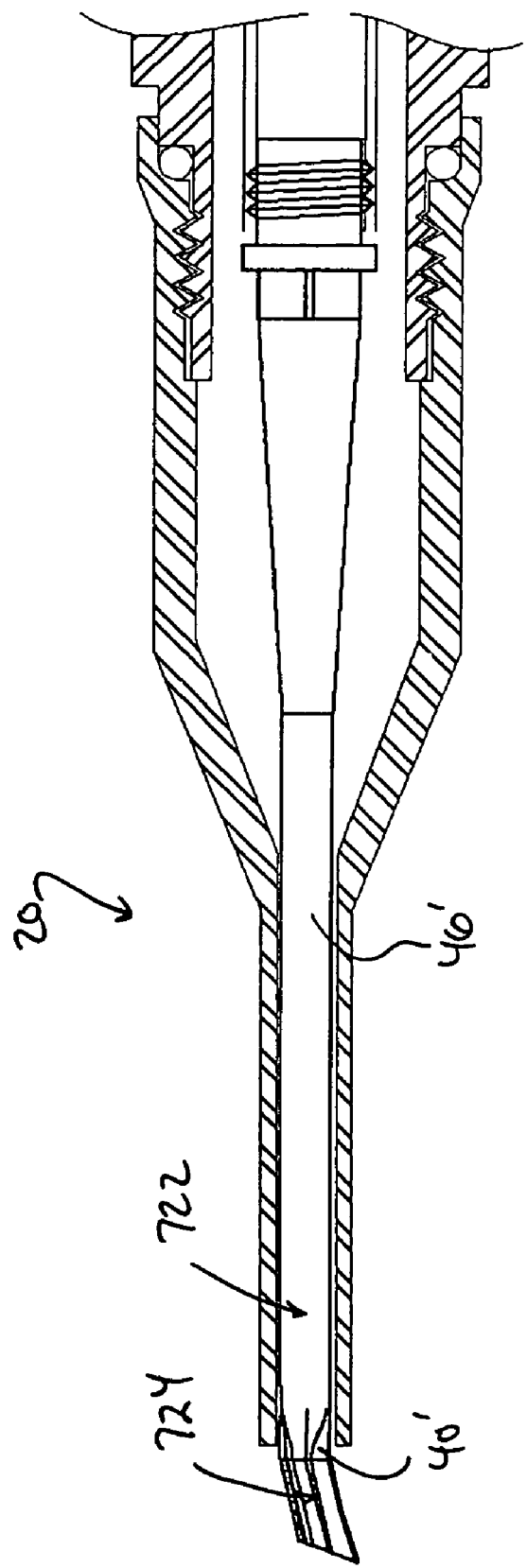
FIG. 13 shows a view similar to FIG. 12 but for an alternate embodiment of the cutting device featuring a solid cutting device shaft.
Figure 14:
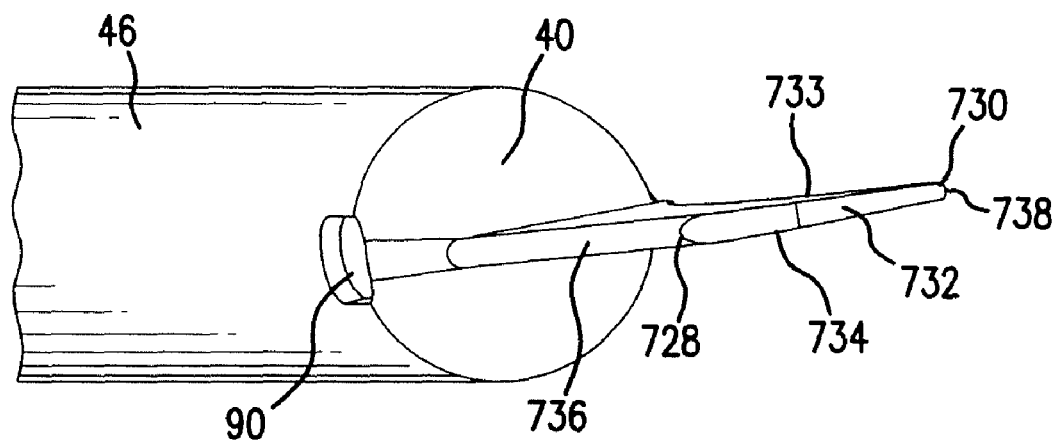
FIG. 14 shows a superior perspective view of the distal end of the cutting device shown in FIG. 12.
Figure 19:
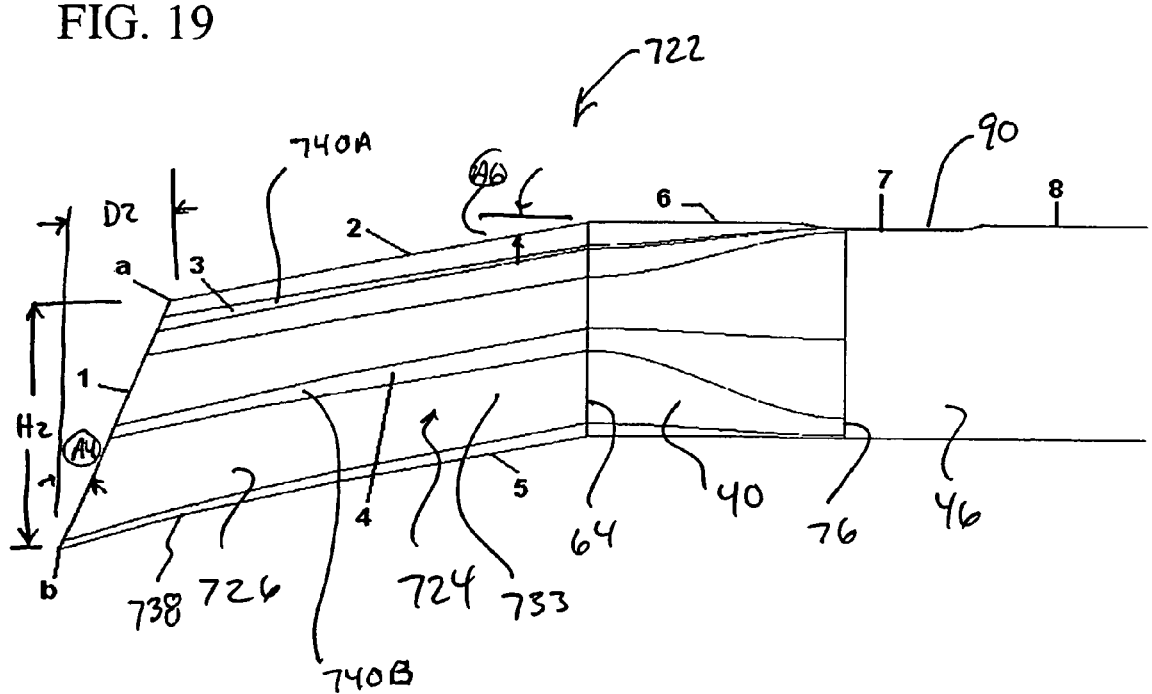
FIG. 19 shows a side elevational view of that which is shown in FIG. 15.

With reference to FIGS. 12, 15 and 19 there is described cutting device 722 under this second embodiment set which is well suited for cutting in quick and efficient fashion through softer cataracts (e.g., non-black and non-brunescent cataracts).

As seen from FIG. 15, for example, cutting device 722 features a tip 724 with modified blade 726 extending off of a transition section 40 similar to that described above for the FIG. 1 embodiment. The height H2 (FIG. 19) of blade 726 is preferably the same as H1 (FIG. 8A) with a range of 0.7 to 2.0 mm being well suited for the preferred usages of the present invention. With reference to FIGS. 15 and 19 there can be seen forward, flat edge 732 having an upper end point 728 and a lower (material contact) point 730. The opposite walls 733 and 734 of blade 726 preferably converge from thicker upper edge 736 to lower edge 738 in similar fashion of the convergence discussion above (both vertically and axially), but with a preferred upper edge thickness at point 728 of about 0.5 mm to 0.9 mm (e.g. 0.7 mm).

As seen forward flat edge 732 is preferably entirely straight between points 728 and 730 and angle A4 (FIG. 19) is preferably in range of 20° to 45° with 30°±5° being preferred. Also the length of flat edge 732 preferably is about 1 to 3 mm as in 2 mm±0.5 mm. Also both the upper end lower edges are preferably rounded off to some degree as in a cross-section upper edge curvature with a radius of about 0.07±0.02 mm and a corresponding corrective in lower edge of about 0.05 mm±0.02 mm.

Upper edge 736 and lower edge 738 preferably extend in parallel fashion with FIG. 19 illustrating a proximal to distal downward slope from the horizontal of angle A6 which preferably is in the range of 15°±5°. Lower edge 738 preferably extends out distally farther than upper edge 736 from common boundary edge 64. For example, the axial distance D2 between the distal most point 728 of upper edge 736 and the distal most point 730 for lower edge 738 is preferably 0.3 mm to 0.4 mm with 0.35 being a preferred value. Thus, edge 738 preferably extends out farther distally by about 15% to 45% of the height H2 of the blade.

FIG. 15 is also features grooves 740A and 740B on blade face 733 and grooves 742A and 742B on opposite face wall 734. Grooves 740A and 742A are shown in the upper position similar to their counterparts in the earlier embodiments, but has some preferred different characteristics including a continuous expanding height along its axial unit (e.g. a 2/1 increase) as in a distal minimum of 0.05 to 0.1 mm and approximately 0.1 to 0.2 mm. Grooves 740A and 742A have a similar depth as the earlier described grooves (e.g., 0.05 mm). Grooves 740B and 742B preferably are a bit shallower than their upper counterpart as in 0.03 mm depth as well as a 2/1 expansion in vertical with or height value such as 0.06 mm to 0.12.

FIG. 16 shows cutting device 822 which is similar in all respects with cutting device 722, but for non-grooved side walls 733' and 734'.

Figure 17:
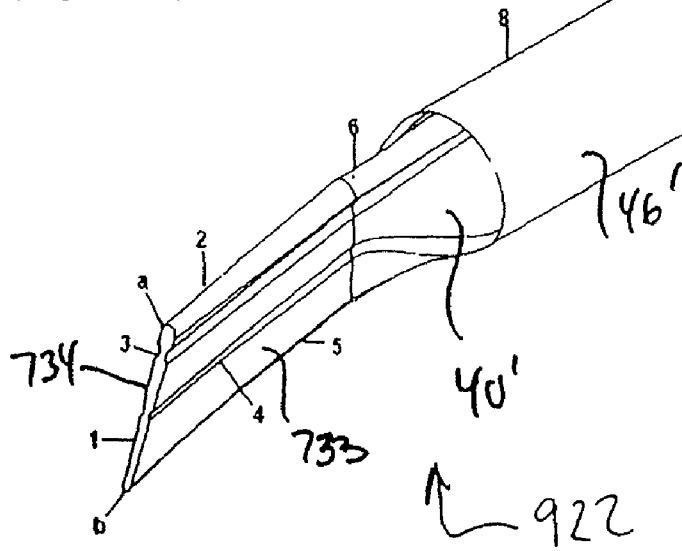
FIG. 17 shows a perspective view of the cutting device shown in FIG. 13

FIG. 17 shows cutting device 922 which is similar in all respects with cutting device 722, but for having a solid transition section 40' and shaft 46'.

Figure 18:
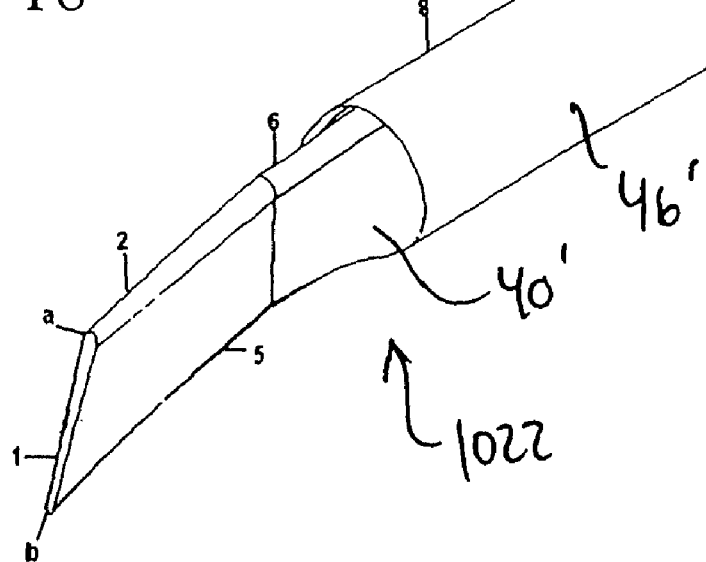
FIG. 18 shows a modified embodiment of the cutting device shown in FIG. 17 but with the FIG. 18 embodiment being free of grooved side walls.

FIG. 18 shows cutting device 1022 which is similar in all respects with cutting device 922, but for having non-grooved side walls as in cutting device 822.

Figure 20:
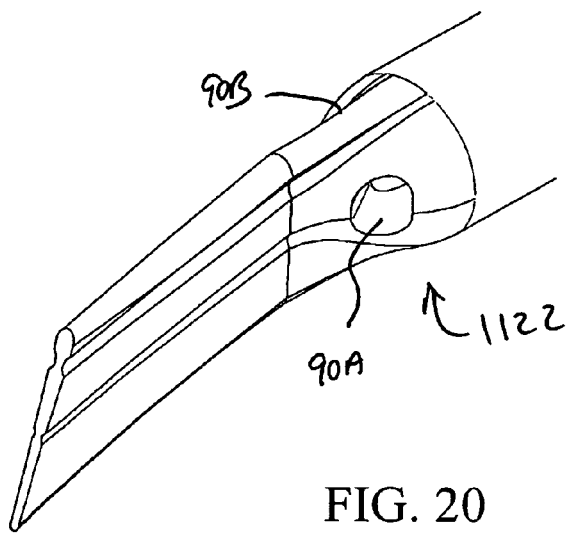
FIG. 20 shows an alternate embodiment of the cutting device with side aspiration ports in place of the upper edge aspiration port shown in FIG. 15 with FIG. 20 being inclusive of side wall grooves.

FIG. 20 shows cutting device 1122 which is similar in all respects with cutting device 722, but for having aspiration parts 90A and 90B in the side walls of transition section 40 as opposed to the superior, upper edge position in cutting device 722.

Figure 21:
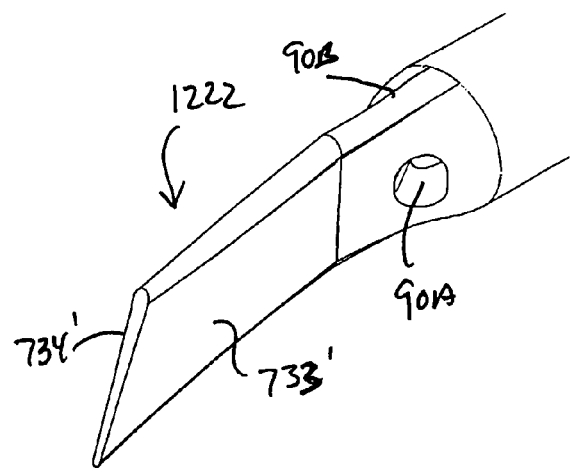
FIG. 21 shows a view similar to FIG. 20 but for an embodiment free of side wall grooves.

FIG. 21 shows cutting device 1222 which is similar in all respects to cutting device 1122, but for its non-grooved side walls 733' and 734'.

Figure 22:
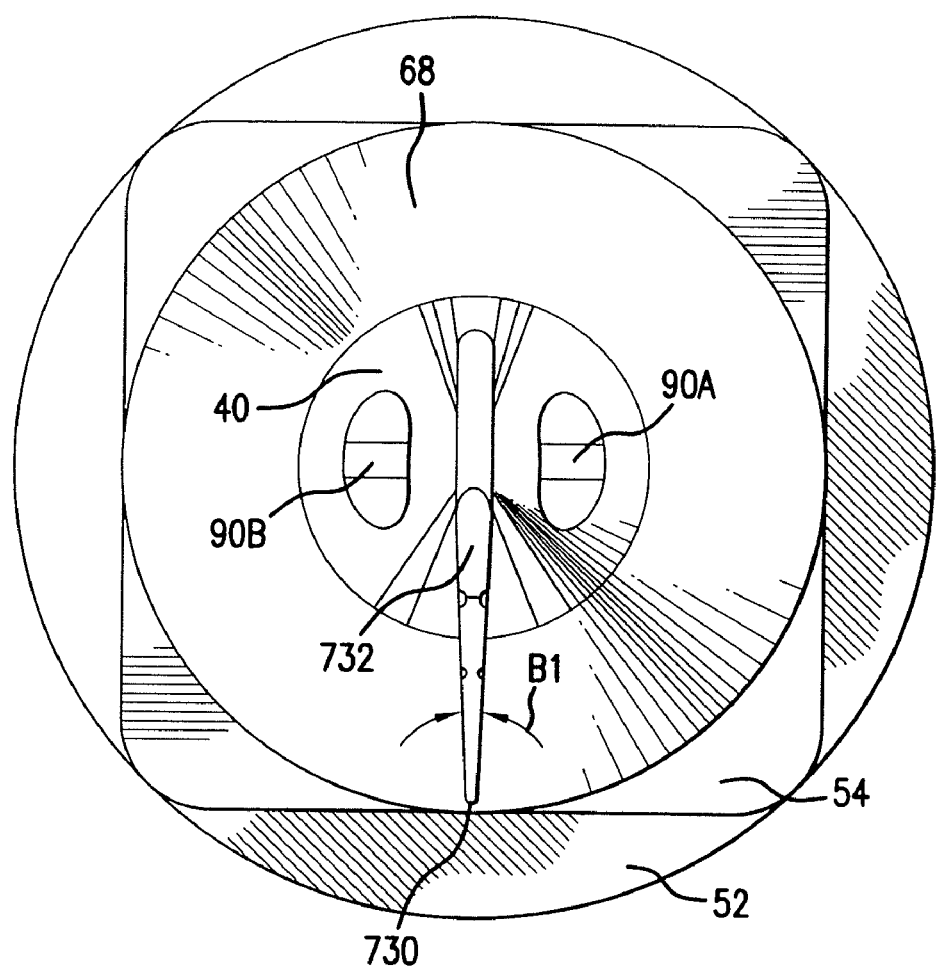
FIG. 22 shows a front view of the cutting device shown in FIG. 20.
Figure 24:
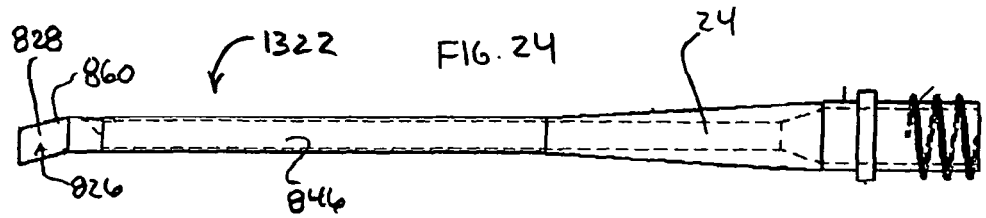
FIG. 24 shows a side elevational view of that which is shown in FIG. 23.

FIG. 22 shows a front elevational view of that which is shown in FIG. 20 including aspiration ports 90A and 90B.

FIGS. 23 to 26 illustrate another embodiment of a cutting device for use in cutting and fragmetizing a wide variety of cataract types, which is referenced 1322 in the figures. Cutting device 1322 has a similar ultrasonic transmission section 24 forming a support base for a modified shape tip 826. In the embodiment illustrated in FIGS. 23 to 26 transmission section 24 comprises hollow shaft 846 with lumen 870, although, as in the other embodiments above, the subject matter of the present invention also includes a solid shaft embodiment. Tip 826 comprises transition section 840T with aspiration port 890 and blade 828. Exterior conical section 830 is provided in shaft 846 and is preferably about 8 mm in length with an inclination relative to the horizontal of about 3 to 5° as in 3.6° with a diameter on the most proximal end of about 2 mm. Also the illustrated cylindrical tube 840 is preferably about 14 mm in length and 1 mm in exterior diameter. Within tube 840 and extending through the remainder of transmission section 24 is provided suction conduit or aspiration passageway 870 which has a length of about 19.8 mm and a diameter along the tube 840 of about 0.8 mm in a preferred embodiment. Conic passageway section 880 is formed in the transition area for conical section 830 and the proximal connection end 848 having a cylindrical fluid passageway 850 leading to the open end at the proximal most end 827 of cutting device 1322. Conic passageway section 880 preferably has a length of about 1.27 mm and an angle of 18.4 degrees relative to the horizontal, while cylindrical fluid passageway preferably has a length of about 4.65 mm and a diameter of about 1.6 mm or double the diameter of lumen 870.

Figure 25:
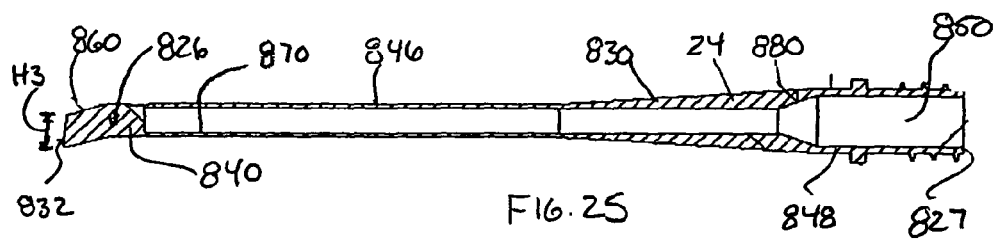
FIG. 25 shows a vertical bi-sect of that which is shown in FIG. 24.
Figure 25A:
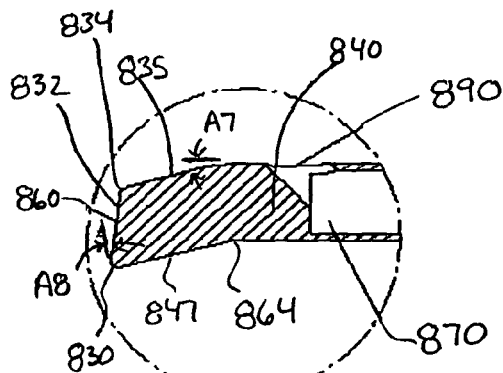
FIG. 25A shows an enlarged view of the circled portion of FIG. 25.

The flattened blade 828 is shown to be a solid end portion of the monolithic common material cutting device 1322 (e.g., formed of a suitable surgical material as in titanium or surgical steel). As with the other embodiments, upper edge 835 of blade 828 preferably slopes down from the upper edge of the transition section 840T with a preferred angle A7 of about 15 degrees +/−5 degrees and preferably has a height of about 1 mm +/−0.3 mm. Blade 828 has a longer length inferior edge 847 extending from boundary line 864 between blade 828 and transition section 840T (transition section preferably being a more converging step down portion of the cutting device and the blade section preferably having a lesser convergence (as in a convergence angle difference ratio of at least 5/1) or no axial convergence so as to demarcate the transition section's distal boundary 864. The lower inferior edge 847 slopes down to the distal most point represented by the center point in the rounded corner edge 830E. As shown superior forward surface edge 832 extends proximally back in superior fashion up to upper rounded end 834 (the center point of that curved edge being the highest point relative to the height H3 measurement). The rounded corners 830E and 834 preferably have a radius of 2 mm. In addition, the edging represented by 835 (top edge), 847 (bottom edge) and 832 (forward edge) also preferably is rounded of in a cross sectional plane that has a transverse intersection with the respective edge's line of extension. Also, as seen in FIG. 25A the forward edge 832 has a slope angle of about 20 to 40° and more preferably about 30° as represented by angle A8. This results in upper edge being shorter in longitudinal length as compared to lower edge 847 also extending from common boundary line 864 and preferably at a common angle so the upper and lower edges are parallel, with the difference in length between the upper and lower edges preferably being about 0.25 mm to 0.5 mm and more preferably about 0.35+/−0.1 mm for this embodiment.

Figure 26:
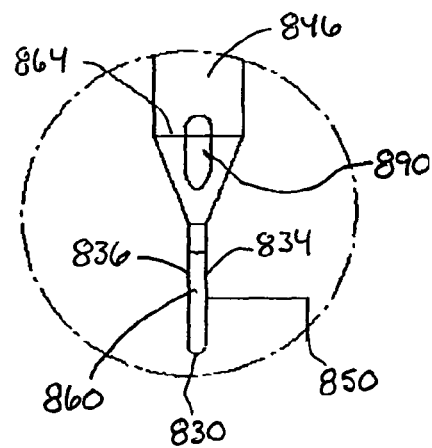
FIG. 26 shows a superior plan view of distal region of the cutter device shown in FIG. 24.
Figure 23:
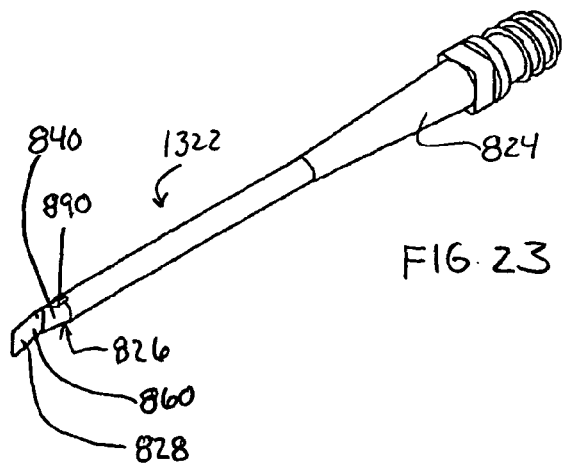
FIG. 23 shows a perspective view of a third embodiment of the present invention.

As best seen in FIG. 26, aspiration port 890 is formed in a superior location in transition section and extends into hollow shaft 840. The aspiration port 890 has similar exterior boundary dimensions as described above for aspiration port 90 and, in this embodiment, the elongated aspiration port has a majority of its length falling on the transition side and a minority of its length on the shaft side of boundary line 864. Aspiration port 890 is also located about 25 mm from the proximal end 827 of cutting device 1322. The subject matter of the present invention also includes a cutting device such as cutting device 1322 but with side aspiration porting instead of or in addition to the superior positioned port 890 shown.

In the above described embodiments, the flattened blade of the respective tips is shown to slope down (e.g. a curved and/or straight surface sloping) from a shorter axial length upper edge to a longer axial length bottom edge with the latter designed for initial material contact at least at its distal most region. Between the two distal most points of the upper and lower edges is provided a forward facing edge that preferably defines an angle of 30 degrees+/−10 degrees. This forward edge can include a straight line forward edge section or an entirely curved forward edge (which can also represent part of a continuously curved edge back to the boundary with the transition section) or a combination of the same. This configuration for the forward edge and associated upper and lower edging is considered beneficial in obtaining the benefit of a blade design that can create a deep and long enough cut in a cataract while avoiding contact with the distal edge of the anterior capsule. With the forward edge arrangement, the lower edge is also preferably thinner than the upper edge thus representing the sharper of the two edges. Also with this blade design, the first portion of the knife which contacts the cataract is the inferior sharp edge with an axial length difference of 0.5 mm between the inferior edge and the superior edge being preferred as it permits that the knife to advance in a manner that avoids causing damage to the iris or the anterior capsule edge when moving forward, since the lower edge protrudes farther than the upper edge. An additional safety feature is found in an embodiment of the invention where there is formed a concave recess such as one in the shape of an arch, with this arrangement there is provided a blade configuration that helps prevent undesirably contact with the iris or the anterior capsule when the tip is moved backward during its cutting motion. Moreover, some of the above described embodiment have side wall grooves that assist in diminishing friction when the blade penetrates the nucleus of the cataract, and helps in dissipating the ultrasonic energy in the lateral sites, where it is not useful.

The present invention also includes alternate embodiments which have the grooving but are free of aspirating porting as well as embodiments that are both groove less and free of aspiration porting. For example, when using the tips without aspiration holes the debris originated form the cataract cutting leaves the anterior chamber of the eye through the one or more incisions formed, which incisions are arranged to have some amount of fluid (and debris) outflow.

When dealing with a cutting device used in conjunction with a fluid flow irrigation system, the shaft is preferably covered in 360 degrees by a silicone sleeve, which preferably is sized so as not to cover the flattened portion. Through an annular space formed between the sleeve and the shaft fluid circulates, which circulating fluid cools the tip and can be made to enter the eye through two holes located laterally in the sleeve. The supplied fluid also replaces fluid that is being withdrawn from the eye either via the aspiration holes and through the lumen of the device or which leave the eye through the incisions or any combination of the same. The sleeve is of a length that preferably covers up to the transition of the shaft (if present) and the flattened portion, so as to cover up the aspiration hole or holes. If the sleeve is not in this position there is the potential for, when the surgeon moves the tip backwards to replace it, the irrigation holes of the sleeve to be positioned outside the eye which can cause anterior chamber collapse.

The described tips herein may be used without an irrigation sleeve as in by themselves, through their insertion through so called micro incisions (e.g., less than 1.5 mm as in a 1.1 mm incision), preferably while supplying irrigation by means of a second instrument entered through an auxiliary incision.

Figure 27A:
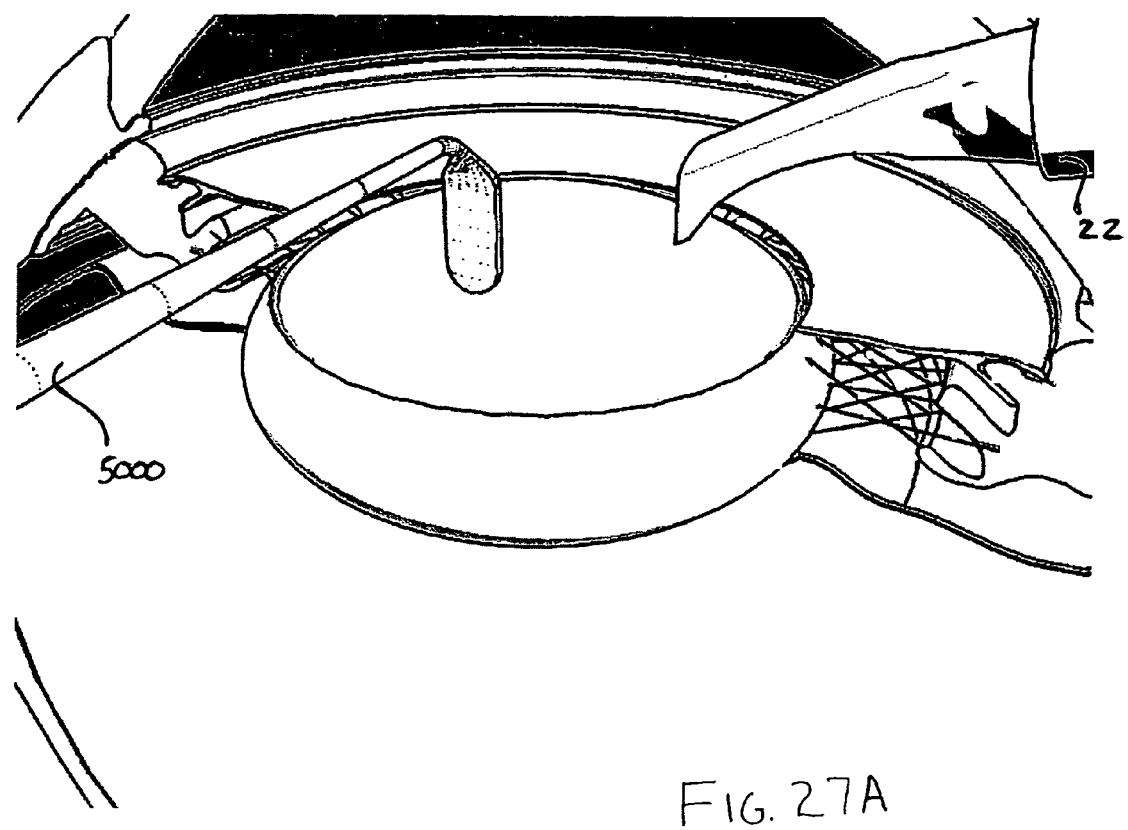
FIGS. 27A to 27Q show a preferred sequence for cutting a cataract with the cutting device of FIG. 1 with a supplemental flat tip fragmentation facilitator tool.
Figure 27B:
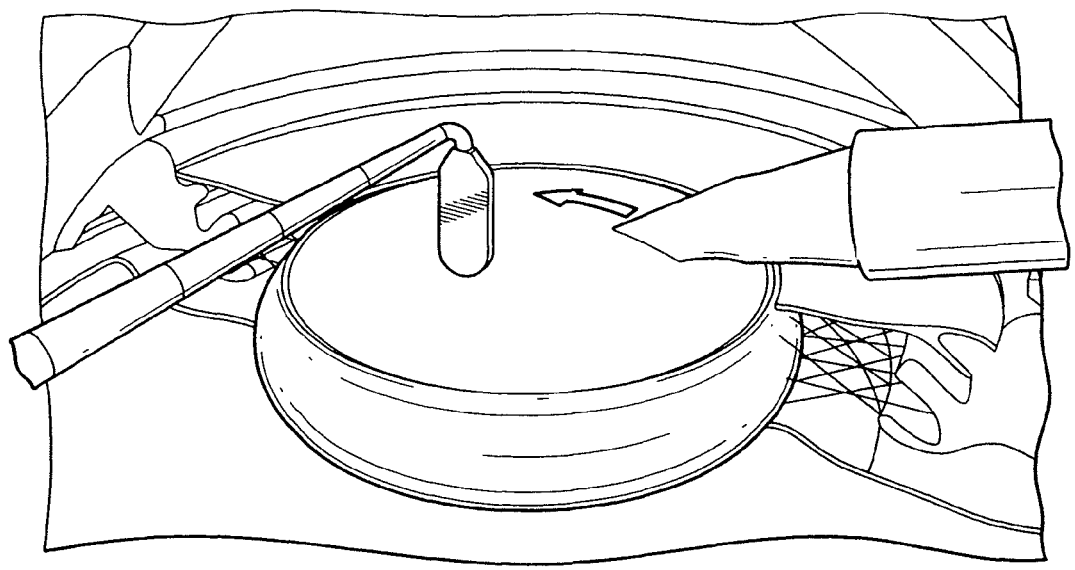
Figure 27C:
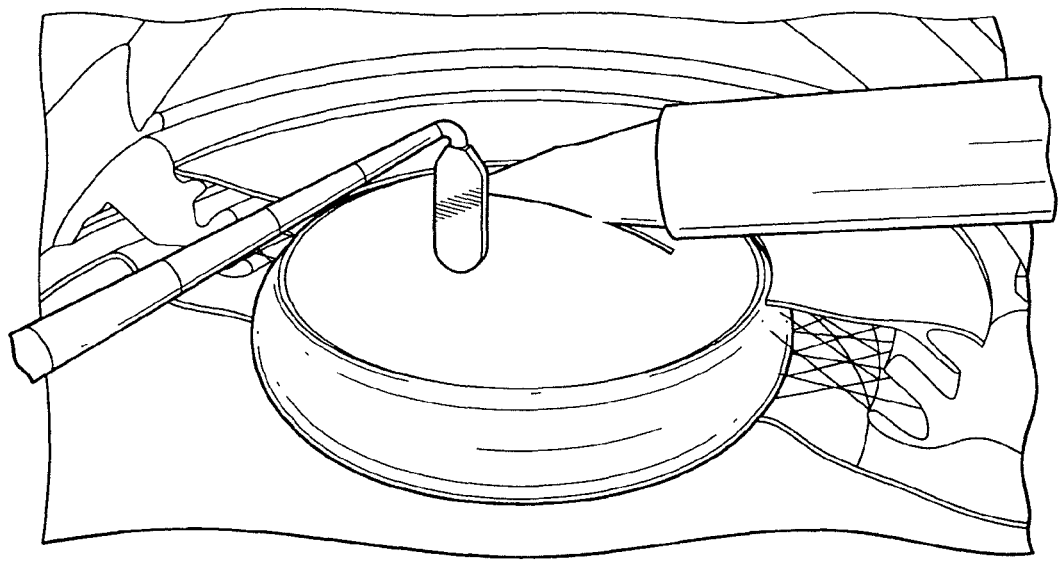
Figure 27D:
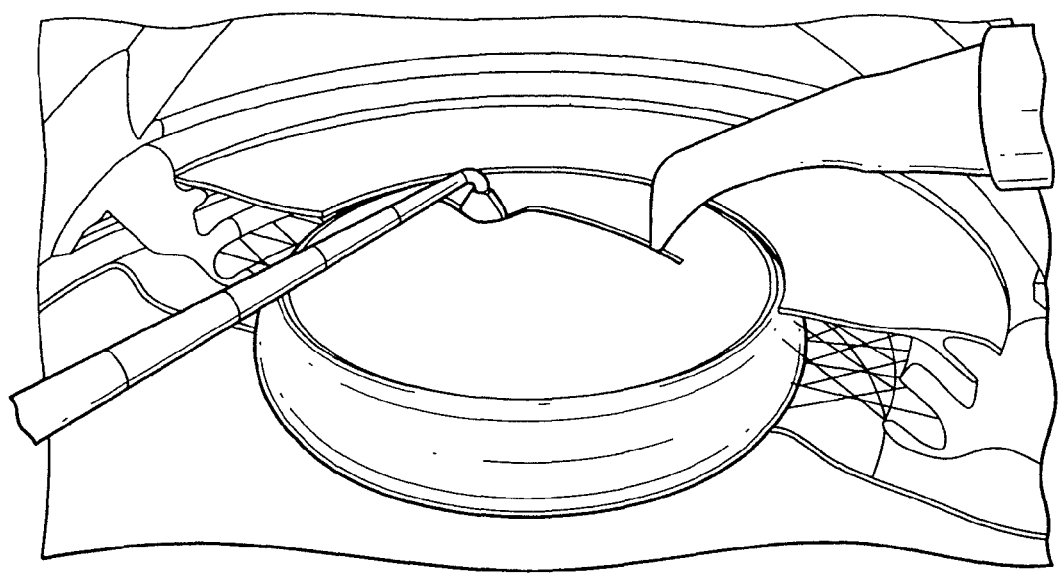
Figure 27E:
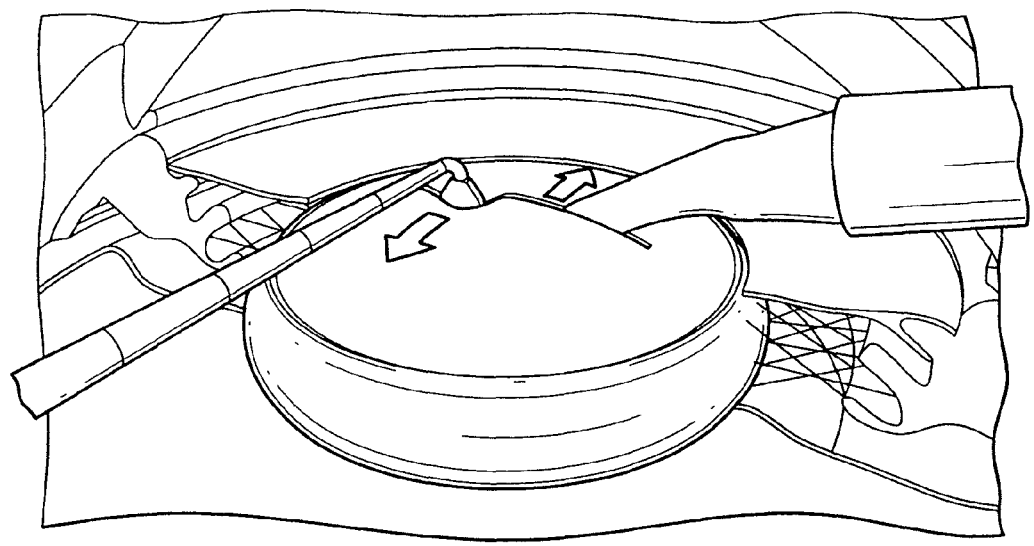
Figure 27F:
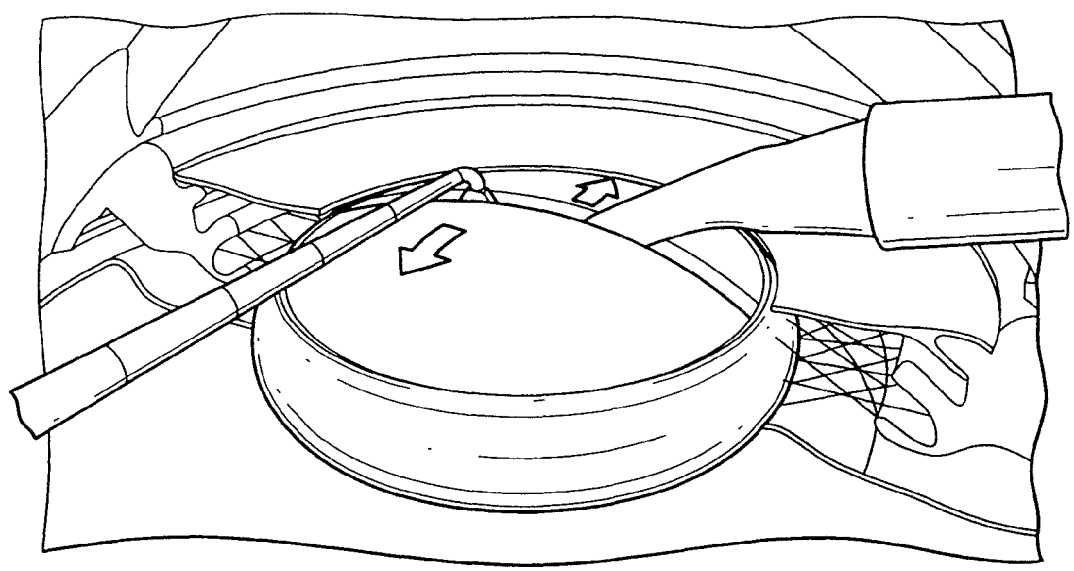

As an example of an operational application of a cutting device under the present invention reference is made to FIGS. 27A to 31. As shown in FIG. 27A, the cutting device of the present invention is entered though the main incision and a second instrument (fragmentation facilitator) through an auxiliary incision. Following capsulorhexis and hydrodissection, the tip of the ultrasonic knife 22 is introduced inside the anterior chamber and made to vibrate between 28,000 and 40,000 Hz (according to the handpiece to which it is connected as seen from FIG. 28B). When placed in contact with the material of the cataract the ultrasonic energy at the tip causes a shock wave that generates a sharp cut, similar in quality and ease to the cut produced by a hot knife in butter or chocolate. This cut through the cataract material is represented in FIGS. 27B and 27C. The ultrasonic movement of the tip may be longitudinal in a given extension, but the tip of the ultrasonic knife may also have an oscillatory lateral movement, depending on the type of phacoemulsifier used. Frequency of this oscillation may be sonic (100 Hz) or ultrasonic (32,000 Hz), according to the program used in the equipment. Amplitude of this oscillation may be, for example, up to 10 degrees (e.g., 3 to 10 degrees). An example of this oscillatory movement provided by a drive means associated with the handpiece can be seen in FIGS. 32 and 32A to 32C which show the blade of the cutting device oscillating to opposite sides of a superior to inferior bi-section plane of the blade on which line K lies. The blade is caused to oscillate at an angle X to line K in a direction transverse to the noted bi-section plane. Thus the angle X is preferably 3 to 10 degrees or 6 to 20 degrees (angle XR in FIG. 32) in total travel on the plane transverse to the noted bi-section plane.

Figure 28A:
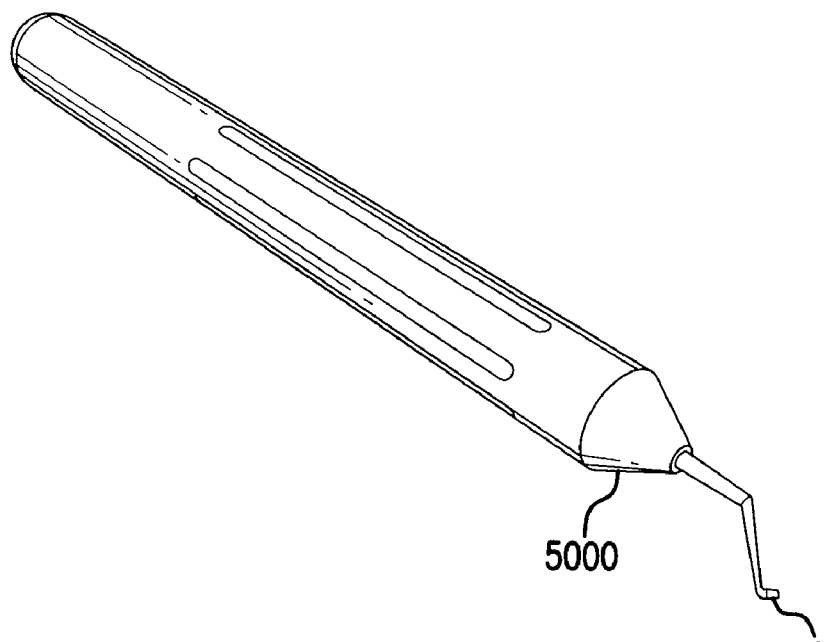
FIGS. 28A to 28C show a set of supplemental tools (fragmentation facilitator tool (FIG. 28A), microspoon tool (FIG. 28B), and nucleus sustainer tool (FIG. 28C)) which can be used, individually, alternatively alone or in the possible groupings and sub-groupings, in conjunction with the cutting device of the present invention.
Figure 28B:
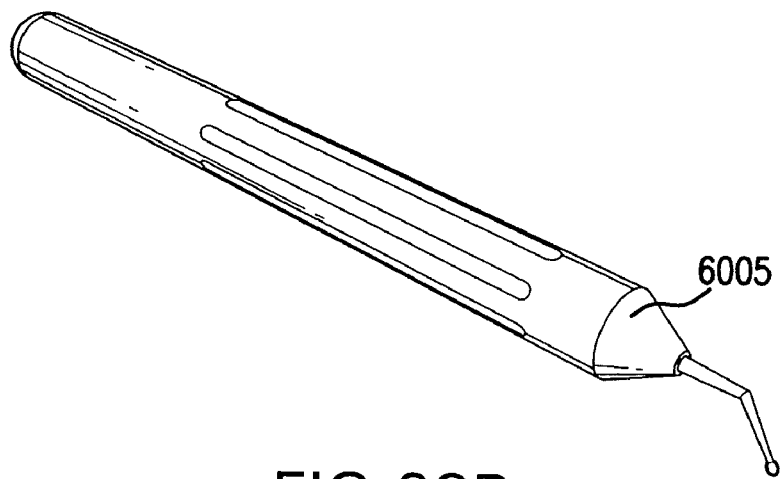
Figure 28C:
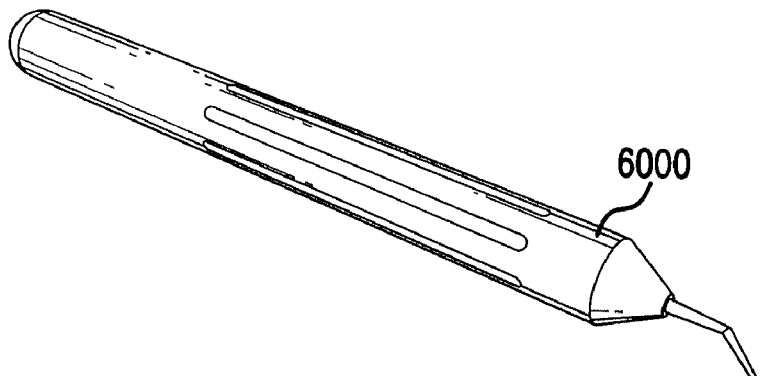
Figure 29:
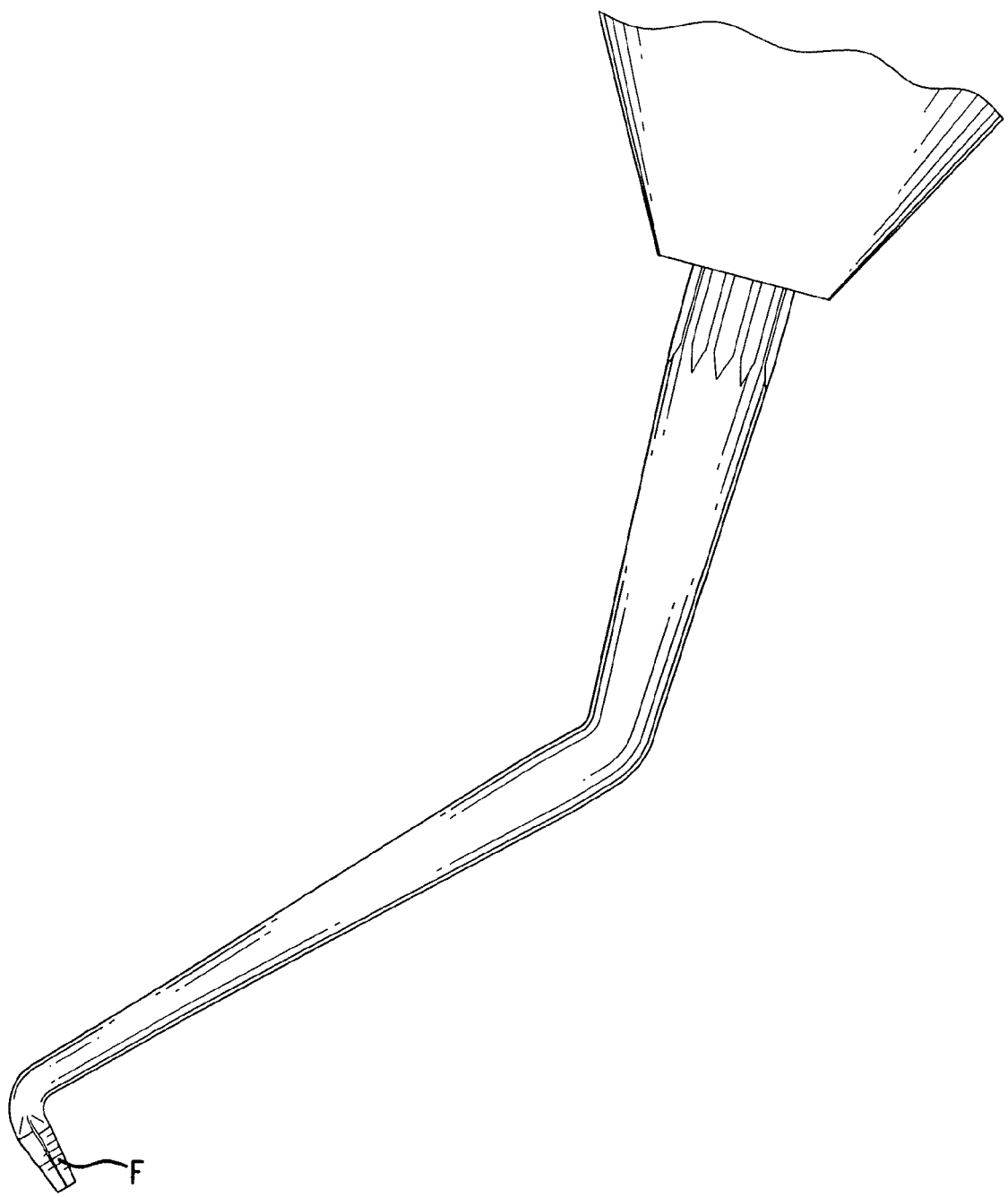
FIG. 29 shows a closer view of the fragmentation facilitator tool shown in the FIG. 28 set.
Figure 30:
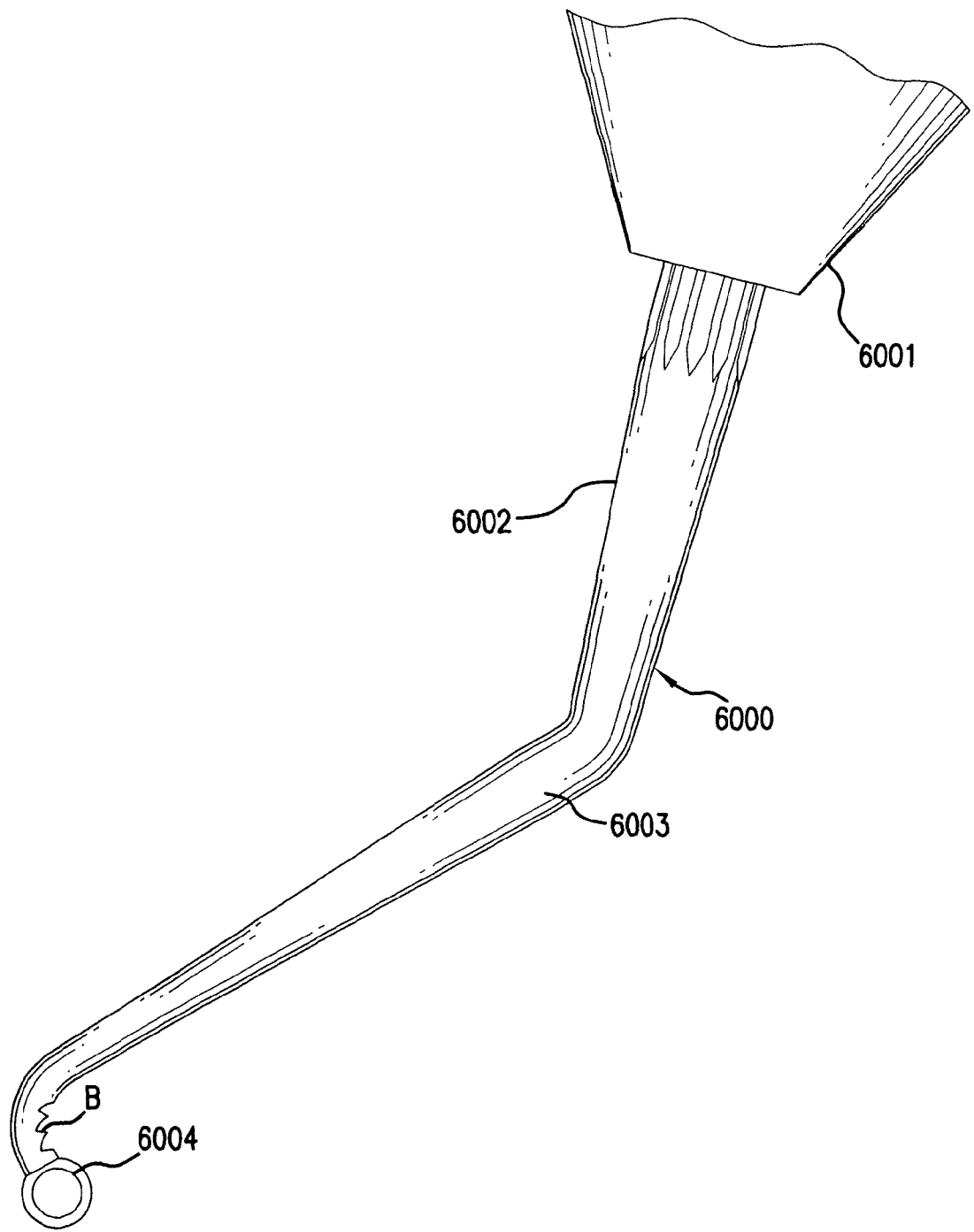
FIG. 30 shows a closer view of the nucleus sustainer tool shown in the FIG. 28 set.

Although not represented in The FIGS. 27 to 31, when using a cooling irrigation system, upon entering the tip inside the eye the irrigation system is activated. For example, and when the tip makes contact with the cataract the surgeon activates the means for generating the ultrasonic movement in the tip as in pressing a foot pedal of a phacoemulsifier to "position 3" common on many phacoemulsifier instruments, so that electric energy is applied to the handpiece and this causes it to originate the vibrating motion and activates the irrigation at the same time. With these instruments the amount of excursion of the vibratory movement of the tip, which determines the "power" of ultrasonic or sonic energy applied to the cataract, is related directly with the amount of electric energy supplied to the handpiece, and in turn it depends on the setting chosen by the surgeon as in the excursion of the foot pedal to position 3. In this way the surgeon can modulate this power, i.e. length or amplitude of each stroke of motion of the tip, according with the hardness of the cataract, changing the parameters of energy in the console of the phacoemulsifier typically between 60 and 100% of power of energy (related with a percentage of the total displacement of the tip in each stroke). The surgeon also preferably keeps activated the irrigation system if being used in conjunction with the activation of the ultrasonic vibration. For example, the position 3 of the foot pedal also keeps activated the irrigation and aspiration of fluid. The cut using the ultrachopper through the cataract material is preferably carried out to a depth of, for example, a 3.0 to 3.5 mm depth (60 to 80% of the cataract thickness), while preferably reaching a length of about 2.5 and 3.5 mm, without surpassing the edge of the anterior capsulorhexis to avoid damaging it. As shown in FIG. 27D and FIG. 29 "fragmentation facilitator" instrument 5000 presents a flattened end, which flattened end is introduced into the anterior chamber through the auxiliary incision, which is preferably located 90 to 100 degrees apart from the main incision line and is inserted into the groove formed by the cutting device. In a preferred embodiment, instrument 5000 has at its distal end, an angled prolongation at 90 degrees with length of 1.5 to 2.0 mm, which is introduced inside the cuts generated by the ultrasonic knife, and using the instrument and the knife, there is applied a small amount of opposite pressure on the walls of the cut, which helps in the ease of separation of the fragments as represented in FIGS. 27D, 27E and 27F. The flattened end can take on a variety of shapes with a goal being to provide the flattened end of a thickness that is readily insertable into the initial groove formed by cutting device 22 or the like (e.g., can be sharp edged or have more rounded oval shape contour as shown in FIG. 27A plus).

Figure 27G:
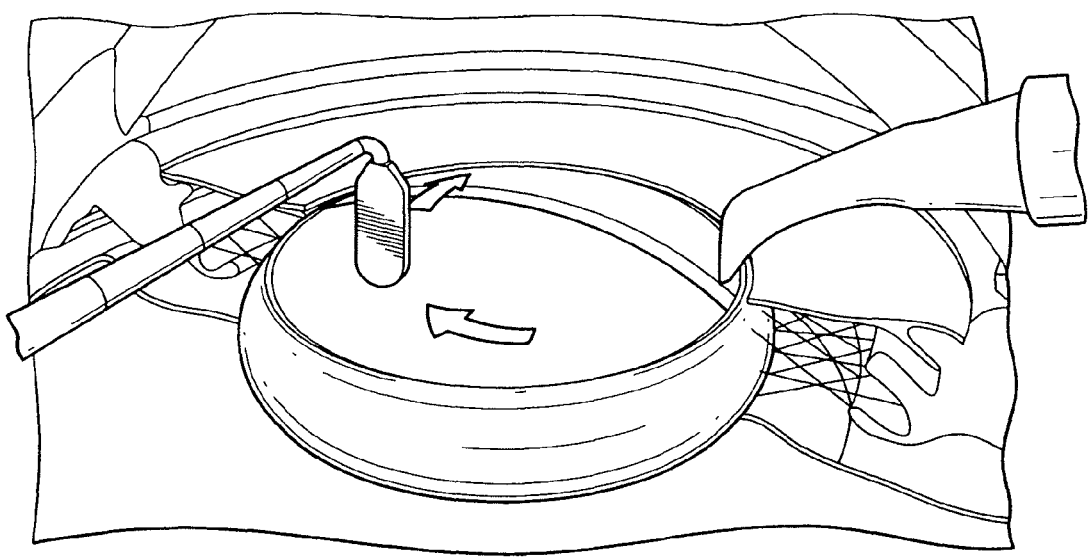
Figure 27H:
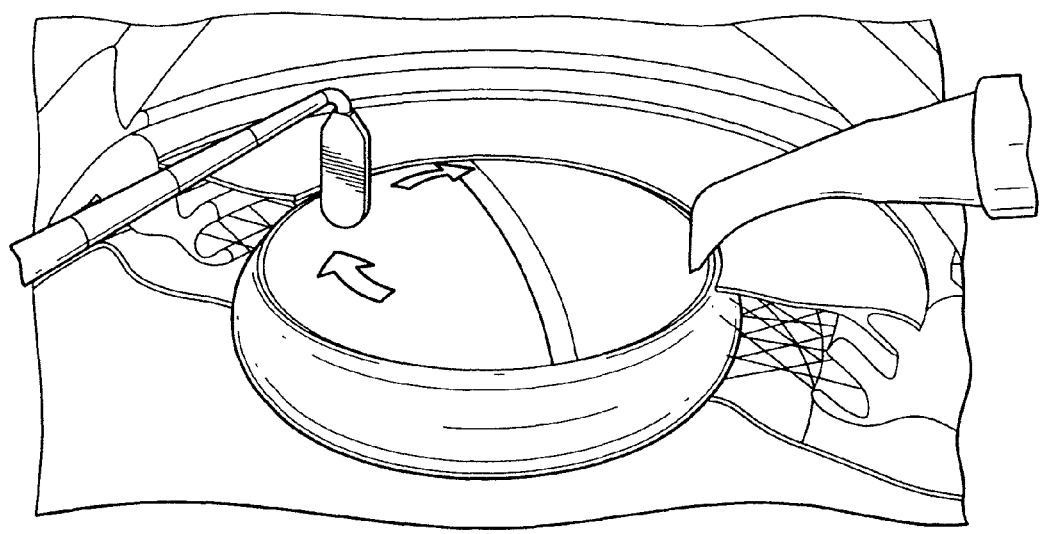
Figure 27I:
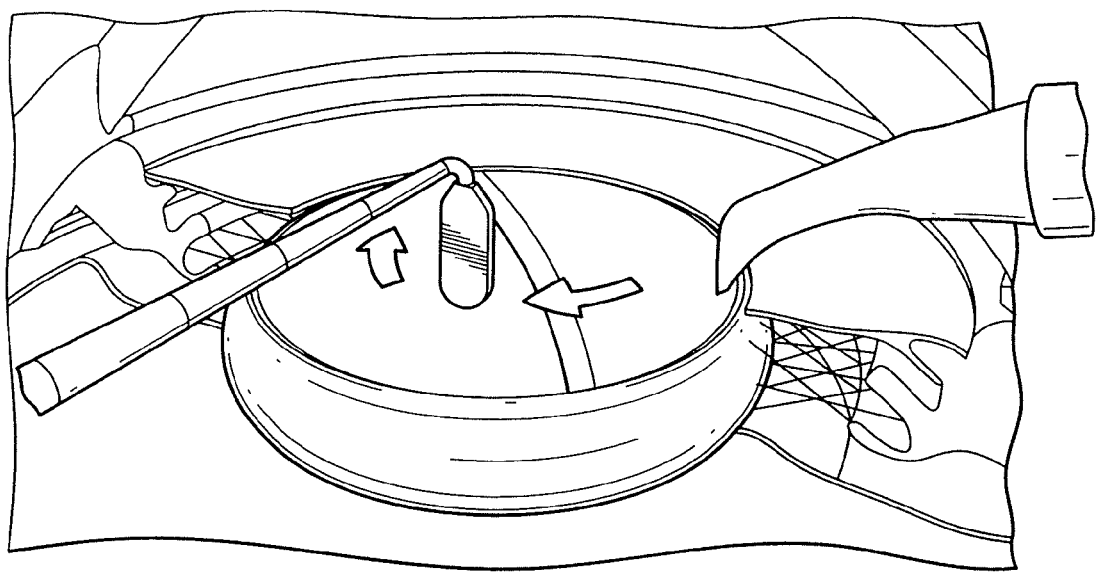
Figure 27J:
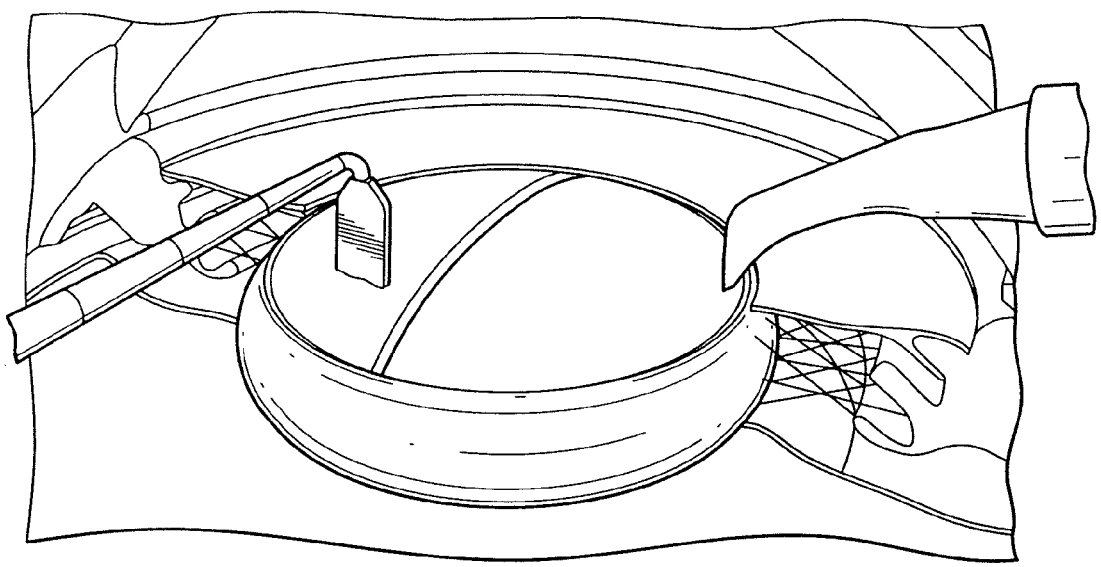
Figure 27K:
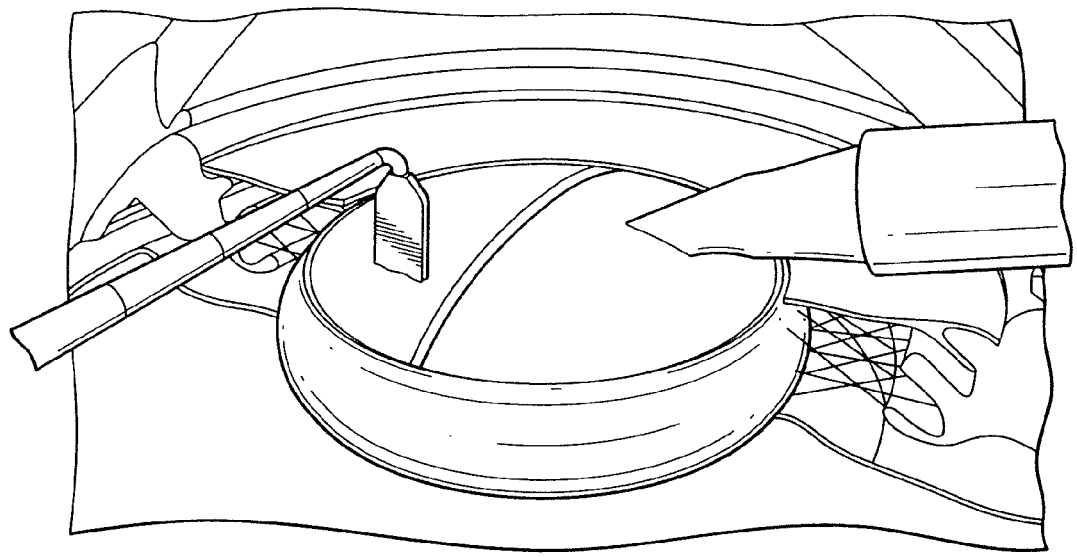
Figure 27L:
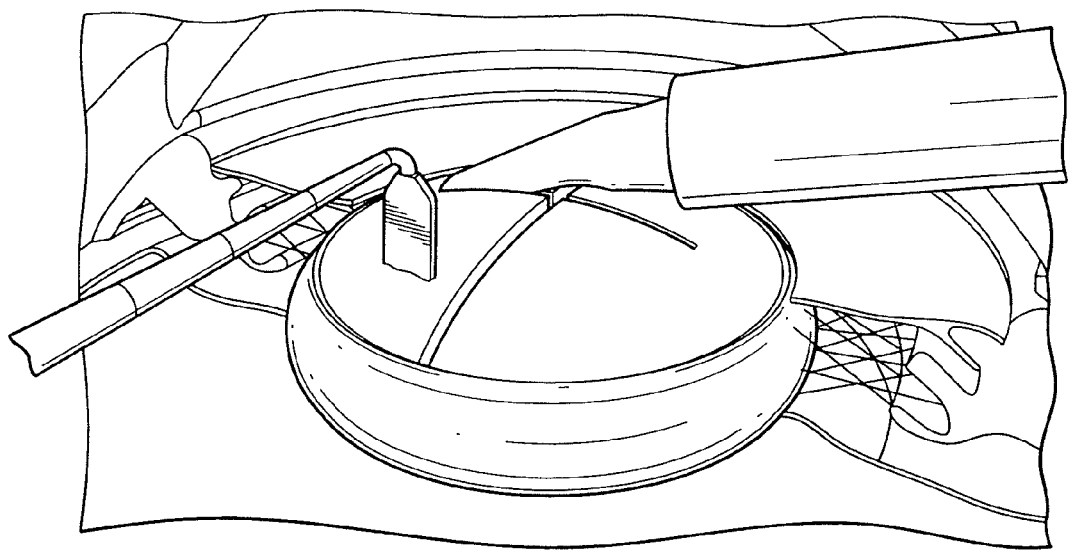
Figure 27M:
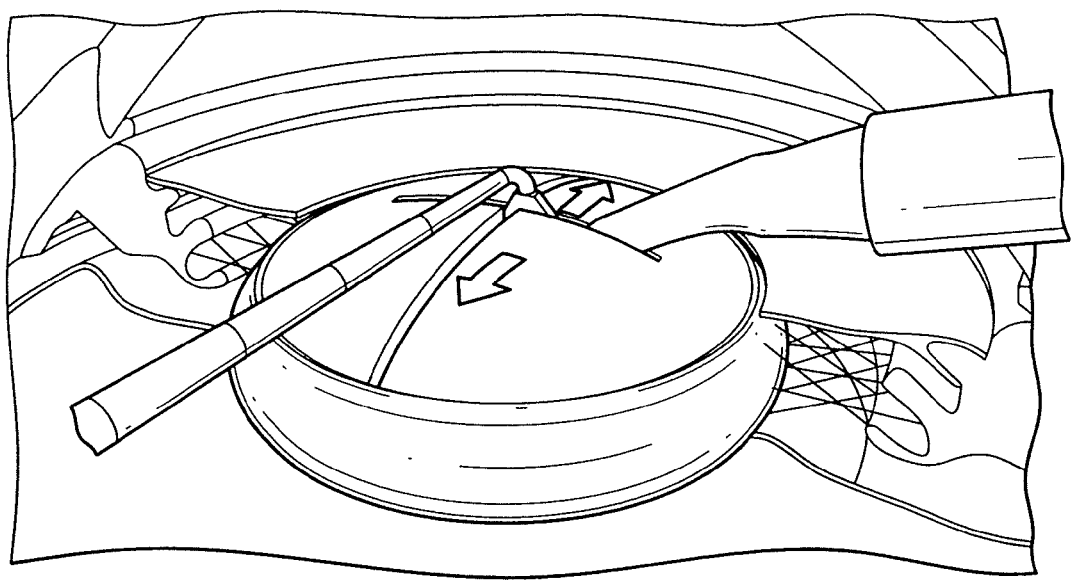
Figure 27N:
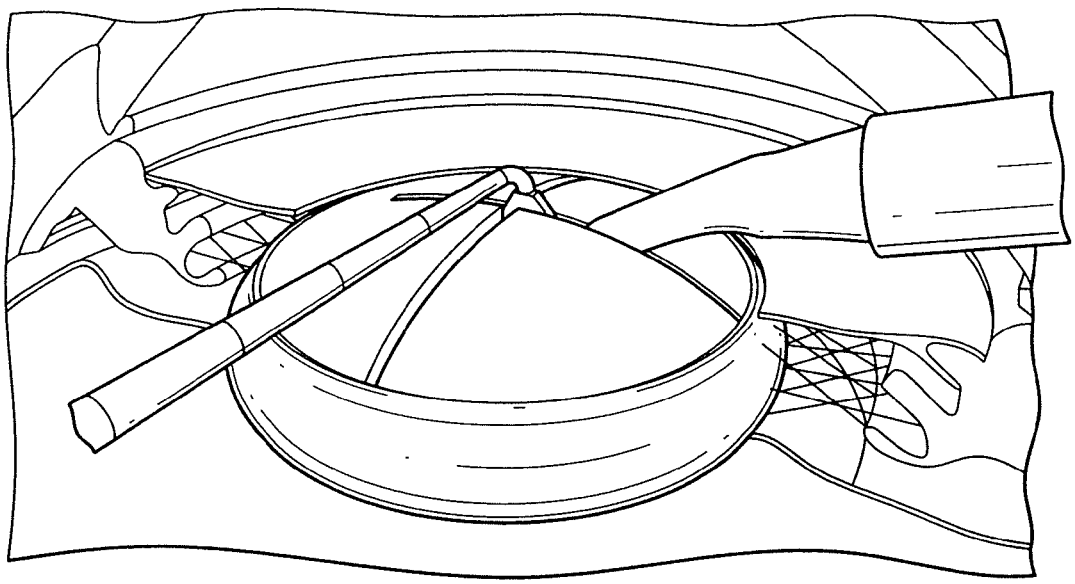
Figure 27O:
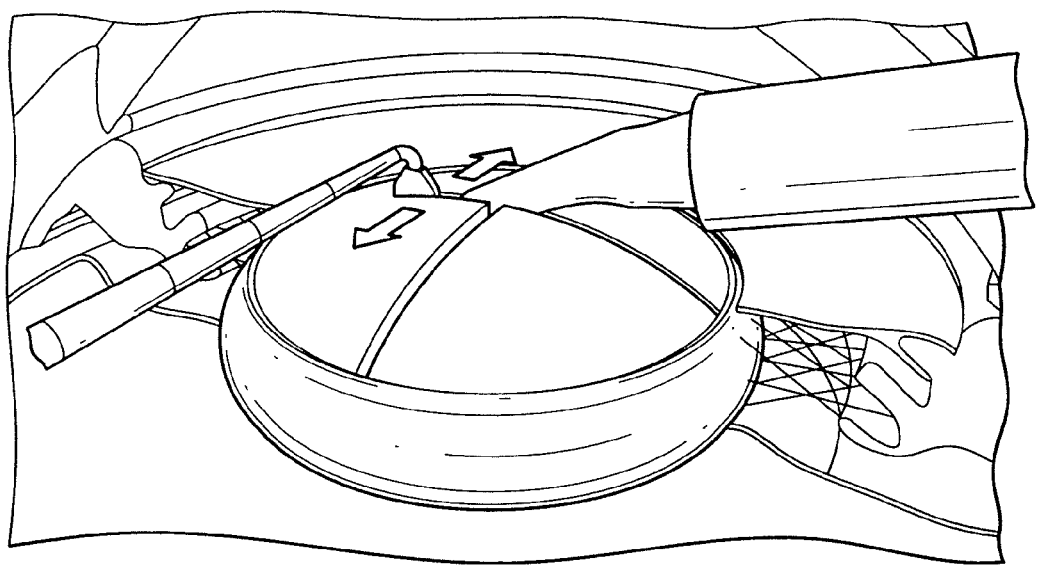
Figure 27P:
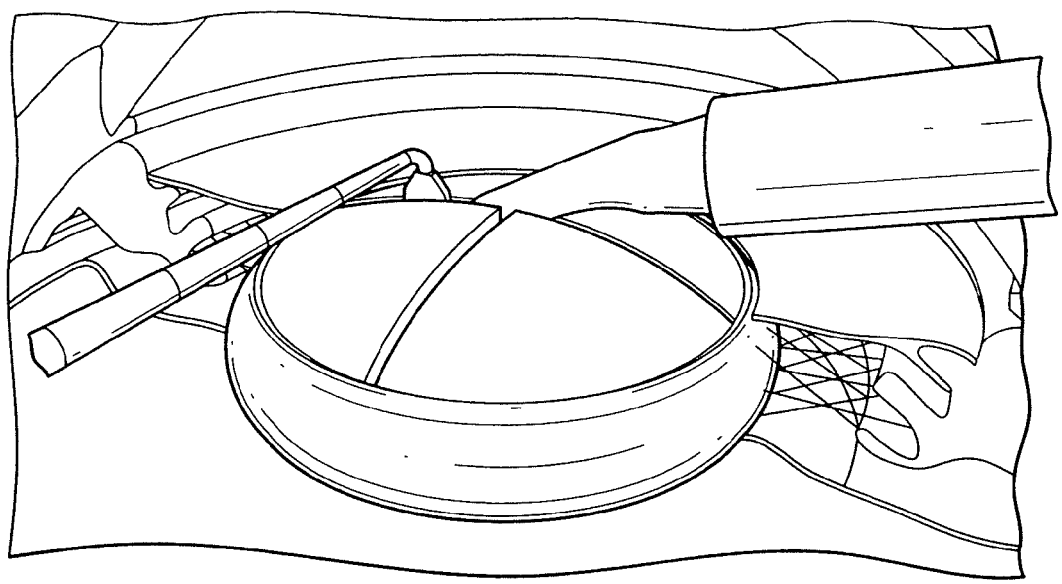
Figure 27Q:
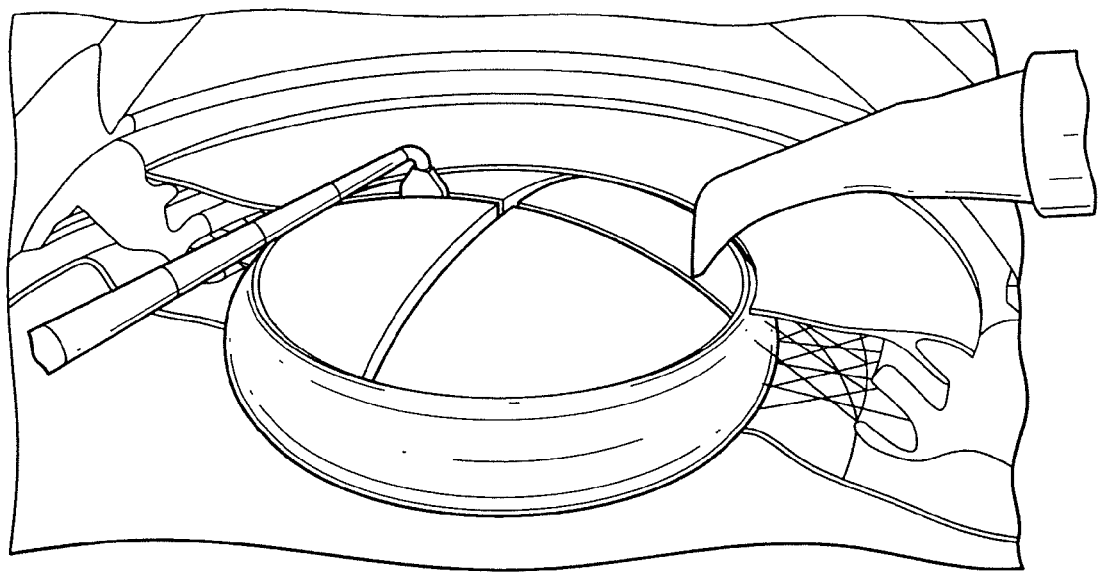

FIG. 27G illustrates the removal of instruction 5000 from the expanded groove and it use to facilitate rotation. That, is, the whole cataract is rotated as shown in FIGS. 27H and 27I until the desired reorientation for the next cut (the new cuts are made in accordance with the discretion of the surgeon as to the number and size which typically involves cuts made in pizza cut fashion to render the desired number of generally similarly sized fragments that can be best handled by a further fragmentizing aspiration device as in a vibrating suction needle). For example, the rotation may be of 20 to 45 degrees, according to the number of fragments that the surgeon wants to create (between 4 and 12). FIG. 27J, illustrates a rotation of 45° to line up for the second cut to be formed. Using this technique the time used to divide the cataract is usually between 8 and 20 seconds. FIGS. 27K to 27Q illustrate a similar sequence carried out as used in the first cut and separation formation. As seen instrument 5000 is positioned to one side or the other of the pervious made cut(s) and is used with the cutting device to further separate apart the material to the opposite sides of the current cut, this further separation (both the initial cut and subsequent cuts) can be simplified with the divergent longitudinal shape of the blade and/or lateral oscillation which each help to increase the groove width being formed initially during the cutting shown in the FIG. 27.

When the fragments are separated the ultrachopper is disengaged there is preferably then connected to the handpiece a standard ultrasonic needle to emulsify the smaller fragments. The use of the ultrachopper before the emulsification of the smaller and manipulatable pieces saves a lot of surgical time and ultrasonic energy. Another alternative, especially useful in hard and very hard (brunescent and black) cataracts, is dividing the cataract using the ultrachopper together with a nucleus sustainer 6000 shown in FIGS. 28C and 30 and in use in FIGS. 33A to 33F. This sustainer is preferably introduced through the auxiliary incision, inside the bag, up to the equator of the crystalline lens, and is used to stabilize the cataract and exert some counter traction to the motion of the ultrachopper as seen in FIG. 33A to 33F. While the ultrachopper penetrates the nucleus to perform the cut, 80 to 90% of the cataract depth, in the way described previously, the nucleus sustainer lifts the cataract nucleus (e.g., 0.5 to 1 mm) as shown in FIGS. 33C to 33F. When the ultrachopper approximates to the nucleus sustainer, both can be moved in opposite lateral directions, to separate the pieces. As seen from the foregoing discussion, the ultrachopper works as a cutting device but also as a micro dissecting spatula moving apart the fragments (as it can in the other embodiments). When using the nucleus sustainer the time of ultrasound energy applied is usually only 3 to 5 seconds. Again, fragments obtained are emulsified using a standard ultrasonic needle.

Figure 31:
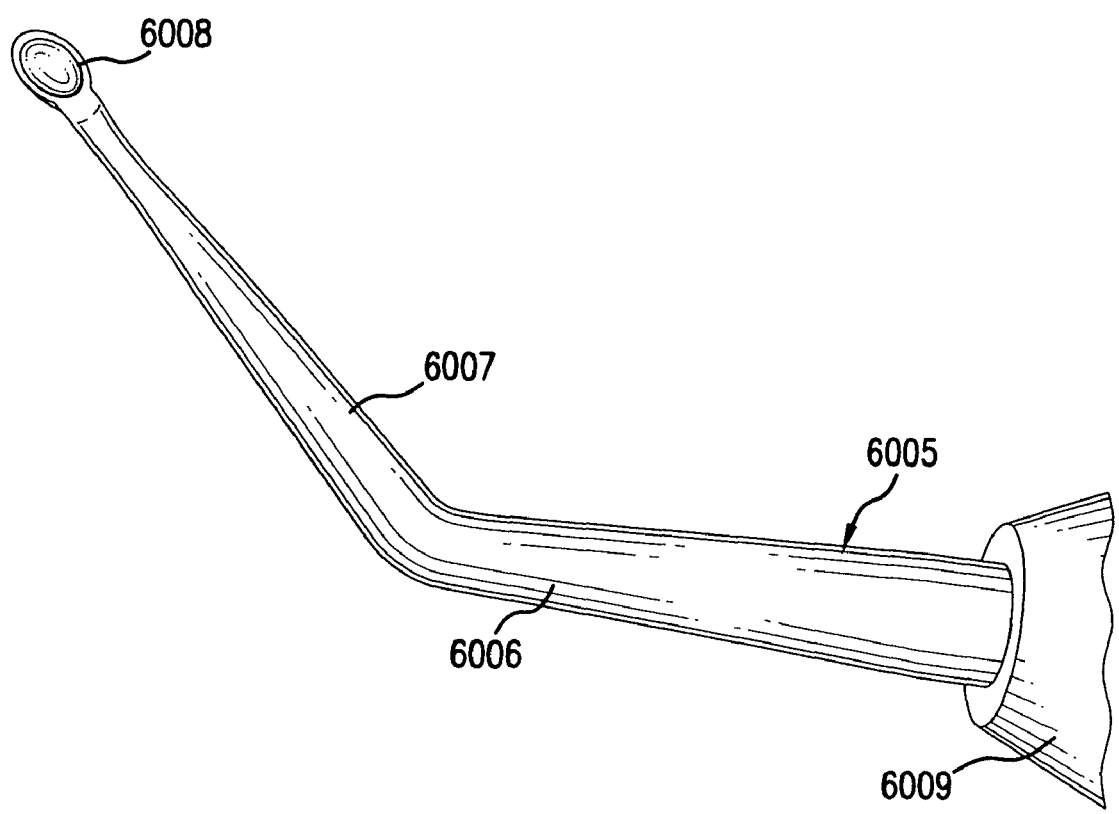
FIG. 31 shows a closer view of the microspoon tool shown in the FIG. 28 set.
Figure 32:
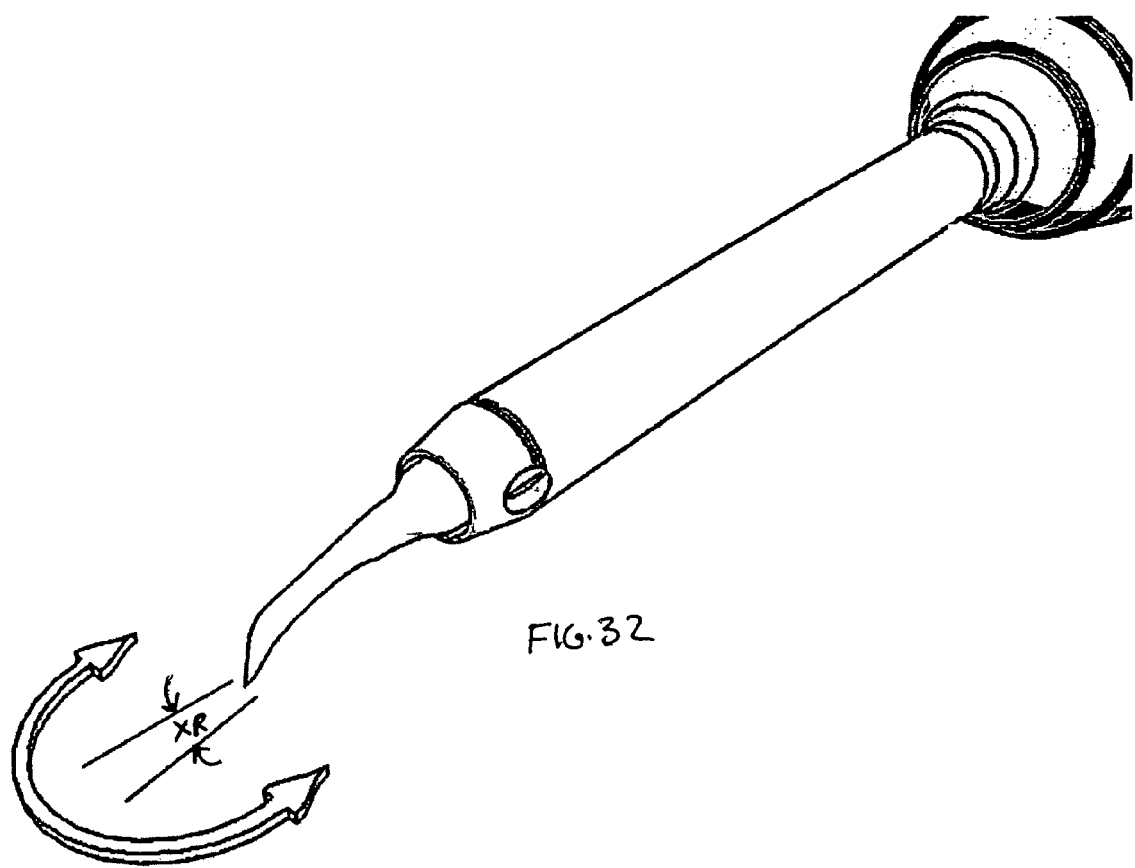
FIGS. 32 and 32A to 32C show the cutting device of FIG. 10 and its movement when connected to a driving means that provides an oscillating motion in a direction transverse to a superior to inferior bi-section of the blade.
Figure 32A:
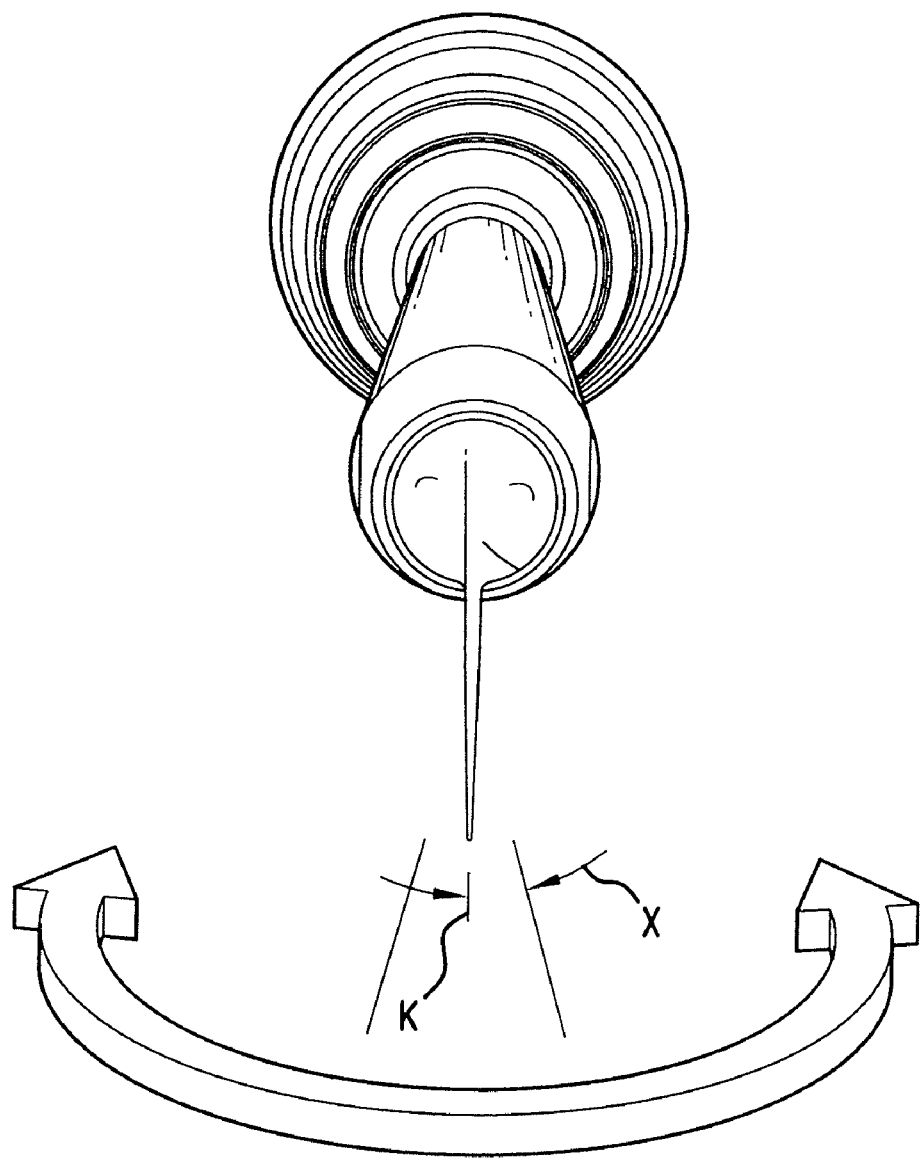
Figure 32B:
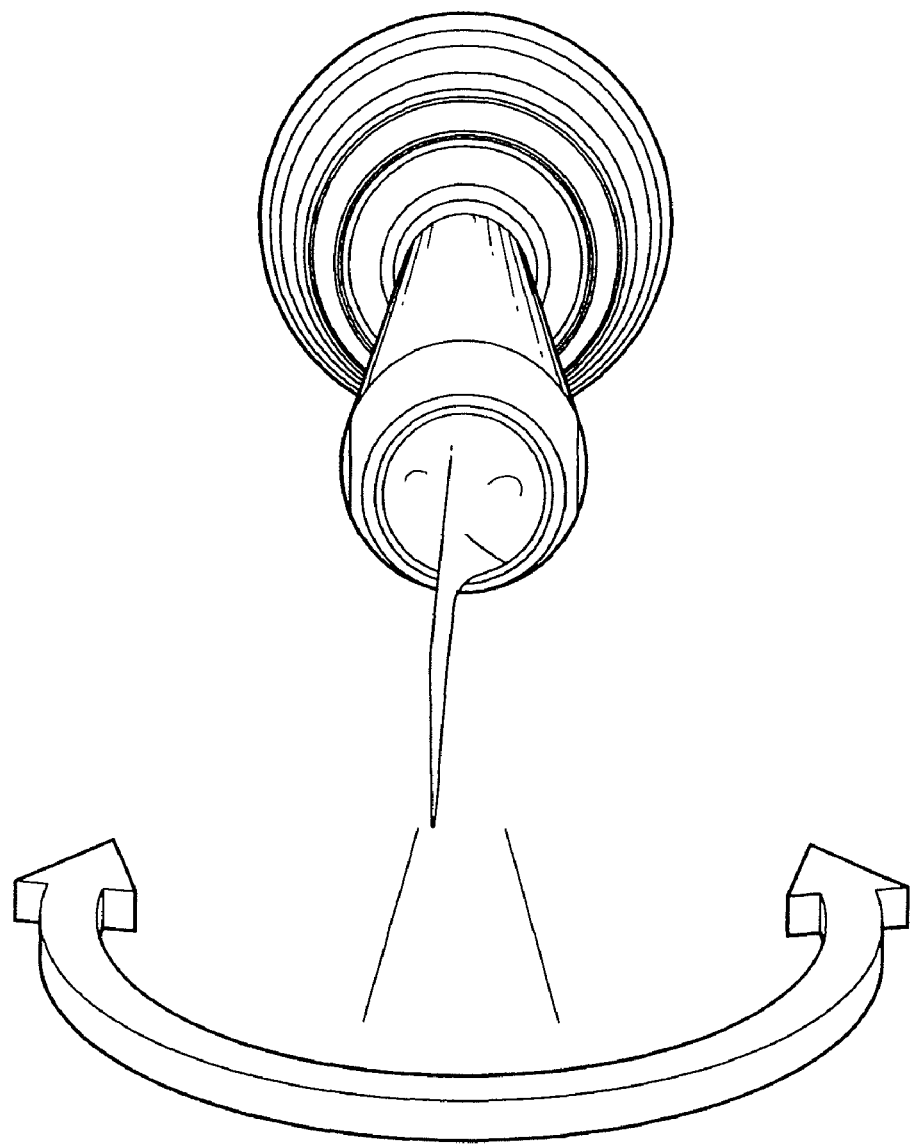
Figure 32C:
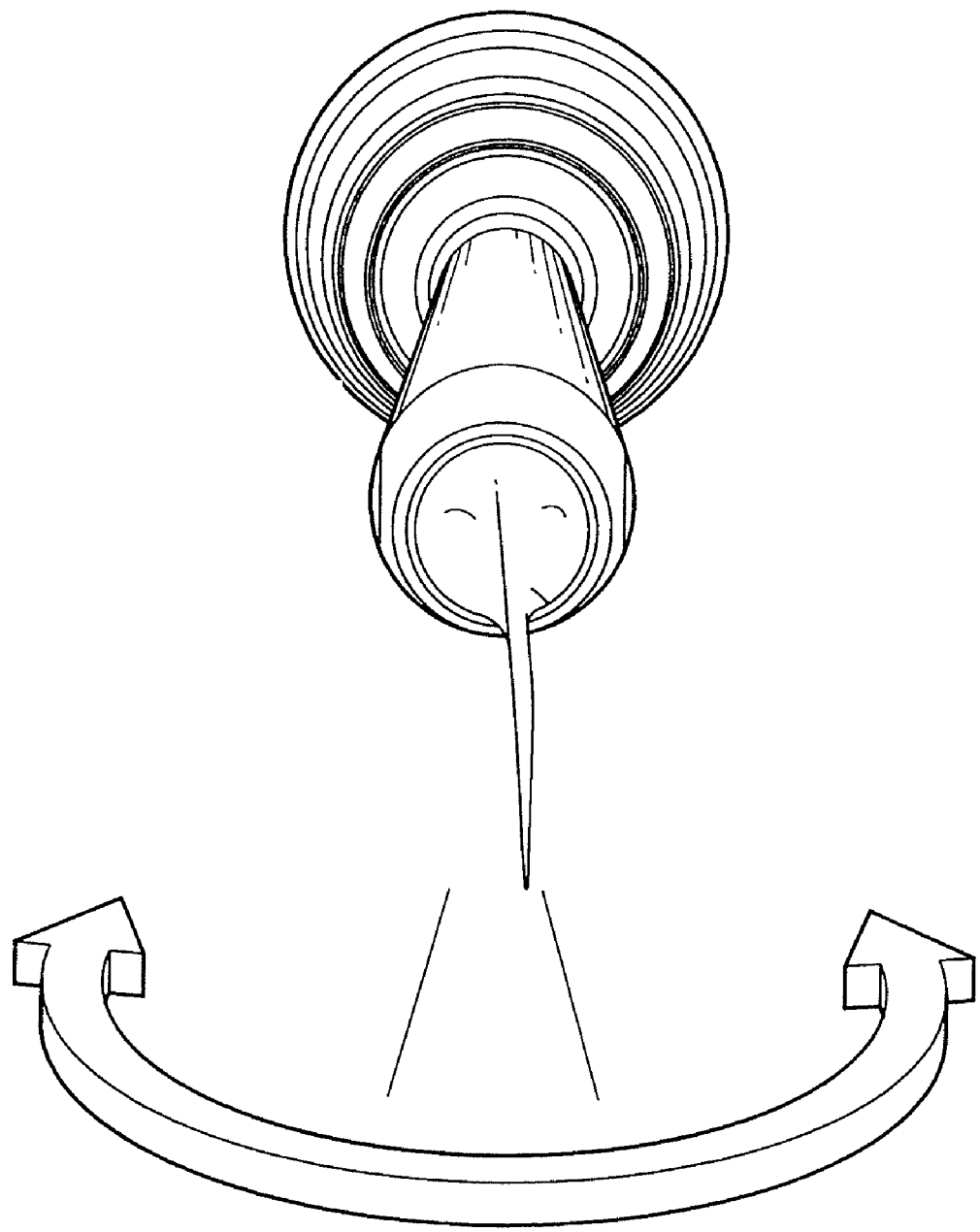
Figure 33A:
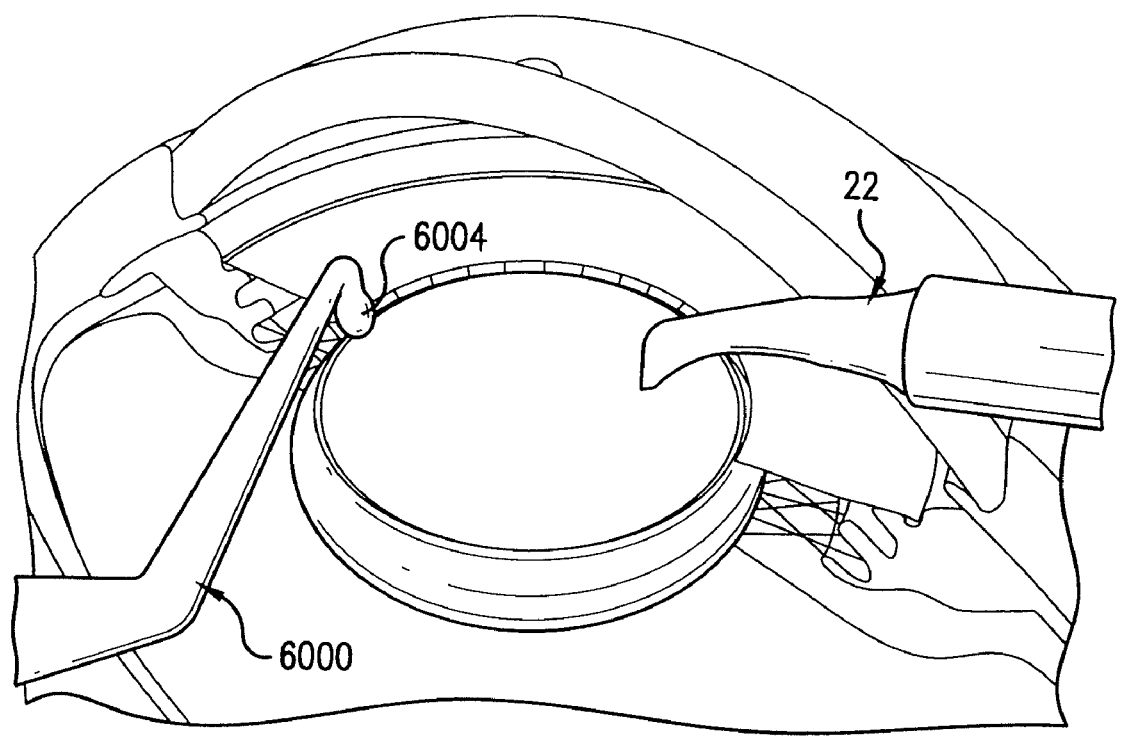
FIGS. 33A to 33F show a preferred sequence for cataract cutting using the cutting device of FIG. 1 with a supplemental nucleus sustainer tool.
Figure 33B:
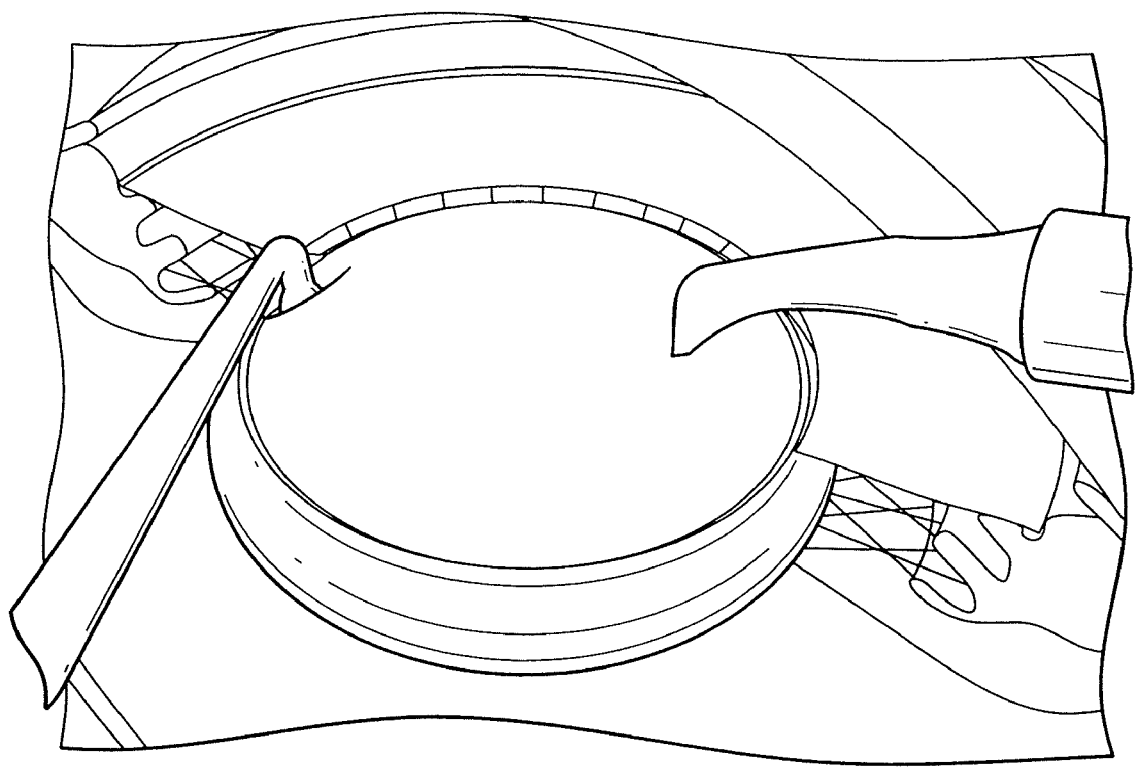
Figure 33C:
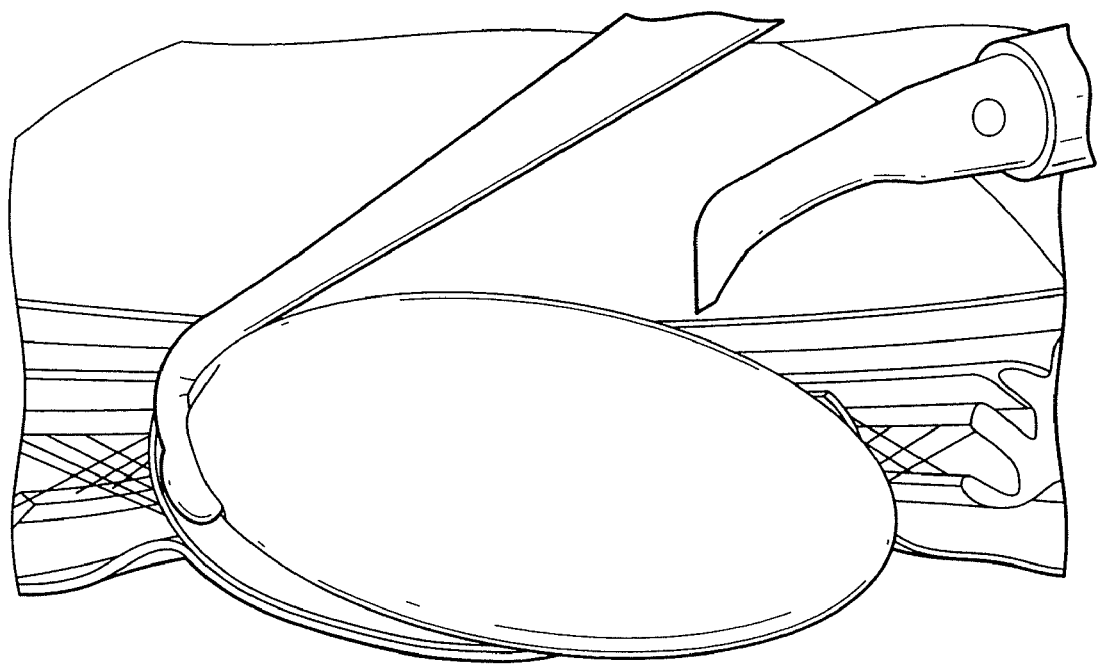
Figure 33D:
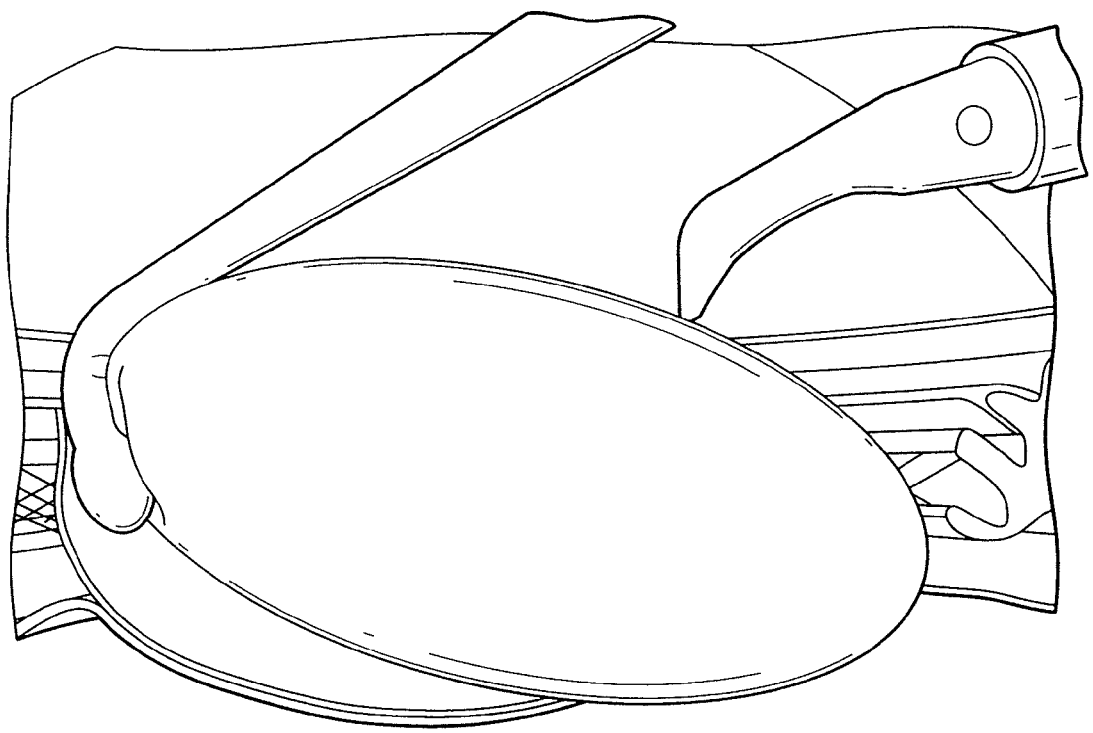
Figure 33E:
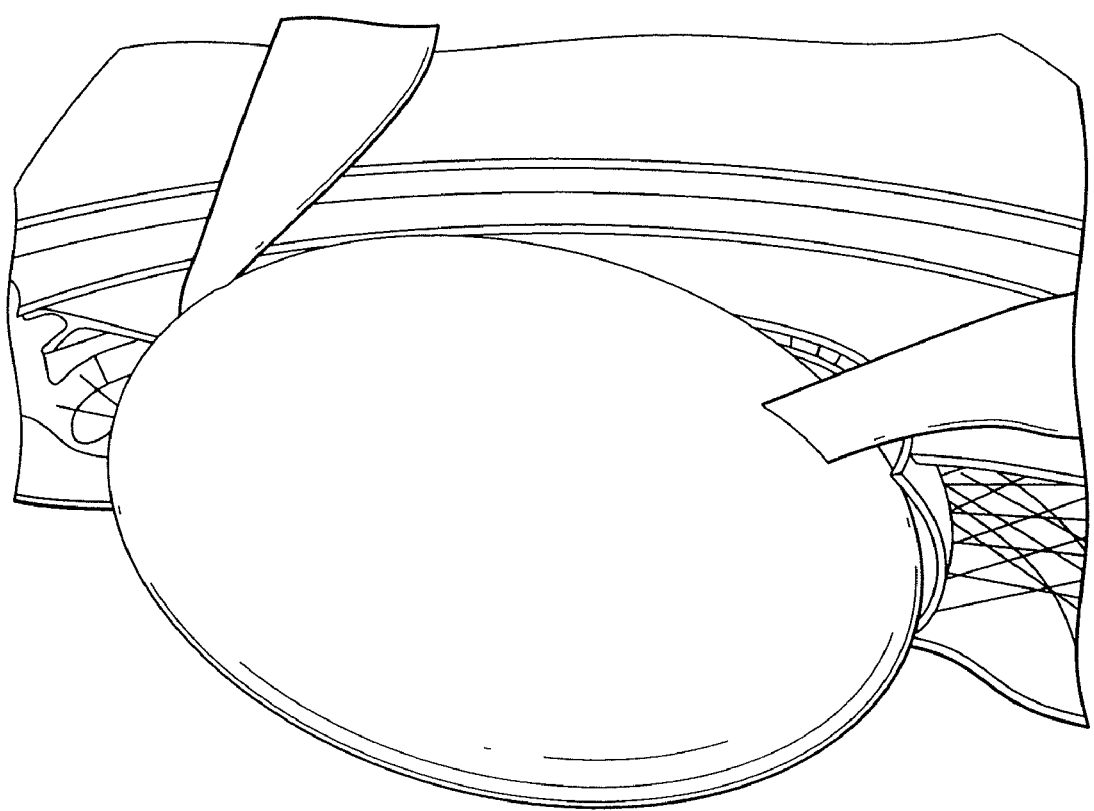
Figure 33F:
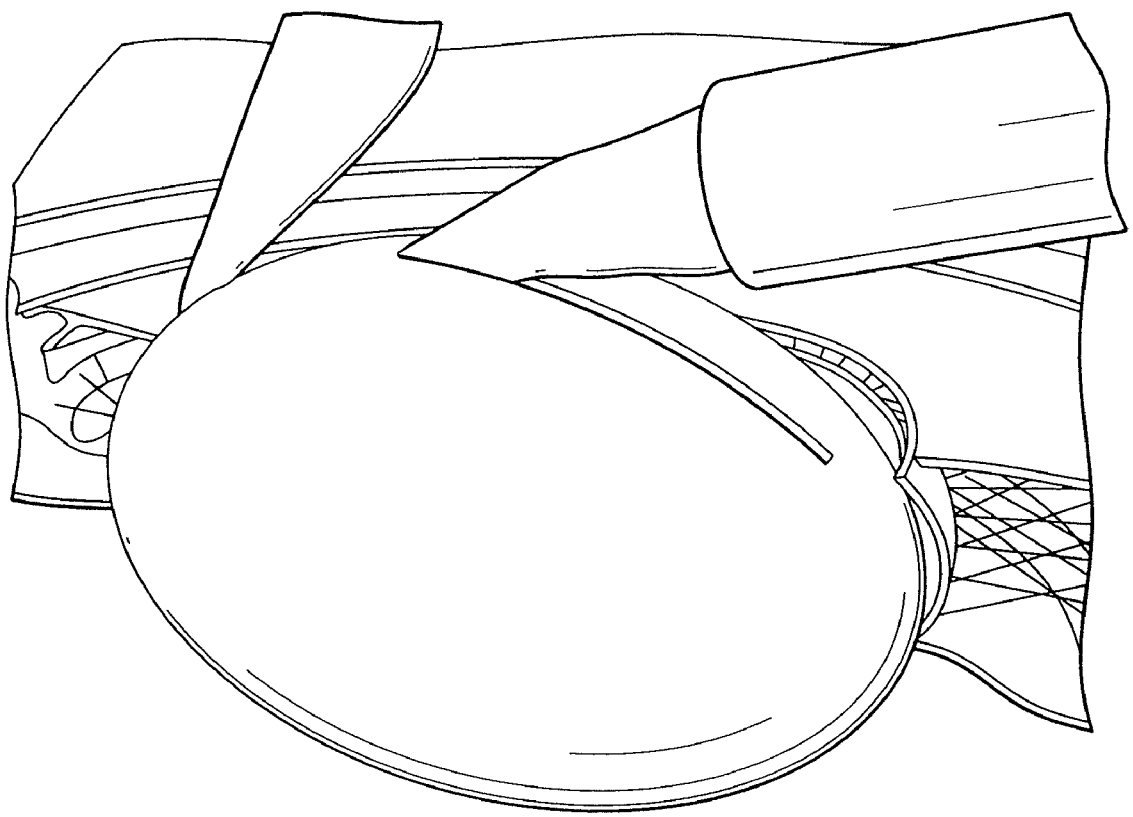

As noted above an alternative to emulsifying with an ultrasonic needle is to liquefy the ultrachopper produced fragments using a system which employs heated fluid pulses propelled from tip (e.g. Aqualase, Alcon). FIG. 28B and FIG. 31 illustrate an alternate instrument 6005 which is particularly suited for use during a liquefaction process. Instrument 6005 is shown in the preferred embodiment as a "microspoon" helps by way of its concave recessed tip in preventing a repelling of fragments by the liquefying probe. As seen from FIG. 31, micro-spoon 6005 features a hand grasp 6009 which functions as a support base for leg extension 6006 from which is angled off leg extension 6007 having spoon-shaped small tip component 6008 or "microspoon". Tip component 6008 is shown as extending in the same axial direction as leg 6007. This is different when compared to nucleus sustainer 6000 having a similar base 6001, first leg 6002 and second leg 6003, but having a spherical tip that is formed at the end of a 90° bent segment B. The fragment facilitator 5000 replaces band section B and the spherical tip found in instrument 6000 with a flattened distal end F, which is suited for insertion into cuts formed by the cutting device to help in providing an opposite bias force to promote separation of the cataract.

It should be emphasized that the above-described embodiment of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

The invention claimed is:

1. A cutting device for use in ophthalmologic surgery, comprising:
   an ultrasonic energy transmission section and a tip section, said tip section having a distally flattened material contact blade section that comprises an inferior, material contact point, an inferior edge that extends proximally away from said contact point, and a superior, forward edge that extends in sloped fashion proximally away from said contact point and which forward edge is free of an aspiration port, the inferior, material contact point being the distal most point of the blade section such that the entire blade section falls at or proximal to a superior to inferior extending plane that passes through said material contact point and extends transverse to a proximal-to-distal extending axis of said blade section, and wherein said superior forward edge extends between an upper edge and a lower edge of said blade section, and said lower edge includes said inferior edge which extends to said contact point and which inferior edge is thinner than said upper edge, and wherein said inferior edge includes a linear section originating and extending proximally away from the distal most point of the blade section and wherein said blade section has opposing essentially planar side walls extending proximally away from said superior forward edge positioned at the distal end of said blade section and which side walls diverge in a distal to proximal direction starting from said superior forward edge, and wherein said side walls converge in a superior to inferior direction at least at a border region with said superior forward edge;

wherein said inferior edge includes a recessed, concave section which originates and extends in a superior direction from the proximal most end of the linear section.

2. The cutting device as recited in claim 1 wherein at least one of said side walls includes a groove extending proximally away from said superior forward edge.

3. The cutting device as recited in claim 2, wherein there are at least a pair of grooves on said at least one side wall.

4. The cutting device as recited in claim 1 wherein said ultrasonic transmission section comprises a shaft end and an ultrasonic source connector, and said tip section includes a transition section having a converging surface in extending from a larger width cross-section of said shaft to a smaller width cross section of said blade section with width being in a direction perpendicular to a vertical inferior to superior extending plane.

5. The cutting device as recited in claim 1 wherein said superior forward edge includes a sloping, straight edge portion extending proximally away from a distal most end of the blade section at an angle of about 10 to 45 degrees relative to said plane.

6. The cutting device as recited in claim 5 wherein said ultrasonic transmission section includes a shaft and said tip section includes a transition section that diverges in going from said blade section toward said shaft, and said upper edge extends between a proximal end of said superior forward edge to said transition section, and said upper edge slopes upwardly in a distal to proximal direction.

7. The cutting device as recited in claim 1 wherein said superior forward edge comprises a curved edging section in said blade section.

8. The cutting device as recited in claim 7 wherein said superior forward edge includes a straight front section extending upward away from a distal most end of said blade section and a curved section that extends away from a proximal end of said straight front section.

9. The cutting device as recited in claim 8 wherein said contact point defines a vertex between said superior forward edge and said linear section.

10. A phacoemulsification device comprising:
a cutting device as recited in claim 1;
an ultrasonic vibration generator which is placed in ultrasonic vibration transmission communication with said cutting device; and
wherein said ultrasonic transmission section includes a shaft and said tip section includes a transition section that diverges in going from said blade section to said shaft, a phacoemulsification housing which receives said cutting device and comprises a sleeve extending about said shaft and, when said cutting device is in use, distal of an aspiration port formed in a border region between said shaft and said transition section and which aspiration port extends at least partly within a converging portion of said transition section.

11. The cutting device of claim 1 wherein said linear section slopes upward at an angle of 5° to 30° relative to a horizontal plane extending through the material contact point and parallel to the proximal-to-distal extending axis.

12. The cutting device of claim 1 wherein said linear section has rounded material contact edging.

13. The cutting device of claim 1 wherein said divergence is 3° to 4°.

14. A cutting device for use in ophthalmologic surgery, comprising:
an ultrasonic energy transmission section and a tip section, said tip section having a distally flattened material contact blade section that comprises an inferior, material contact point, an inferior edge that extends proximally away from said contact point, and a superior, forward edge that extends in sloped fashion proximally away from said contact point and which forward edge is free of an aspiration port, the inferior, material contact point being the distal most point of the blade section such that the entire blade section falls at or proximal to a superior to inferior extending plane that passes through said material contact point and extends transverse to a proximal-to-distal extending axis of said blade section, and wherein said superior forward edge extends between an upper edge and a lower edge of said blade section, and said lower edge includes said inferior edge which extends to said contact point and which inferior edge is thinner than said upper edge, and wherein said inferior edge includes a linear section originating and extending proximally away from the distal most point of the blade section and wherein said blade section has opposing essentially planar side walls extending proximally away from said superior forward edge positioned at the distal end of said blade section and which side walls diverge in a distal to proximal direction starting from said superior forward edge, and wherein said side walls converge in a superior to inferior direction at least at a border region with said superior forward edge;

wherein said ultrasonic transmission section includes a shaft and said tip section includes a transition section that diverges in going from said blade section to said shaft, and wherein the linear section represents the inferior most portion of said blade section and an underside concave edge section extends upward and off from a proximal end of said linear section toward said transition section, and said forward edge extends above both said linear section and said concave edge section.

15. A cutting device for use in ophthalmologic surgery, comprising:

an ultrasonic energy transmission section and a tip section, said tip section having a distally flattened material contact blade section that comprises an inferior, material contact point, an inferior edge that extends proximally away from said contact point, and a superior, forward edge that extends in sloped fashion proximally away from said contact point and which forward edge is free of an aspiration port, the inferior, material contact point being the distal most point of the blade section such that the entire blade section falls at or proximal to a superior to inferior extending plane that passes through said material contact point and extends transverse to a proximal-to-distal extending axis of said blade section, and wherein said superior forward edge extends between an upper edge and a lower edge of said blade section, and said lower edge includes said inferior edge which extends to said contact point and which inferior edge is thinner than said upper edge, and wherein said inferior edge includes a linear section originating and extending proximally away from the distal most point of the blade section and wherein said blade section has opposing essentially planar side walls extending proximally away from said superior forward edge positioned at the distal end of said blade section and which side walls diverge in a distal to proximal direction starting from said superior forward edge, and wherein said side walls converge in a superior to inferior direction at least at a border region with said superior forward edge;

wherein said ultrasonic transmission section includes a shaft and said tip section includes a transition section that diverges in going from said blade section to said shaft, and wherein said blade section comprises a sloping upper edge that extends upward from a proximal most point of a curved upper edge region of said superior forward edge to said transition section, and the inferior edge of said blade section further comprising a bottom edge comprising a straight, rounded edge bottom section which terminates, along a longitudinal axis of said cutting device, distally of said proximal most point, and the inferior edge section further comprises a curved edge bottom section extending between said linear section and said transition section.

16. A cutting device for use in ophthalmologic surgery, comprising:
an ultrasonic transmission section, and
a tip section supported by said ultrasonic transmission section, said tip section comprising an opposite side walled blade section that is aspiration port free and wherein side walls of said opposite side walled blade section converge toward one another in a superior to inferior direction to form a lower or inferior material contact edge in said blade section, and
wherein said blade section has a forward most front edge that slopes upwardly and proximally starting from an inferior, distal most point of said blade section, and
wherein said opposite side walls diverge in extending proximally out away from said forward most front edge with the divergence initiating at the forward most front edge;
wherein said blade section has a bottom edge extending off from said distal point, said bottom edge including a straight edge section extending proximally away from said distal point and said bottom edge further comprises a concave edge section proximal to said straight section of said bottom edge.

17. The cutting device as recited in claim 16 wherein
the forwardmost front edge slopes upwardly and proximally in straight edge fashion away from the inferior, most distal point of said blade section.

18. The cutting device is recited in claim 17 wherein said bottom edge straight section extends to said distal point.

19. The cutting device as recited in claim 16, wherein said bottom edge straight section extends off from said distal point and said blade section has an upper edge, and said forward most front edge has a curved section that extends distally away from a distal most end of said upper edge, which said upper edge has a thicker width than said bottom edge straight section.

20. The cutting device is recited in claim 16 wherein said ultrasonic transmission section includes a shaft and said tip section includes a transition section that diverges in going from said blade section to said shaft, and wherein said blade section has an upper edge extending from an uppermost end of said forward most front edge to said transition section, and said bottom edge extends from a lowermost end of said forward most front edge, which coincides with said most distal point, to said transition section, and said upper edge is shorter in longitudinal length than said bottom edge.

21. The cutting device as recited in claim 1, wherein
said blade section comprises opposing essentially planar side walls that continuously converge all the way from a wider upper edge to the thinner lower edge, and wherein said superior, forward edge represents a forward most edge of said blade section, and said forward most edge has a lower end that is more distally positioned than an upper end.

22. The cutting device as recited in claim 1 wherein said blade section has opposing essentially planar side walls extending proximally away from said superior forward edge positioned at the distalmost end of said blade section.

23. The cutting device as recited in claim 22 wherein said sidewalls diverge, starting from the forward edge, in going proximally away from the forward edge of said blade section.

24. A cutting device for use in ophthalmologic surgery, comprising:
an ultrasonic transmission section, and
a tip section supported by said ultrasonic transmission section, said tip section comprising an opposite side walled blade section that is aspiration port free and wherein side walls of said opposite side walled blade section converge toward one another in a superior to inferior direction to form a lower or inferior material contact edge in said blade section, and
wherein said blade section has a forward most front edge that slopes upwardly and proximally starting from an inferior, distal most point of said blade section, and
wherein said opposite side walls diverge in extending proximally out away from said forward most front edge with the divergence initiating at the forward most front edge;
wherein said inferior material contact edge includes a recessed, concave section which originates and extends in a superior direction from the proximal most end of a linear section of said inferior material contact edge positioned distally of the recessed, concave section.

25. The cutting device of claim 24 wherein said linear section slopes upward at an angle of 5° to 30° from a horizontal plane extending through the distal most point and parallel to a proximal-to-distal extending axis.

* * * * *